US011332789B2

(12) United States Patent
Yang

(10) Patent No.: US 11,332,789 B2
(45) Date of Patent: May 17, 2022

(54) COMPOSITIONS AND METHODS FOR DIAGNOSING AND TREATING HYPERLIPIDEMIA-RELATED DISEASES

(71) Applicant: Temple University-Of The Commonwealth System of Higher Education, Philadelphia, PA (US)

(72) Inventor: Xiao-Feng Yang, Huntingdon Valley, PA (US)

(73) Assignee: Temple University-Of The Commonwealth System of Higher Education, Philadelphia, PA (US)

( * ) Notice: Subject to any disclaimer, the term of this patent is extended or adjusted under 35 U.S.C. 154(b) by 0 days.

(21) Appl. No.: 16/417,987

(22) Filed: May 21, 2019

(65) Prior Publication Data
US 2019/0352713 A1 Nov. 21, 2019

Related U.S. Application Data

(60) Provisional application No. 62/674,088, filed on May 21, 2018.

(51) Int. Cl.
  *C12Q 1/6876* (2018.01)
  *C12Q 1/6806* (2018.01)
  *C12Q 1/686* (2018.01)

(52) U.S. Cl.
  CPC ......... *C12Q 1/6876* (2013.01); *C12Q 1/6806* (2013.01); *C12Q 1/686* (2013.01); *C12Q 2600/112* (2013.01); *C12Q 2600/118* (2013.01); *C12Q 2600/158* (2013.01); *C12Q 2600/178* (2013.01)

(58) Field of Classification Search
  None
  See application file for complete search history.

(56) References Cited

U.S. PATENT DOCUMENTS

| 2005/0261218 | A1 | 11/2005 | Esau | |
| 2012/0040353 | A1* | 2/2012 | Kerin | C12Q 1/6886 435/6.12 |
| 2013/0078225 | A1 | 3/2013 | Zeng | |
| 2013/0130927 | A1 | 5/2013 | Heneghan | |
| 2013/0331433 | A1* | 12/2013 | Thibonnier | C12N 15/113 514/44 A |
| 2016/0251656 | A1 | 9/2016 | Berriel Diaz | |
| 2017/0362656 | A1 | 12/2017 | Umansky | |

OTHER PUBLICATIONS

Baker, Rebecca G., Matthew S. Hayden, and Sankar Ghosh. "NF-κB, inflammation, and metabolic disease." Cell metabolism 13.1 (2011): 11-22.
Bhattacharyya, Swati, et al. "Egr 1: new conductor for the tissue repair orchestra directs harmony (regeneration) or cacophony (fibrosis)." The Journal of pathology 229.2 (2013): 286-297.
Buettner, Christoph, et al. "Critical role of STAT3 in leptin's metabolic actions." Cell metabolism 4.1 (2006): 49-60.
Chait, Alan, and Karin E. Bornfeldt. "Diabetes and atherosclerosis: is there a role for hyperglycemia?." Journal of lipid research 50.Supplement (2009): S335-S339.
Coleman, Chasity B., et al. "Elevation of miR-221 and-222 in the internal mammary arteries of diabetic subjects and normalization with metformin." Molecular and cellular endocrinology 374.1-2 (2013): 125-129.
Coskunpinar, Ender, et al. "Circulating miR-221-3p as a novel marker for early prediction of acute myocardial infarction." Gene 591.1 (2016): 90-96.
Deiuliis, J. A. "MicroRNAs as regulators of metabolic disease: pathophysiologic significance and emerging role as biomarkers and therapeutics." International journal of obesity 40.1 (2016): 88-101.
Feinberg, Mark W., and Kathryn J. Moore. "MicroRNA regulation of atherosclerosis." Circulation research 118.4 (2016): 703-720.
Fujimoto, Minoru, and Tetsuji Naka. "SOCS1, a negative regulator of cytokine signals and TLR responses, in human liver diseases." Gastroenterology research and practice 2010 (2010).
Gaggini, Melania, et al. "Non-alcoholic fatty liver disease (NAFLD) and its connection with insulin resistance, dyslipidemia, atherosclerosis and coronary heart disease." Nutrients 5.5 (2013): 1544-1560.
Gonzalez-Navarro, Herminia, et al. "Molecular mechanisms of atherosclerosis in metabolic syndrome: role of reduced IRS2-dependent signaling." Arteriosclerosis, thrombosis, and vascular biology 28.12 (2008): 2187-2194.
Hanin, Geula, et al. "miRNA-132 induces hepatic steatosis and hyperlipidaemia by synergistic multitarget suppression." Gut 67.6 (2018): 1124-1134.
Hayden, Matthew S., and Sankar Ghosh. "NF-κB, the first quarter-century: remarkable progress and outstanding questions." Genes & development 26.3 (2012): 203-234.
Hinnouho, Guy-Marino, et al. "Metabolically healthy obesity and risk of mortality: does the definition of metabolic health matter?." Diabetes care 36.8 (2013): 2294-2300.
Jung, Chang Hee, Woo Je Lee, and Kee-Ho Song. "Metabolically healthy obesity: a friend or foe?." The Korean journal of internal medicine 32.4 (2017): 611-621.
Kothapalli, Devashish, et al. "Apolipoprotein E-mediated cell cycle arrest linked to p27 and the Cox2-dependent repression of miR221/222." Atherosclerosis 227.1 (2013): 65-71.
Latreille, Mathieu, et al. "MicroRNA-7a regulates pancreatic β cell function." The Journal of clinical investigation 124.6 (2014): 2722-2735.
Liang, Ying Zhi, et al. "Identification of stress related microRNA biomarkers in type 2 diabetes mellitus: A systematic review and meta analysis." Journal of diabetes (2018). 12 pages.
Mali, Shrikant Balasaheb. "Review of STAT3 (Signal Transducers and Activators of Transcription) in head and neck cancer." Oral oncology 51.6 (2015): 565-569.
Mandraffino, Giuseppe, et al. "Circulating progenitor cells in hypertensive subjects: effectiveness of a treatment with olmesartan in improving cell number and miR profile in addition to expected pharmacological effects." 2017, PLOS One, 12(3):e0173030. 15 pages.

(Continued)

*Primary Examiner* — Brian Whiteman
(74) *Attorney, Agent, or Firm* — Riverside Law LLP

(57) ABSTRACT

The invention provides compositions and methods for the diagnosis, treatment, assessment, and characterization of hyperlipidemia-related diseases and disorders, including atherosclerosis, non-alcoholic fatty liver disease, obesity and diabetes mellitus in a subject in need thereof, based on the expression level of at least one miRNA that is associated with these diseases and disorders.

4 Claims, 27 Drawing Sheets

(56) References Cited

OTHER PUBLICATIONS

Mazière, Cécile, et al. "Oxidized LDL activates STAT1 and STAT3 transcription factors: possible involvement of reactive oxygen species." FEBS letters 448.1 (1999): 49-52.
Meerson, A., et al. "Human adipose microRNA-221 is upregulated in obesity and affects fat metabolism downstream of leptin and TNF-α." Diabetologia 56.9 (2013): 1971-1979.
Min, Hae-Ki, et al. "Activation of the GP130-STAT3 axis and its potential implications in nonalcoholic fatty liver disease." American Journal of Physiology-Gastrointestinal and Liver Physiology 308.9 (2015): G794-G803.
Moore, Justin Xavier, Ninad Chaudhary, and Tomi Akinyemiju. "Peer reviewed: Metabolic syndrome prevalence by race/ethnicity and sex in the United States, National Health and Nutrition Examination Survey, 1988-2012." Preventing chronic disease 14 (2017). 16 pages.
Pamukcu, Burak, Gregory YH Lip, and Eduard Shantsila. "The nuclear factor—kappa B pathway in atherosclerosis: a potential therapeutic target for atherothrombotic vascular disease." Thrombosis research 128.2 (2011): 117-123.
Pi-Sunyer, Xavier. "The medical risks of obesity." Postgraduate medicine 121.6 (2009): 21-33.
Priceman, Saul J., et al. "Regulation of adipose tissue T cell subsets by Stat3 is crucial for diet-induced obesity and insulin resistance." Proceedings of the National Academy of Sciences 110.32 (2013): 13079-13084.
Soh, James, et al. "MicroRNA-30c reduces hyperlipidemia and atherosclerosis in mice by decreasing lipid synthesis and lipoprotein secretion." Nature medicine 19.7 (2013): 892-900.
Srikanthan, Krithika, et al. "Systematic review of metabolic syndrome biomarkers: a panel for early detection, management, and risk stratification in the West Virginian population." International journal of medical sciences 13.1 (2016): 25-38.
Talepoor, Atefe Ghamar, et al. "Hydrogen peroxide and lipopolysaccharide differentially affect the expression of microRNAs 10a, 33a, 21, 221 in endothelial cells before and after coculture with monocytes." International journal of toxicology 36.2 (2017): 133-141.
Ueki, Kohjiro, Tatsuya Kondo, and C. Ronald Kahn. "Suppressor of cytokine signaling 1 (SOCS-1) and SOCS-3 cause insulin resistance through inhibition of tyrosine phosphorylation of insulin receptor substrate proteins by discrete mechanisms." Molecular and cellular biology 24.12 (2004): 5434-5446.
Vienberg, Sara, et al. "Micro RNA s in metabolism." Acta physiologica 219.2 (2017): 346-361.
Villarino, Alejandro V., et al. "Mechanisms of Jak/STAT signaling in immunity and disease." The Journal of Immunology 194.1 (2015): 21-27.
Vinnikov, Ilya A., et al. "Hypothalamic miR-103 protects from hyperphagic obesity in mice." Journal of Neuroscience 34.32 (2014): 10659-10674.
Virtue, Anthony, et al. "MicroRNA-155 deficiency leads to decreased atherosclerosis, increased white adipose tissue obesity, and non-alcoholic fatty liver disease a novel mouse model of obesity paradox." Journal of Biological Chemistry 292.4 (2017): 1267-1287.
Virtue, Anthony, et al. "Structural evidence of anti-atherogenic microRNAs." Frontiers in bioscience: a journal and virtual library 16 (2011): 3133.-3145.
Virtue, Anthony, Hong Wang, and Xiao-feng Yang. "MicroRNAs and toll-like receptor/interleukin-1 receptor signaling." Journal of hematology & oncology 5.1 (2012): 66. 17 pages.
Wang, Rong, et al. "Protein inhibitor of activated STAT3 suppresses oxidized LDL-induced cell responses during atherosclerosis in apolipoprotein E-deficient mice." Scientific reports 6 (2016): 36790. 13 pages.
Yang, Yang, et al. "MicroRNA-155 promotes atherosclerosis inflammation via targeting SOCS1." Cellular Physiology and Biochemistry 36.4 (2015): 1371-1381.
Zeng, Lu, et al. "Signal transductions and nonalcoholic fatty liver: a mini-review." International journal of clinical and experimental medicine 7.7 (2014): 1624. 8 pages.
Zhang et al., "Dietary obesity-induced Egr-1 in adipocytes facilitates energy storage via suppression of FOXC2", Scientific Reports, 3:1476, DOI: 10.1038/srep01476, (2013) 10 pages.
Zhang, Xinhuan, et al. "Expression profiles of six circulating microRNAs critical to atherosclerosis in patients with subclinical hypothyroidism: a clinical study." The journal of clinical endocrinology & metabolism 99.5 (2014): E766-E774.

* cited by examiner

Fig. 1A

| Disease | Characteristics | PubMed ID |
|---|---|---|
| Atherosclerosis | Hyperlipidemia, plaque formation in medium to large-sized arteries, immune cell infiltration in medium to large-sized arteries, arterial inflammation, foam cells in plaque, endothelial dysfunction, reactive oxygen species production in arterial endothelium | 24902970; 26750181 |
| Non-Alcoholic Fatty Liver Disease (NAFLD) | Hepatic steatosis, hepatic inflammation, maybe hepatic fibrosis, hyperlipidemia | 26057287; 26980160; 22418885 |
| Obesity | Hyperlipidemia, respiratory difficulty, skin disorders, inflammation in adipose tissue | 25161465; 17316295 |
| Type 2 Diabetes Mellitus (T2DM)/Insulin Resistance (IR) | Insulin resistance, hyperinsulinemia, hyperglycemia, central obesity, inflammation, hyperlipidemia | 23071876; 19770178; 17316295; 21172030; 11183421; 18227495 |

Fig. 1B

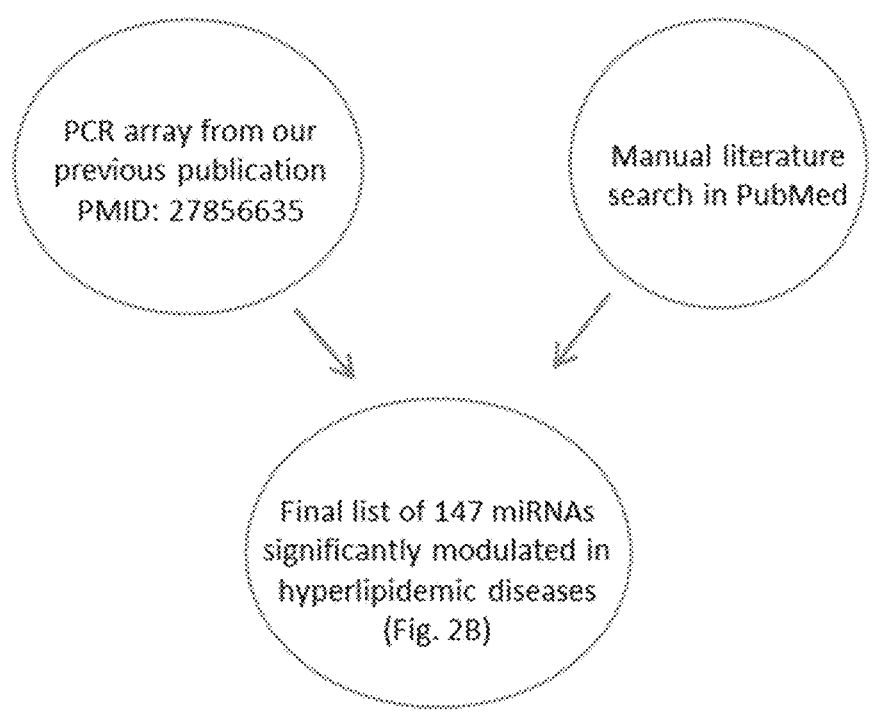

| MiRNA | Atherosclerosis | NAFLD | Obesity | Type 2 Diabetes/IR |
|---|---|---|---|---|
| let-7b | down | | | down |
| let-7c | up | | up | |
| miR-16 | | up | | up |
| miR-18a | | | up | up |
| miR-19a | down | | up | |
| miR-19b | up | | up | |
| miR-21 | up | down | | |
| miR-26a | down | up | | |
| miR-26b | | | up | up |
| miR-29 | up | | up | up |
| miR-30 | | | up | down |
| miR-34a | up | up | | up |
| miR-92a | up | | up | |
| miR-99a | | down | | down |
| miR-100 | | | down | down |
| miR-126 | up | | | down |
| miR-133 | down | | | down |
| miR-135b | | | down | down |
| miR-143 | down | | | |
| miR-144 | up | | | up |
| miR-146a | down | | up | up |
| miR-146b | | up | up | |
| miR-155 | up | down | down | up |
| miR-199a | down | up | down | down |
| miR-200 | up | up | | |
| miR-210 | up | up | up | up |
| miR-221 | up | up | down | |
| miR-222 | up | up | up | up |
| miR-335 | down | | | |
| miR-342 | up | | | down |

Fig. 2B

| Disease(s) | miRNA marker | |
|---|---|---|
| | Upregulated | Downregulated |
| Atherosclerosis | miR-126, miR-155, miR-342, | miR-19a, miR-26a, miR-143, miR-146a, miR-199a, miR-335, |
| Atherosclerosis + NAFLD | miR-200, miR-222 | - |
| Atherosclerosis + T2DM/IR | miR-144 | let-7b, miR-133 |
| Atherosclerosis + Obesity | let-7c, miR-19b, miR-21, miR-92a, miR-210 | - |
| NAFLD | let-7b, miR-26a, | miR-21, |
| NAFLD + T2DM/IR | miR-16 | miR-99a |
| NAFLD + Obesity | - | - |

Fig. 2C

| | | |
|---|---|---|
| Obesity | miR-19a, miR-30, miR-146a, miR-335 | miR-221, |
| Obesity + T2DM/IR | miR-18a, miR-26b | miR-100, miR-135b |
| T2DM/IR | miR-143, miR-199a | miR-30, miR-126b, miR-342 |
| Atherosclerosis + NAFLD + Obesity | | |
| Atherosclerosis + NAFLD + T2DM/IR | miR-34a, miR-221 | |
| Atherosclerosis + Obesity + T2DM/IR | miR-29 | |
| NAFLD + Obesity + T2DM/IR | miR-146b | miR-155 |
| Atherosclerosis + NAFLD + Obesity + T2DM/IR | | |

Symbols represent miRNAs that are uniquely expressed in the classical solitary diseases as shown in Fig. 2B.

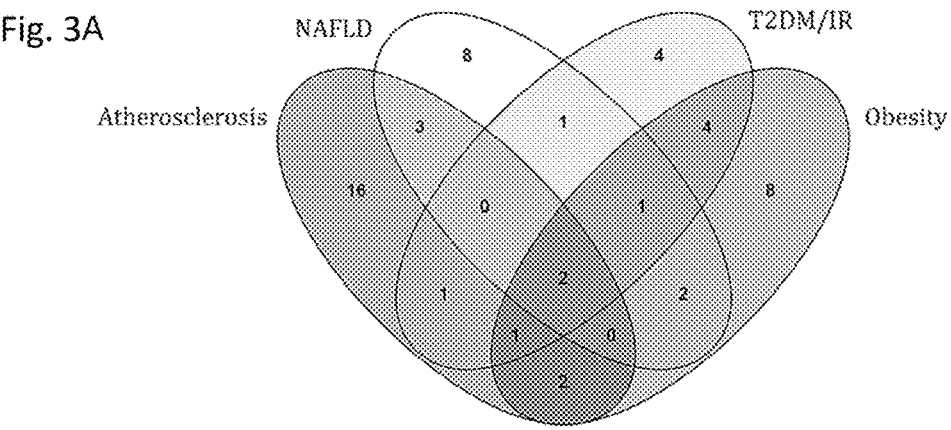

| Single Disease | Transcription Factor(s) | Number |
|---|---|---|
| Atherosclerosis | POU5F1, SOX2, ZFP42, KLF2, SMAD4, TP73, SRF, CEBPA, MECOM, MYF5, MYF6, MYOG, YY1, CEBPB, PPARG, MEF2 | 16 |
| NAFLD | ZEB1, ZEB2, TP63, ESRRG, NR0B2, GATA1, GATA4, TCF3 | 8 |
| Obesity | MYCN, SPI1, TLX1, TLX3, HNF1A, HNF1B, FLI1, STAT5A | 8 |
| T2DM/IR | SOX9, BRD2, E2F3, C-REL | 4 |

| Co-morbid Diseases | Transcription Factor(s) | Number |
|---|---|---|
| T2DM/IR + Obesity | E2F1, ESR1, STAT5B, MYB | 4 |
| Atherosclerosis + NAFLD | TWIST1, SMAD3, TCF4 | 3 |
| Atherosclerosis + Obesity | NKX2-5, MYOD1 | 2 |
| NAFLD + Obesity | SP1, NFKB1 | 2 |
| Atherosclerosis + T2DM/IR | HMGA1 | 1 |
| NAFLD + T2DM/IR | CREB1 | 1 |
| NAFLD + Obesity + T2DM/IR | MYC | 1 |
| Atherosclerosis + T2DM/IR + Obesity | TP53 | 1 |
| Atherosclerosis + NAFLD + T2DM/IR + Obesity | EGR1, STAT3 | 2 |

Fig. 3B

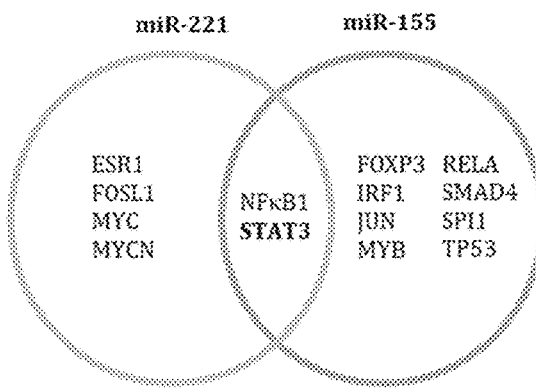

Fig. 4A

| miR-221 Targets | Atherosclerosis | NAFLD | Obesity | Diabetes/IR |
|---|---|---|---|---|
| CDKN1B | 19150885; 23409140; 19088079; 26451018* | - | - | 23648338 |
| KIT | 19088079 | - | - | 19351599 |
| CDKN1C | 19150885 | - | - | - |
| BBC3 | - | 21633093 | - | - |
| TIMP3 | - | 19711427; 19962668 | - | 23797704 |
| ICAM1 | - | - | 26065857 | - |
| PTEN | 27644883 | 19711427; 19962668 | - | 21118127 |
| ETS1 | 25893733; 23687352; 21310411; 24285111 | - | 23756832 | 23756832 |
| THBS1 | - | - | 23867206 | - |
| PAK1 | 23333386 | - | - | - |
| PIK3R1 | 25236949 | - | - | - |

NAFLD: Nonalcoholic liver disease
T2DM/IR: type 2 diabetes mellitus/insulin resistance
From 82 targets

| Atherosclerosis | CDKN1C, PAK1, PIK3R1 |
| NAFLD | BBC3 |
| Obesity | ICAM1, THBS1 |
| Atherosclerosis + T2DM/IR | CDKN1B, KIT |
| NAFLD + T2DM/IR | TIMP3 |
| Atherosclerosis + NAFLD + T2DM/IR | PTEN |
| Atherosclerosis + Obesity + T2DM/IR | ETS1 |

| miR-155 Targets | Atherosclerosis | NAFLD | Obesity | T2DM/IR |
|---|---|---|---|---|
| Fadd | 23797321* | - | - | - |
| Nr1h3 | - | 23991091 | - | - |
| Socs1 | 24504735; 26159489 | 23991091 | 27671445 | 23991091; 27671445; 27711113 |
| Cebpb | - | - | 26953132 | 27711113; 22647600 |
| Hdac4 | - | - | - | 27711113 |
| Ets1 | 21310411 | - | - | - |
| Hbp1 | 24675724 | - | - | - |
| Mapk1 | 23189122 | - | - | - |
| Pparg | - | - | 26829440 | - |
| Sfpi1 | 23041630 | - | - | - |
| Ski | - | - | - | 23560074 |
| AT1R | 24737641 | - | - | - |
| CARHSP1 | 26899994 | - | - | - |
| CSF1R | 25810298 | - | - | - |
| MAP3K10 | 23189122 | - | - | - |
| MYD88 | 21030878 | - | - | - |
| Foxp3 | - | 23567045 | - | - |
| Ces3/TGH | - | 25799309 | - | - |
| Bcl6 | 23041630; 24504735 | - | - | - |
| Mst2 | 25892184 | - | - | - |

NAFLD: nonalcoholic liver disease
T2DM/IR: type 2 diabetes mellitus/insulin resistance
From 176 targets

Fig. 5A

| Atherosclerosis | Fadd, Ets1, Hbp1, Mapk1, Sfpi1, AT1R, CARHSP1, CSF1R, MAP3K10, MYD88, Bcl6, Mst2 |
|---|---|
| NAFLD | Nr1h3, Foxp3, Ces1 |
| Obesity | Pparg |
| T2DM/IR | Hdac4, Ski |
| T2DM/IR + Obesity | Cebpb |
| Atherosclerosis + NAFLD + T2DM/IR + Obesity | Socs1 |

| Pathway | A+D | A+N | A+N+O | A+N+O+D | A+N+O+B | A+O | A+O+B | Athero+D | Athero | Athero+O+D | Diabetes+D | Diabetes+Up | N+D | N+O+D | NAFLD Down | NAFLD Up | O+D | Obesity Down | Obesity Up |
|---|---|---|---|---|---|---|---|---|---|---|---|---|---|---|---|---|---|---|---|
| | | | | | | | | Cancer | | | | | | | | | | | |
| Colorectal Cancer Metastasis Signaling | Down | Up | . | . | . | Up | . | Down | . | . | Down | . | . | . | . | . | Down | Down | . |
| Molecular Mechanisms of Cancer | . | Up | Up | . | . | Up | Up | Down | Up | . | Down | Up | Up | . | Down | Up | Up | Down | Up |
| Pancreatic Adenocarcinoma Signaling | Down | . | . | . | . | Up | . | Down | Up | . | Down | Up | U/D | . | Down | Up | Up | Down | Up |
| Glioblastoma Multiforme Signaling | Down | . | Up | . | . | . | . | Down | Up | . | Down | Up | Down | . | . | . | Down | Down | . |
| Ovarian Cancer Signaling | . | . | Up | . | . | . | . | . | . | . | . | Up | . | . | Down | . | . | . | . |
| Glioma Signaling | Down | . | . | . | . | . | . | . | . | . | . | . | . | . | . | . | . | . | . |
| Small Cell Lung Cancer Signaling | . | . | Up | . | . | . | . | . | . | . | . | . | . | . | Down | . | Up | . | . |
| Role of Tissue Factor in Cancer | U/D | . | . | . | . | . | . | . | . | . | . | . | . | . | . | . | . | . | . |
| Melanoma Signaling | . | . | . | . | . | . | . | Down | . | . | . | . | . | . | Down | . | . | . | . |
| Chronic Myeloid Leukemia Signaling | Down | . | . | . | . | Up | . | Down | . | . | Down | . | Up | . | Down | . | . | . | Up |
| PTEN Signaling | Down | . | Up | . | . | . | . | . | . | . | . | . | . | . | . | . | . | . | . |
| Regulation of the Epithelial Mesenchymal Transition Pathway | . | . | . | . | . | . | . | . | . | . | . | . | . | . | . | Up | . | . | . |

Fig. 6A

| Pathway | A+D | A+N | A+N+D | A+N+O | A+N+O+D | A+O | A+O+D | Athero Down | Athero Up | Diabetes Down | Diabetes Up | N+O | N+O+D | NAFLD Down | NAFLD Up | O+D | Obesity Down | Obesity Up |
|---|---|---|---|---|---|---|---|---|---|---|---|---|---|---|---|---|---|---|
| Pathway | | | | | | | | | Proliferation/Survival | | | | | | | | | |
| Cell Cycle: G1/S Checkpoint Regulation | - | - | Up | - | - | - | - | - | - | - | - | - | - | - | - | - | - | - |
| Cyclins and Cell Cycle Regulation | - | - | Up | - | - | - | - | - | - | - | - | - | - | - | - | - | - | - |
| EIF2 Signaling | - | - | - | - | - | - | - | - | Up | - | Up | - | - | - | - | Up | - | - |
| Regulation of eIF4 and p70S6K Signaling | - | - | - | - | - | - | - | - | - | - | - | Down | - | - | - | - | - | - |
| Myc Mediated Apoptosis Signaling | - | - | - | - | - | - | - | - | - | - | - | Down | - | - | - | - | - | - |
| Regulation of Cellular Mechanics by Calpain Protease | - | - | - | - | - | - | - | - | - | - | - | - | - | - | - | - | Down | - |
| PEDF Signaling | Down | Up | - | - | - | - | - | - | - | - | - | - | - | - | - | - | - | - |
| Extrinsic Prothrombin Activation Pathway | Up | - | - | - | - | - | - | - | - | - | - | - | - | - | - | - | - | - |
| Coagulation System | Up | - | - | - | - | - | - | - | - | - | - | - | - | - | - | - | - | - |
| Intrinsic Prothrombin Activation Pathway | Up | - | - | - | - | - | - | - | - | - | - | - | - | - | - | - | - | - |

Fig. 6B

| Pathway | A+D | A+N | A+N+D | A+N+O | A+N+O+D | A+O | A+O+D | Athero Down | Athero Up | Diabetes Down | Diabetes Up | N+D | N+O+D | NAFLD Down | NAFLD Up | O+D | Obesity Down | Obesity Up |
|---|---|---|---|---|---|---|---|---|---|---|---|---|---|---|---|---|---|---|
| Role of Osteoblasts, Osteoclasts and Chondrocytes in Rheumatoid Arthritis | - | - | - | - | - | - | - | - | - | Arthritis | - | - | - | - | - | - | - | - |
| Osteoarthritis Pathway | - | Up | - | - | - | - | - | - | - | Down | - | - | - | - | - | Down | - | - |
| Role of Macrophages, Fibroblasts and Endothelial Cells in Rheumatoid Arthritis | - | Up | - | - | - | - | - | - | - | - | - | - | Up | - | - | Down | - | - |

Fig. 6C

| Pathway | A+D | A+N | A+N+D | A+N+O | A+N+O+D | A+O | A+O+D | Athero Down | Athero Up | Diabetes Down | Diabetes Up | N+D | N+O+D | NAFLD Down | NAFLD Up | O+D | Obesity Down | Obesity Up |
|---|---|---|---|---|---|---|---|---|---|---|---|---|---|---|---|---|---|---|
| | | | | | | | | | | Development | | | | | | | | |
| Neuregulin Signaling | | | | | | | | | | | | | | | | | | |
| Axonal Guidance Signaling | Down | | | | | | | | | | | | | | | | | |
| Role of NANOG in Mammalian Embryonic Stem Cell Pluripotency | | | | | | | | | Up | | | | | | Up | | | |
| Regulation of the Epithelial-Mesenchymal Transition Pathway | | | | | | | | | | | | | | | Up | | | |
| Human Embryonic Stem Cell Pluripotency | | | | | | | | | | | | | | | | Down | | |

Fig. 6D

| Pathway | A+D | A+N | A+N+D | A+N+O | A+N+O+D | A+O | A+O+D | Athero Down | Athero Up | Diabetes Down | Diabetes Up | N+D | N+O+D | NAFLD Down | NAFLD Up | O+D | Obesity Down | Obesity Up |
|---|---|---|---|---|---|---|---|---|---|---|---|---|---|---|---|---|---|---|
| | | | | | | | | Metabolism | | | | | | | | | | |
| Aryl Hydrocarbon Receptor Signaling | , | : | : | , | , | , | , | , | , | , | , | , | , | , | , | , | , | , |
| Glucocorticoid Receptor Signaling | , | Up | Up | , | , | Up | , | , | , | , | Up | , | , | , | Up | , | , | , |
| Sumoylation Pathway | , | Up | , | , | , | , | , | Down | , | , | , | , | , | , | , | U/D | , | , |
| Hepatic Cholestasis | , | , | , | , | , | , | , | , | , | , | , | , | Up | , | , | , | , | , |
| Hepatic Fibrosis / Hepatic Stellate Cell Activation | , | , | , | , | , | Up | Up | , | , | , | , | , | Up | , | , | , | , | , |
| Insulin Receptor Signaling | , | , | , | , | , | , | , | , | , | , | , | Down | , | , | , | , | , | , |
| PPAR Signaling | , | , | , | , | , | , | , | , | , | , | , | , | Up | , | , | , | , | , |

Fig. 6E

| Pathway | A+D | A+N | A+N+D | A+N+O | A+N+O+D | A+O | A+O+D | Athero Down | Athero Up | Diabetes Down | Diabetes Up | N+D | N+O+D | NAFLD Down | NAFLD Up | O+D | Obesity Down | Obesity Up |
|---|---|---|---|---|---|---|---|---|---|---|---|---|---|---|---|---|---|---|
| TGF-Signaling | - | - | - | - | - | - | - | Immunology | | | | | | | | | | |
| IL-8 Signaling | - | Up | - | - | - | - | - | - | - | - | - | - | - | - | - | - | - | Up |
| NF-kB Signaling | Down | - | - | - | - | - | - | - | - | - | - | - | - | - | - | Down | - | - |
| p53 Signaling | - | - | Up | - | - | - | Up | - | Up | - | - | Up | - | - | - | - | - | Up |
| STAT3 Pathway | - | - | - | - | - | Up | - | - | - | - | - | - | - | - | - | - | - | - |
| Acute Phase Response Signaling | Up | - | - | - | - | - | - | - | - | - | - | - | Up | - | - | - | - | - |
| iNOS Signaling | - | - | - | - | - | - | - | - | - | - | - | - | - | - | - | - | - | - |

Fig. 6F

| Disease/s | Cancer (NOP: 12) | Proliferation/Survival (NOP: 10) | Arthritis (NOP: 3) | Development (NOP: 5) | Metabolism (NOP: 7) | Immunology (NOP: 7) |
|---|---|---|---|---|---|---|
| | | | Percentage of Pathways per Category | | | |
| A+D | 50 | 40 | 0 | 20 | 0 | 28.6 |
| A+N | 16.7 | 10 | 66.7 | 0 | 28.6 | 14.3 |
| A+N+D | 33.3 | 20 | 0 | 0 | 28.6 | 14.3 |
| A+N+O | 0 | 0 | 0 | 0 | 0 | 0 |
| A+N+O+D | 0 | 0 | 0 | 0 | 0 | 0 |
| A+O | 33.3 | 0 | 0 | 0 | 28.6 | 28.6 |
| A+O+D | 25 | 0 | 0 | 0 | 14.3 | 14.3 |
| Athero Down | 33.3 | 0 | 0 | 0 | 0 | 0 |
| Athero Up | 16.7 | 10 | 0 | 20 | 14.3 | 14.3 |
| Diabetes Down | 33.3 | 0 | 33.3 | 0 | 0 | 0 |
| Diabetes Up | 25 | 10 | 0 | 0 | 14.3 | 0 |
| N+D | 33.3 | 20 | 0 | 0 | 14.3 | 14.3 |
| N+O+D | 0 | 0 | 33.3 | 0 | 42.9 | 14.3 |
| NAFLD Down | 41.7 | 0 | 0 | 0 | 0 | 0 |
| NAFLD Up | 25 | 0 | 0 | 40 | 14.3 | 0 |
| O+D | 33.3 | 10 | 100 | 20 | 0 | 14.3 |
| Obesity Down | 33.3 | 10 | 0 | 0 | 0 | 0 |
| Obesity Up | 25 | 0 | 0 | 0 | 0 | 28.6 |

Fig. 6G

| Disease/s | Cancer (NOP: 12) | | Proliferation/Survival (NOP: 10) | | Arthritis (NOP: 3) | | Development (NOP: 5) | | Metabolism (NOP: 7) | | Immunology (NOP: 7) | |
|---|---|---|---|---|---|---|---|---|---|---|---|---|
| | DOWN | UP | DOWN | UP | DOWN | UP | DOWN | UP | DOWN | UP | DOWN | UP |
| A+D | 100(6) | 0 | 25(1) | 75(3) | 0 | 0 | 100(1) | 0 | 0 | 0 | 50(1) | 50(1) |
| A+N | 0 | 100(2) | 0 | 100(1) | 0 | 100(2) | 0 | 0 | 0 | 100(2) | 0 | 100(1) |
| A+N+D | 0 | 100(4) | 0 | 100(2) | 0 | 0 | 0 | 0 | 0 | 100(2) | 0 | 100(1) |
| A+N+O | 0 | 0 | 0 | 0 | 0 | 0 | 0 | 0 | 0 | 0 | 0 | 0 |
| A+N+O+D | 0 | 0 | 0 | 0 | 0 | 0 | 0 | 0 | 0 | 0 | 0 | 0 |
| A+O | 0 | 100(4) | 0 | 0 | 0 | 0 | 0 | 0 | 0 | 100(2) | 0 | 100(2) |
| A+O+D | 0 | 100(3) | 0 | 0 | 0 | 0 | 0 | 0 | 0 | 100(1) | 0 | 100(1) |
| Athero Down | 100(4) | 0 | 0 | 0 | 0 | 0 | 0 | 0 | 100(1) | 0 | 0 | 0 |
| Athero Up | 0 | 100(2) | 0 | 100(1) | 0 | 0 | 0 | 100(1) | 0 | 0 | 0 | 100(1) |
| Diabetes Down | 100(4) | 0 | 100(2) | 0 | 100(1) | 0 | 0 | 0 | 0 | 0 | 0 | 0 |
| Diabetes Up | 0 | 100(3) | 0 | 0 | 0 | 0 | 0 | 0 | 100(1) | 100(1) | 0 | 0 |
| N+D | 25(1) | 75(3) | 0 | 100(1) | 0 | 0 | 0 | 0 | 0 | 0 | 0 | 100(1) |
| N+O+D | 0 | 0 | 0 | 0 | 100(3) | 100(1) | 0 | 0 | 0 | 100(3) | 0 | 100(1) |
| NAFLD Down | 100(5) | 0 | 0 | 0 | 0 | 0 | 100(1) | 100(2) | 0 | 100(1) | 0 | 0 |
| NAFLD Up | 0 | 100(3) | 0 | 100(1) | 0 | 0 | 0 | 0 | 0 | 0 | 0 | 0 |
| O+D | 50(2) | 50(2) | 0 | 0 | 0 | 0 | 0 | 0 | 0 | 0 | 100(1) | 0 |
| Obesity Down | 100(4) | 0 | 100(1) | 0 | 0 | 0 | 0 | 0 | 0 | 0 | 0 | 0 |
| Obesity Up | 0 | 100(3) | 0 | 0 | 0 | 0 | 0 | 0 | 0 | 0 | 0 | 100(2) |

Pathway Categories
Percentage of Modulated Pathways by Direction (NOP modulated)

Fig. 6H

| No. of Pathways | Disease(s) | Pathways |
|---|---|---|
| 0 | Atherosclerosis, NAFLD, Obesity (ANO) | N/A |
| | Atherosclerosis, NAFLD, Obesity, T2DM/IR (ANOD) | N/A |
| 3 | Atherosclerosis, Obesity (AO) | Cancer, Immunology, Metabolism |
| | Atherosclerosis, Obesity, T2DM/IR (AOD) | Cancer, Immunology, Metabolism |
| | NAFLD (N) | Cancer, Development, Metabolism |
| | NAFLD, Obesity, T2DM/IR (NOD) | Arthritis, Immunology, Metabolism |
| | Obesity (O) | Cancer, Immunology, Proliferation/survival |
| 4 | Atherosclerosis, T2DM/IR (AD) | Cancer, Development, Immunology, Proliferation/survival |
| | Atherosclerosis, NAFLD, T2DM/IR (AND) | Cancer, Immunology, Metabolism, Proliferation/survival |
| | T2DM/IR (D) | Arthritis, Cancer, Metabolism, Proliferation/survival |
| | NAFLD, T2DM/IR (ND) | Cancer, Immunology, Metabolism, Proliferation/survival |
| 5 | Atherosclerosis (A) | Cancer, Development, Immunology, Metabolism, Proliferation/survival |
| | Atherosclerosis, NAFLD (AN) | Arthritis, Cancer, Immunology, Metabolism, Proliferation/survival |
| | Obesity, T2DM/IR (OD) | Arthritis, Cancer, Development, Immunology, Proliferation/survival |

Fig. 6I

| Health State | Upregulated Pathways |
|---|---|
| Atherosclerosis | Complement System + Airway Pathology in Chronic Obstructive Pulmonary Disease + NAD biosynthesis II (from tryptophan) + Tryptophan Degradation III (Eukaryotic) + TREM1 Signaling + Role of IL-17A in Psoriasis + Caveolar-mediated Endocytosis Signaling |
| Cancer | Intrinsic Prothrombin Activation Pathway + IL-17A Signaling in Gastric Cells + Colorectal Cancer Metastasis Signaling + 4-aminobutyrate Degradation I + Melatonin Degradation II + Arginine Degradation I (Arginase Pathway) + Glutamate Degradation III (via 4-aminobutyrate) + Urea Cycle + Arginine Degradation VI (Arginase 2 Pathway) + Citrulline Biosynthesis |
| MHO | EIF2 Signaling + Asparagine Biosynthesis I + Creatine-phosphate Biosynthesis + Tetrahydrofolate Salvage from 5,10-methenyltetrahydrofolate + Histidine Degradation III + Folate Transformations I + IL-12 Signaling and Production in Macrophages + CDP-diacylglycerol Biosynthesis I |
| NAFLD | Epoxysqualene Biosynthesis + Molecular Mechanisms of Cancer + tRNA Splicing + nNOS Signaling in Neurons + Glutamate Receptor Signaling + PCP pathway + Sphingomyelin Metabolism + Basal Cell Carcinoma Signaling + Role of IL-17A in Arthritis + Melatonin Signaling + Role of Wnt/GSK-3β Signaling in the Pathogenesis of Influenza + Ephrin Receptor Signaling |
| Obesity | Hepatic Fibrosis / Hepatic Stellate Cell Activation + Systemic Lupus Erythematosus Signaling + IL-6 Signaling + Dendritic Cell Maturation + B Cell Development + Glioma Invasiveness Signaling + Osteoarthritis Pathway + Role of Macrophages, Fibroblasts and Endothelial Cells in Rheumatoid Arthritis + Hepatic Cholestasis + NF-κB Signaling + Natural Killer Cell Signaling + Role of Tissue Factor in Cancer |
| T2DM | Chondroitin Sulfate Degradation (Metazoa) + IL-22 Signaling + iCOS-iCOSL Signaling in T Helper Cells + Heme Biosynthesis from Uroporphyrinogen-III I + Cancer Drug Resistance By Drug Efflux + Trehalose Degradation II (Trehalase) + Insulin Receptor Signaling + Melanoma Signaling + Endometrial Cancer Signaling + Heme Biosynthesis II + GDP-glucose Biosynthesis + Glucose and Glucose-1-phosphate Degradation + Oleate Biosynthesis II (Animals) + IL-17A Signaling in Airway Cells + UDP-N-acetyl-D-galactosamine Biosynthesis II |
| Atherosclerosis + Cancer | Tryptophan Degradation to 2-amino-3-carboxymuconate Semialdehyde + Inhibition of Matrix Metalloproteases + Leukocyte Extravasation Signaling + Bladder Cancer Signaling + HIF1α Signaling |
| Atherosclerosis + Obesity | Hematopoiesis from Pluripotent Stem Cells + Communication between Innate and Adaptive Immune Cells + Role of Hypercytokinemia/hyperchemokinemia in the Pathogenesis of Influenza + Primary Immunodeficiency Signaling + IL-8 Signaling + Phagosome Formation + IL-10 Signaling |
| Atherosclerosis + T2DM | Neuroprotective Role of THOP1 in Alzheimer's Disease |
| Cancer + MHO | FXR/RXR Activation + Serine Biosynthesis + Superpathway of Serine and Glycine Biosynthesis I |
| Cancer + Obesity | GP6 Signaling Pathway |
| MHO + T2DM | Regulation of eIF4 and p70S6K Signaling |
| Obesity + T2DM | Acute Phase Response Signaling |
| Atherosclerosis + Cancer + Obesity | Granulocyte Adhesion and Diapedesis + Agranulocyte Adhesion and Diapedesis |
| Atherosclerosis + MHO + Obesity | LXR/RXR Activation |
| Atherosclerosis + Cancer + MHO + Obesity | Atherosclerosis Signaling |
| Atherosclerosis + Cancer + MHO + T2DM | Pathogenesis of Multiple Sclerosis |

Fig. 7B

Scenario A
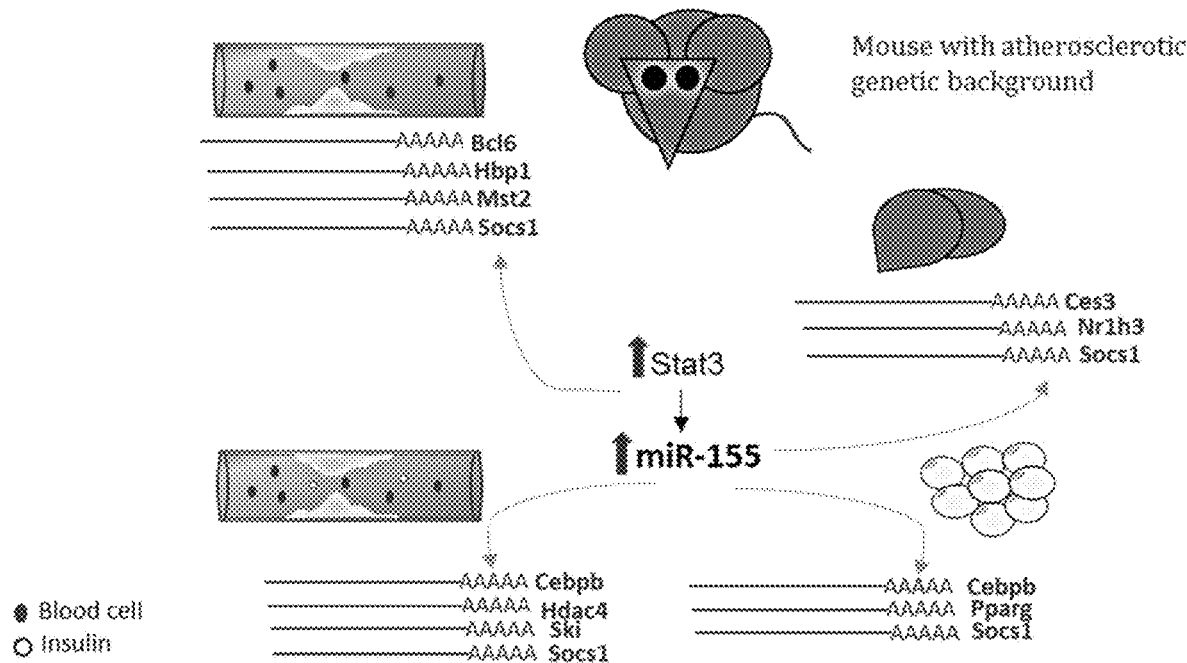
Scenario B
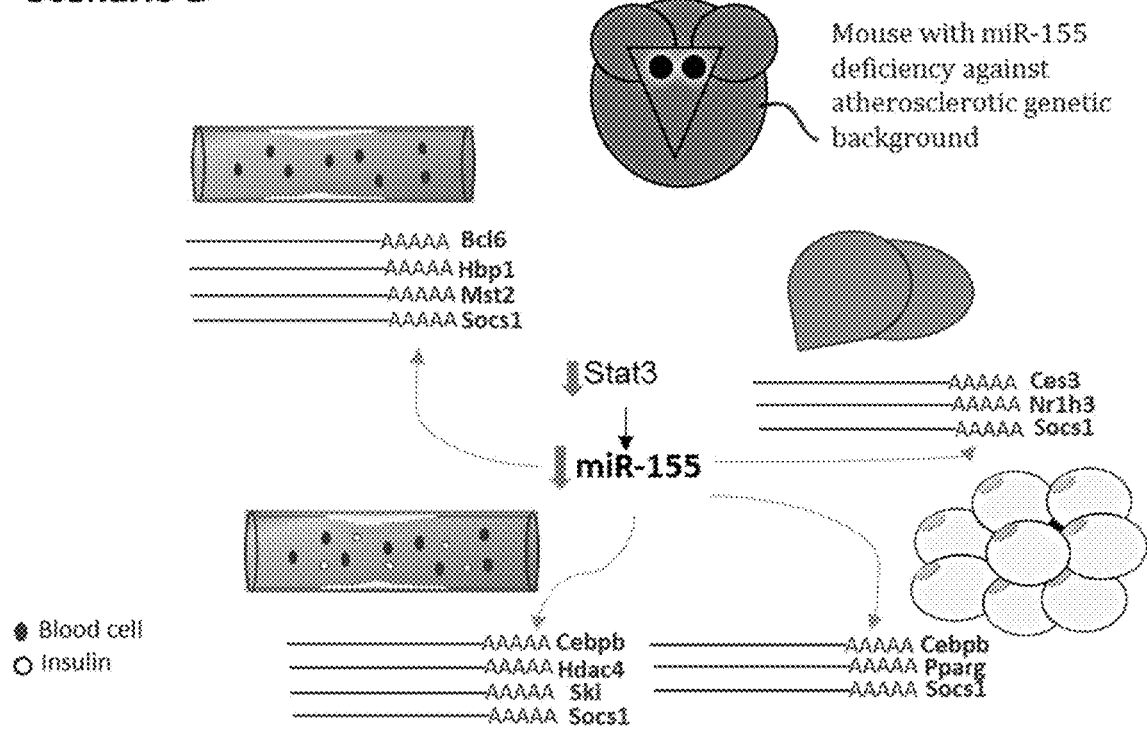
Fig. 8B

COMPOSITIONS AND METHODS FOR DIAGNOSING AND TREATING HYPERLIPIDEMIA-RELATED DISEASES

CROSS REFERENCE TO RELATED APPLICATIONS

This application claims priority to U.S. Provisional Application No. 62/674,088, filed May 21, 2018 which is hereby incorporated by reference herein in its entirety.

STATEMENT REGARDING FEDERALLY SPONSORED RESEARCH OR DEVELOPMENT

This invention was made with government support under HL138749-01 awarded by the National Institutes of Health. The government has certain rights in the invention.

BACKGROUND OF THE INVENTION

Hyperlipidemia, or high low-density lipoprotein cholesterol, is a condition affecting 78 million Americans and is a well-documented risk factor for a number of co-morbidities. These include atherosclerosis, obesity, non-alcoholic fatty liver disease (NAFLD) and type II diabetes mellitus (T2DM) (FIG. 1). Currently, the molecular mechanisms involved in the manifestation and progression of hyperlipidemia, particularly with respect to these co-morbidities, are not completely understood. MicroRNAs (miRNAs) are short (19-25 nucleotides), non-coding regulatory RNAs that regulate gene expression by mRNA translation inhibition or degradation (Virtue, A. et al., 2012, Journal of Hematology & Oncology, 5:66). In recent years, miRNAs have been firmly established as important regulators in a host of diseases, including cardiovascular disease, obesity, type II diabetes and NAFLD. Still, much remains to be understood regarding their overlap and function in hyperlipidemia-related pathologies. Over the years, multiple publications have shown the key roles that miRNAs play in these diseases. For example, it was reported that a group of anti-atherogenic miRNAs may downregulate pro-atherogenic genes (Virtue, A. et al., 2011, Front Biosci, 16:3133-3145). Soh et al. published their findings that miR-30c reduced atherosclerosis and hyperlipidemia in Western diet-fed mice (Soh, J. et al., 2013, Nat Med, 19(7):892-900). Hanin et al. found that transgenic miR-132-overexpressing mice resulted in fatty liver and hyperlipidemia (Hanin, G. et al., 2017, Gut, gutjnl-2016-312869). Vinnikov et al. showed that miR-103 secreted from the hypothalamus plays a role in preventing food-induced obesity (Vinnikov, I. A. et al., 2014, Journal of Neurosience, 34(32):10659-10674). Latreille et al. reported that overexpression of miR-7a in pancreatic beta cells led to type II diabetes development (Latreille, M. et al., 2014, Journal of Clinical Investigation, 124(6):2722-35). Additionally, it was demonstrated that miRNA-155 is significantly increased in atherosclerosis but reduced in high-fat diet-induced obesity. It was further presented that the novel findings that global miR-155 deficiency in an atherosclerotic ApoE$^{-/-}$ mouse background reduced atherosclerosis but resulted in obesity, NAFLD, and hyperglycemia without insulin resistance. These findings demonstrate a suitable model for study of metabolically healthy obesity. Such a finding implied that a metabolically healthy obesity (MHO) regulator must have the following features that: 1) a potent role of a single miRNA differentially affects multiple hyperlipidemia-related diseases such that miRNAs achieve master gene status; and 2) differential expressions and functions of downstream targets of the miRNA in different cell types support the miRNA promotion of atherosclerosis and vascular inflammation but suppression of white adipose tissue obesity.

Thus there is a need in the art, for methods for diagnosis of hyperlipidemia and co-morbidities and compositions for regulating hyperlipidemia disease-specific pathways. The present invention satisfies this unmet need.

SUMMARY OF THE INVENTION

In one embodiment, the invention relates to a method of diagnosing and treating a hyperlipidemia-related disease (HRD) in a subject comprising the steps of a) measuring the level of at least one miRNA in a biological sample from the subject; and b) comparing the level of the at least one miRNA in the biological sample from the subject to the level of the at least one miRNA in a comparator, wherein a difference between the level of the at least one miRNA in the biological sample from the subject and the level of the at least one miRNA in the comparator provides a diagnosis of a HRD.

In one embodiment, the HRD is at least one of atherosclerosis, non-alcoholic fatty liver disease (NAFLD), obesity or type 2 diabetes mellitus with insulin resistance (T2DM/IR).

In one embodiment, the method diagnoses atherosclerosis, and at least one miRNA in the biological sample from the subject is at least one of miR-880, miR-295, miR-302d, miR-291a, miR-744, miR-208, miR-712, miR-205, miR-200, miR-222, miR-210, let-7c, miR-19b, miR-92a, miR-29, miR-144, miR-34a, miR-126, miR-155, miR-342, miR-221, miR-21, miR-133, miR-101a, miR-10a, miR-145, miR-1, miR-181b, let-7g, miR-143, miR-199a, miR-26a, let-7b, miR-19a, miR-146a, and miR-335.

In one embodiment, the level of the at least one miRNA in the biological sample from the subject is increased compared to the level of the at least one miRNA in the comparator. In one embodiment, at least one miRNA is miR-880, miR-295, miR-302d, miR-291a, miR-744, miR-208, miR-712, miR-205, miR-200, miR-222, miR-210, let-7c, miR-19b, miR092a, miR-29, miR-144, miR-34a, miR-126, miR-155, miR-342, miR-221, or miR-21.

In one embodiment, the level of the at least one miRNA in the biological sample from the subject is decreased compared to the level of the at least one miRNA in the comparator. In one embodiment, at least one miRNA is miR-133, miR-101a, miR-10a, miR-145, miR-1, miR-181b, let-7g, miR-143, miR-199a, miR-26a, let-7b, miR-19a, miR-146a, or miR-335.

In one embodiment, the method diagnoses T2DM/IR. In one embodiment, at least one miRNA in the biological sample from the subject is miR-320a, miR-376a, miR-140, miR-107, miR-212, miR-499, miR-375, miR-589, miR-15b, miR-106b, miR-185, let-7f, miR-144, miR-34a, miR-16, miR-26b, miR-18a, miR-29, miR-146b, miR-221, miR-143, miR-199a, miR-374b, miR-20b, miR-381, miR-487b, miR-203, miR-301a, miR-129, miR-331, miR-486, miR-15a, miR-98, miR-152, miR-190, miR-133, miR-135b, miR-100, miR-99a, miR-155, let-7b, miR-30, miR-126 or miR-342.

In one embodiment, the level of the at least one miRNA in the biological sample from the subject is increased compared to the level of the at least one miRNA in the comparator. In one embodiment, at least one miRNA is miR-320a, miR-376a, miR-140, miR-107, miR-212, miR-499, miR-375, miR-589, miR-15b, miR-106b, miR-185, let-7f, miR-144, miR-34a, miR-16, miR-26b, miR-18a, miR-29, miR-146b, miR-221, miR-143 and miR-199a.

In one embodiment, the level of the at least one miRNA in the biological sample from the subject is decreased compared to the level of the at least one miRNA in the comparator. In one embodiment, at least one miRNA is miR-374b, miR-20b, miR-381, miR-487b, miR-203, miR-301a, miR-129, miR-331, miR-486, miR-15a, miR-98, miR-152, miR-190, miR-133, miR-135b, miR-100, miR-99a, miR-155, let-7b, miR-30, miR-126 or miR-342.

In one embodiment, the method diagnoses NAFLD. In one embodiment, at least one miRNA in the biological sample from the subject is miR-181d, miR-132, miR-150, miR-511, miR-671, miR-433, miR-128, miR-451, miR-99b, miR-28, miR-517a, let-7d, miR-155, miR-21, miR-99a, miR-370, miR-224, miR-31, miR-22, miR-10b, miR-429, miR-181a, miR-33, miR-200, miR-222, miR-146b, miR-34a, miR-16, miR-221, let-7b, or miR-26a.

In one embodiment, the level of the at least one miRNA in the biological sample from the subject is increased compared to the level of the at least one miRNA in the comparator. In one embodiment, at least one miRNA is miR-370, miR-224, miR-31, miR-22, miR-10b, miR-429, miR-181a, miR-33, miR-200, miR-222, miR-146b, miR-34a, miR-16, miR-221, let-7b or miR-26a.

In one embodiment, the level of the at least one miRNA in the biological sample from the subject is decreased compared to the level of the at least one miRNA in the comparator. In one embodiment, at least one miRNA is miR-181d, miR-132, miR-150, miR-511, miR-671, miR-433, miR-128, miR-451, miR-99b, miR-28, miR-517a, let-7d, miR-155, miR-21 or miR-99a.

In one embodiment, the method diagnoses obesity. In one embodiment, at least one miRNA in the biological sample from the subject is miR-155, miR-221, miR-503, miR-27, miR-493, miR-136, miR-654, miR-758, miR-432, miR-1275, miR-193b-365, miR-135b, miR-100, miR-17, miR-20a, miR-378, miR-519d, miR-355, miR-148a, miR-1247, miR-3124, miR-1343, miR-191, miR-30, miR-21, miR-19a, miR-146a, miR-26b, miR-18a, miR-210, miR-19b, miR-92a, miR-29, miR-146b, let-7c or miR-335.

In one embodiment, the level of the at least one miRNA in the biological sample from the subject is increased compared to the level of the at least one miRNA in the comparator. In one embodiment, at least one miRNA is miR-17, miR-20a, miR-378, miR-519d, miR-355, miR-148a, miR-1247, miR-3124, miR-1343, miR-191, miR-30, miR-21, miR-19a, miR-146a, miR-26b, miR-18a, miR-210, miR-19b, miR-92a, miR-29, miR-146b, let-7c or miR-335.

In one embodiment, the level of the at least one miRNA in the biological sample from the subject is decreased compared to the level of the at least one miRNA in the comparator. In one embodiment, at least one miRNA is miR-155, miR-221, miR-503, miR-27, miR-493, miR-136, miR-654, miR-758, miR-432, miR-1275, miR-193b-365, miR-135b, or miR-100.

In one embodiment, the subject is human.

In one embodiment, the biological sample is blood, serum, plasma, or any combination thereof.

In one embodiment, the method of measuring the level of the at least one miRNA in the biological sample from the subject comprises next-generation sequencing, reverse transcription, polymerase chain reaction (PCR), or microarray analysis.

In one embodiment, the comparator is a positive control, a negative control, a normal control, a wild-type control, a historical control, or a historical norm.

In one embodiment, the method further comprises administering a treatment for the HRD.

In one embodiment, the invention relates to a method of monitoring efficacy of a treatment for a HRD in a subject, the method comprising the steps of a) treating the subject for a HRD; b) measuring the level of at least one miRNA in a biological sample from the subject; and c) comparing the level of the at least one miRNA in the biological sample from the subject to the level of the at least one miRNA in a comparator, wherein a difference between the level of the at least one miRNA in the biological sample from the subject and the level of the at least one miRNA in the comparator indicates that the treatment has efficacy in treating the HRD.

In one embodiment, the HRD is at least one of atherosclerosis, NAFLD, obesity and T2DM/IR.

In one embodiment, the method monitors the efficacy of a treatment for atherosclerosis. In one embodiment, at least one miRNA in the biological sample from the subject is miR-880, miR-295, miR-302d, miR-291a, miR-744, miR-208, miR-712, miR-205, miR-200, miR-222, miR-210, let-7c, miR-19b, miR-92a, miR-29, miR-144, miR-34a, miR-126, miR-155, miR-342, miR-221, miR-21, miR-133, miR-101a, miR-10a, miR-145, miR-1, miR-181b, let-7g, miR-143, miR-199a, miR-26a, let-7b, miR-19a, miR-146a, or miR-335.

In one embodiment, the level of the at least one miRNA in the biological sample from the subject is increased compared to the level of the at least one miRNA in the comparator. In one embodiment, at least one miRNA is miR-133, miR-101a, miR-10a, miR-145, miR-1, miR-181b, let-7g, miR-143, miR-199a, miR-26a, let-7b, miR-19a, miR-146a, or miR-335.

In one embodiment, the level of the at least one miRNA in the biological sample from the subject is decreased compared to the level of the at least one miRNA in the comparator. In one embodiment, at least one miRNA is miR-880, miR-295, miR-302d, miR-291a, miR-744, miR-208, miR-712, miR-205, miR-200, miR-222, miR-210, let-7c, miR-19b, miR092a, miR-29, miR-144, miR-34a, miR-126, miR-155, miR-342, miR-221, or miR-21.

In one embodiment, the method monitors the efficacy of a treatment for T2DM/IR. In one embodiment, at least one miRNA in the biological sample from the subject is miR-320a, miR-376a, miR-140, miR-107, miR-212, miR-499, miR-375, miR-589, miR-15b, miR-106b, miR-185, let-7f, miR-144, miR-34a, miR-16, miR-26b, miR-18a, miR-29, miR-146b, miR-221, miR-143, miR-199a, miR-374b, miR-20b, miR-381, miR-487b, miR-203, miR-301a, miR-129, miR-331, miR-486, miR-15a, miR-98, miR-152, miR-190, miR-133, miR-135b, miR-100, miR-99a, miR-155, let-7b, miR-30, miR-126 or miR-342.

In one embodiment, the level of the at least one miRNA in the biological sample from the subject is increased compared to the level of the at least one miRNA in the comparator. In one embodiment, at least one miRNA is miR-374b, miR-20b, miR-381, miR-487b, miR-203, miR-301a, miR-129, miR-331, miR-486, miR-15a, miR-98, miR-152, miR-190, miR-133, miR-135b, miR-100, miR-99a, miR-155, let-7b, miR-30, miR-126 or miR-342.

In one embodiment, the level of the at least one miRNA in the biological sample from the subject is decreased compared to the level of the at least one miRNA in the comparator. In one embodiment, at least one miRNA is miR-320a, miR-376a, miR-140, miR-107, miR-212, miR-499, miR-375, miR-589, miR-15b, miR-106b, miR-185, let-7f, miR-144, miR-34a, miR-16, miR-26b, miR-18a, miR-29, miR-146b, miR-221, miR-143 or miR-199a.

In one embodiment, the method monitors the efficacy of a treatment for NAFLD. In one embodiment, at least one miRNA in the biological sample from the subject is miR-181d, miR-132, miR-150, miR-511, miR-671, miR-433, miR-128, miR-451, miR-99b, miR-28, miR-517a, let-7d, miR-155, miR-21, miR-99a, miR-370, miR-224, miR-31, miR-22, miR-10b, miR-429, miR-181a, miR-33, miR-200, miR-222, miR-146b, miR-34a, miR-16, miR-221, let-7b, or miR-26a.

In one embodiment, the level of the at least one miRNA in the biological sample from the subject is increased compared to the level of the at least one miRNA in the comparator. In one embodiment, at least one miRNA is miR-181d, miR-132, miR-150, miR-511, miR-671, miR-433, miR-128, miR-451, miR-99b, miR-28, miR-517a, let-7d, miR-155, miR-21 or miR-99a.

In one embodiment, the level of the at least one miRNA in the biological sample from the subject is decreased compared to the level of the at least one miRNA in the comparator. In one embodiment, at least one miRNA is miR-370, miR-224, miR-31, miR-22, miR-10b, miR-429, miR-181a, miR-33, miR-200, miR-222, miR-146b, miR-34a, miR-16, miR-221, let-7b or miR-26a.

In one embodiment, the method monitors the efficacy of a treatment for obesity. In one embodiment, at least one miRNA in the biological sample from the subject is miR-155, miR-221, miR-503, miR-27, miR-493, miR-136, miR-654, miR-758, miR-432, miR-1275, miR-193b-365, miR-135b, miR-100, miR-17, miR-20a, miR-378, miR-519d, miR-355, miR-148a, miR-1247, miR-3124, miR-1343, miR-191, miR-30, miR-21, miR-19a, miR-146a, miR-26b, miR-18a, miR-210, miR-19b, miR-92a, miR-29, miR-146b, let-7c or miR-335.

In one embodiment, the level of the at least one miRNA in the biological sample from the subject is increased compared to the level of the at least one miRNA in the comparator. In one embodiment, at least one miRNA is miR-155, miR-221, miR-503, miR-27, miR-493, miR-136, miR-654, miR-758, miR-432, miR-1275, miR-193b-365, miR-135b, or miR-100.

In one embodiment, the level of the at least one miRNA in the biological sample from the subject is decreased compared to the level of the at least one miRNA in the comparator. In one embodiment, at least one miRNA is miR-17, miR-20a, miR-378, miR-519d, miR-355, miR-148a, miR-1247, miR-3124, miR-1343, miR-191, miR-30, miR-21, miR-19a, miR-146a, miR-26b, miR-18a, miR-210, miR-19b, miR-92a, miR-29, miR-146b, let-7c or miR-335.

In one embodiment, the subject is human.

In one embodiment, the biological sample is blood, serum, plasma, or any combination thereof.

In one embodiment, the method of measuring the level of the at least one miRNA in the biological sample from the subject comprises reverse transcription, polymerase chain reaction (PCR), or microarray analysis.

In one embodiment, the comparator is a sample from a diseased subject not receiving treatment, a sample from the subject obtained at an earlier time point during treatment, a sample from the subject obtained prior to treatment or a level in a population of diseased subjects not receiving treatment.

In one embodiment, the invention relates to a method of treating or preventing HRD or a HRD associated disease in a subject in need thereof comprising modulating at least one miRNA in the subject. In one embodiment, at least one miRNA is miR-320a, miR-376a, miR-140, miR-107, miR-212, miR-499, miR-375, miR-589, miR-15b, miR-106b, miR-185, let-7f, miR-144, miR-34a, miR-16, miR-26b, miR-18a, miR-29, miR-146b, miR-221, miR-143, miR-199a, miR-374b, miR-20b, miR-381, miR-487b, miR-203, miR-301a, miR-129, miR-331, miR-486, miR-15a, miR-98, miR-152, miR-190, miR-133, miR-135b, miR-100, miR-99a, miR-155, let-7b, miR-30, miR-126, miR-342, miR-181d, miR-132, miR-150, miR-511, miR-671, miR-433, miR-128, miR-451, miR-99b, miR-28, miR-517a, let-7d, miR-370, miR-224, miR-31, miR-22, miR-10b, miR-429, miR-181a, miR-33, miR-200, miR-222, miR-21, miR-26a, miR-503, miR-27, miR-493, miR-136, miR-654, miR-758, miR-432, miR-1275, miR-193b-365, miR-17, miR-20a, miR-378, miR-519d, miR-355, miR-148a, miR-1247, miR-3124, miR-1343, miR-191, miR-210, miR-19b, miR-92a, let-7c, miR-335, miR-19a, miR-146a, miR-880, miR-295, miR-302d, miR-291a, miR-744, miR-208, miR-712, miR-205, miR-101a, miR-10a, miR-145, miR-1, miR-181b, or let-7g.

In one embodiment, the HRD or HRD associated disease is at least one of obesity, diabetes mellitus, NAFLD, liver cirrhosis, atherosclerosis, and cancer.

In one embodiment, the method of modulating at least one miRNA comprises administering to the subject a composition comprising at least one of an antisense nucleic acid, an antagomir, a ribozyme, a nucleic acid, a polypeptide, an antibody, or a small molecule.

In one embodiment, the invention relates to a method of differentially diagnosing a subject as having a HRD, the method comprising measuring the level of at least one of miR-320a, miR-376a, miR-140, miR-107, miR-212, miR-499, miR-375, miR-589, miR-15b, miR-106b, miR-185, let-7f, miR-144, miR-34a, miR-16, miR-26b, miR-18a, miR-29, miR-146b, miR-221, miR-143, miR-199a, miR-374b, miR-20b, miR-381, miR-487b, miR-203, miR-301a, miR-129, miR-331, miR-486, miR-15a, miR-98, miR-152, miR-190, miR-133, miR-135b, miR-100, miR-99a, miR-155, let-7b, miR-30, miR-126, miR-342, miR-181d, miR-132, miR-150, miR-511, miR-671, miR-433, miR-128, miR-451, miR-99b, miR-28, miR-517a, let-7d, miR-370, miR-224, miR-31, miR-22, miR-10b, miR-429, miR-181a, miR-33, miR-200, miR-222, miR-21, miR-26a, miR-503, miR-27, miR-493, miR-136, miR-654, miR-758, miR-432, miR-1275, miR-193b-365, miR-17, miR-20a, miR-378, miR-519d, miR-355, miR-148a, miR-1247, miR-3124, miR-1343, miR-191, miR-210, miR-19b, miR-92a, let-7c, miR-335, miR-19a, miR-146a, miR-880, miR-295, miR-302d, miR-291a, miR-744, miR-208, miR-712, miR-205, miR-101a, miR-10a, miR-145, miR-1, miR-181b, or let-7g miRNA in a biological sample from the subject, and comparing the level of the at least one miRNA in the biological sample from the subject to the level of the at least one miRNA in a comparator. In one embodiment, a difference between the level of the at least one miRNA in the biological sample from the subject and the level of the at least one miRNA in the comparator provides a differential diagnosis of a HRD.

In one embodiment, the HRD is metabolically healthy obesity type I, metabolically healthy obesity type II, obesity, T2DM/IR, NAFLD, or atherosclerosis.

In one embodiment, the invention relates to a method of diagnosing a subject as having co-morbid HRDs comprising measuring the level of at least one of miR-320a, miR-376a, miR-140, miR-107, miR-212, miR-499, miR-375, miR-589, miR-15b, miR-106b, miR-185, let-7f, miR-144, miR-34a, miR-16, miR-26b, miR-18a, miR-29, miR-146b, miR-221, miR-143, miR-199a, miR-374b, miR-20b, miR-381, miR-487b, miR-203, miR-301a, miR-129, miR-331, miR-486, miR-15a, miR-98, miR-152, miR-190, miR-133, miR-135b, miR-100, miR-99a, miR-155, let-7b, miR-30, miR-126, miR-342, miR-181d, miR-132, miR-150, miR-511, miR-671, miR-433, miR-128, miR-451, miR-99b, miR-28, miR-517a, let-7d, miR-370, miR-224, miR-31, miR-22, miR-10b, miR-429, miR-181a, miR-33, miR-200, miR-222, miR-21, miR-26a, miR-503, miR-27, miR-493, miR-136, miR-654, miR-758, miR-432, miR-1275, miR-193b-365, miR-17, miR-20a, miR-378, miR-519d, miR-355, miR-148a, miR-1247, miR-3124, miR-1343, miR-191, miR-210, miR-19b, miR-92a, let-7c, miR-335, miR-19a, miR-146a, miR-880, miR-295, miR-302d, miR-291a, miR-744, miR-208, miR-712, miR-205, miR-101a, miR-10a, miR-145, miR-1, miR-181b, and let-7g in a biological sample of a subject, and comparing the level of the at least one miRNA in the biological sample from the subject to the level of the at least one miRNA in a comparator. In one embodiment, a difference between the level of the at least one miRNA in the biological sample from the subject and the level of the at least one miRNA in the comparator provides a differential diagnosis of co-morbid HRDs. In one embodiment, the co-morbid HRD comprises at least two of obesity, T2DM/IR, NAFLD, and atherosclerosis.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1A through FIG. 1E depict flow charts of the database mining strategy. FIG. 1A depicts select inflammatory metabolic diseases demonstrating a close relationship due to shared hyperlipidemia and inflammation characteristics (in bold).

FIG. 1B depicts mining strategy to identify miRNAs modulated in hyperlipidemic-related diseases. FIG. 1C depicts the mining strategy to identify upstream miRNA-regulating transcription factors. FIG. 1D depicts the mining strategy to identify miR-155 and miR-221 downstream targets in the four hyperlipidemia-related diseases. FIG. 1E depicts the mining strategy to identify pathways in the four hyperlipidemia-related diseases, MHO, and cancer.

FIG. 2A through FIG. 2C depict the results of example experiment demonstrating that hyperlipidemic diseases-shared miRs are much less than disease specific miRs. FIG. 2A depicts a Venn diagram of the miRNA expression profile of hyperlipidemia-related diseases. FIG. 2B depicts that thirty hyperlipidemic disease-related miRNAs are shared between diseases and are differentially expressed. FIG. 2C depicts that differentially expressed miRNAs may serve as biomarkers for hyperlipidemia-related single and co-morbid diseases.

FIG. 3A through FIG. 3B depict the results of example experiment demonstrating that three transcription factors EGR1, NFκB and STAT3 regulate miRNAs related to all four hyperlipidemia-related diseases. FIG. 3A depicts that STAT3 and EGR1 are positive regulators of single-disease miRNAs in all four diseases. FIG. 3B depicts that transcription factors, STAT3 and NFκB, commonly regulate miR-221 and miR-155.

FIG. 4A through FIG. 4B depict the results of example experiments demonstrating that of 11 miR-221 mRNA targets that have been experimentally verified in any of the four hyperlipidemia-related disease backgrounds, PTEN and ETS1 mRNA are negatively regulated in three out of four hyperlipidemia-related diseases. FIG. 4A depicts that out of 82 mRNA targets of miR-221, eleven are experimentally verified in the four hyperlipidemia-related diseases. FIG. 4B depicts experimental evidence showing that PTEN and ETS1 mRNAs are negatively regulated by miR-221 in three out of four hyperlipidemia-related diseases.

FIG. 5A through FIG. 5B depict the results of example experiments demonstrating that, of 20 miR-155 mRNA targets that have been experimentally verified in any of the four hyperlipidemia-related disease backgrounds, only Socs1 mRNA is shown to be negatively regulated by miR-155 in all four disease contexts. FIG. 5A depicts that out of 176 mRNA targets of miR-155, twenty are experimentally verified in the four hyperlipidemia-related diseases. FIG. 5B depicts experimental evidence showing that Socs1 mRNA is negatively regulated by miR-155 in all four hyperlipidemia-related diseases.

FIG. 6A through FIG. 6I depict pathway analyses of miRNA-regulating transcription factors showing that unique and shared disease groups have six modulated pathways in cancer, metabolism, immunology, arthritis, proliferation/survival, development, which imply hyperlipidemia-related diseases' roles of miRNA-regulating transcription factors. FIG. 6A depicts that 12 cancer pathway subsets are modulated 55 times in unique and shared diseases. FIG. 6B depicts that 10 proliferation/survival pathway subsets are modulated 13 times in unique and shared diseases. FIG. 6C depicts that 8 arthritis pathway subsets are modulated 7 times in unique and shared diseases. FIG. 6D depicts that developmental pathway subsets are modulated 5 times in unique and shared diseases. FIG. 6E depicts that metabolism pathway subsets are modulated 14 times in unique and shared diseases. FIG. 6F depicts that immunology pathway subsets are modulated 13 times in unique and shared diseases. FIG. 6G depicts that cancer is the most commonly-modulated pathway among four hyperlipidemic diseases. FIG. 6H depicts that atherosclerosis-NAFLD have the most upregulated pathways. FIG. 6I depicts that atherosclerosis-NAFLD and obesity-diabetes disease conditions have the most significantly modulated pathways.

FIG. 7A through FIG. 7B depict the results of example experiments demonstrating top pathways in hyperlipidemia-related diseases. MHO, and cancer show multiple shared pathways. FIG. 7A depicts that various pathways are shared between hyperlipidemia-related diseases, metabolically healthy obesity (MHO), and cancer. FIG. 7B depicts that atherosclerosis signaling and pathogenesis of multiple sclerosis pathways link three disease conditions and metabolically healthy obesity (MHO) together.

FIG. 8A through FIG. 8C depict schematic diagrams demonstrating STAT3 and NFκB may be critical mediators of the hyperlipidemia-related pathologies of atherosclerosis, NAFLD, obesity and type II diabetes/insulin resistance via miR-155 transcriptional levels, which then target varied protein-encoding mRNA levels in tissues to create different and opposing phenotypes in different tissues. FIG. 8A depicts a diagram showing that the levels of miR-155 play a role in maintaining the balance between risk of different HRDs. Scenario A indicates that increased miR-155 levels are associated with atherosclerosis. Scenario B indicates that decreased miR-155 levels are associated with obesity, NAFLD and hyperinsulinemia. FIG. 8B depicts a schematic diagram showing the effects of different miR-155 transcriptional levels. Scenario A depicts atherosclerotic apoE-deficient mice present with atherosclerosis in an otherwise normal phenotype in liver, adipose tissue and circulating insulin levels. Scenario B depicts that miR155 deficiency in atherosclerotic apoE-knockout mice display reduced atherosclerosis despite obesity, non-alcoholic fatty liver disease, and hyperinsulinemia. FIG. 8C depicts a schematic diagram showing MHO exists as subtypes. In the progression from healthy lean to the impermanent MHO to CO, miR-221 is first to be downregulated to create type I MHO, with features of obesity but no atherosclerosis, NAFLD, or T2DM/IR. Eventually, Type II MHO follows, which is due to miR-155 downregulation. This manifests as obesity with NAFLD and hyperinsulinemia, but no cardiovascular disease. Over time, MHO makes the transition to classically unhealthy obesity, which is characterized by cardiovascular disease, NAFLO, T2DM/IR, along with obesity. MHO, metabolically healthy obesity. Horizontal bar indicates that Type 2 diabetes/insulin Resistance is not achieved but due to hyperinsulinemia there is a trend in this direction.

DETAILED DESCRIPTION

Figure 1C:
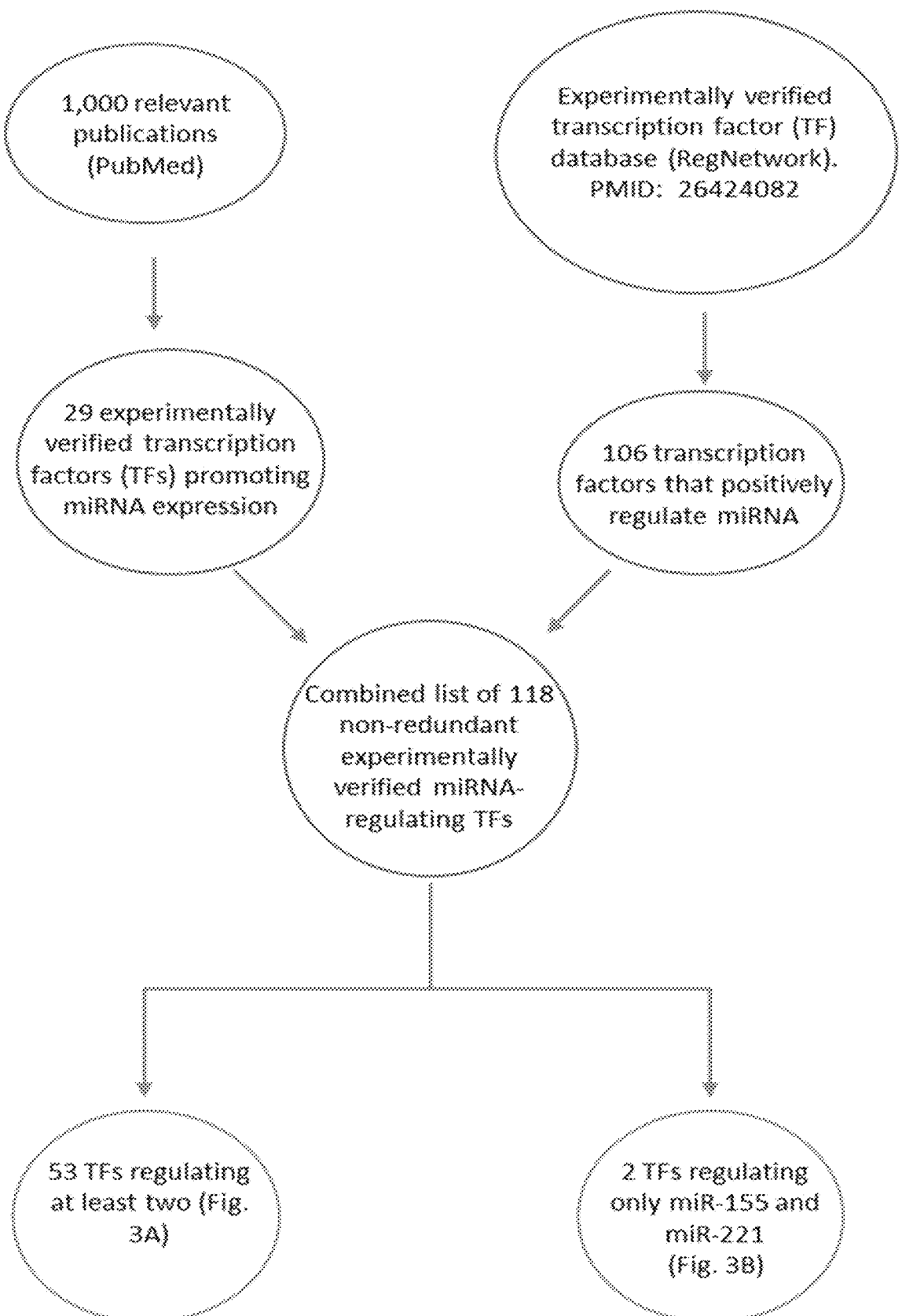

The present invention relates to the discovery that the expression level of particular miRNAs is associated with hyperlipidemia-related diseases (HRD), including atherosclerosis, non-alcoholic fatty liver disease (NAFLD), obesity and type 2 diabetes mellitus with insulin resistance (T2DM/IR). Thus, in various embodiments described herein, the methods of the invention relate to methods of diagnosing a subject as having a HRD, methods of assessing a subject's risk of having or developing a HRD, methods of assessing the severity of a subject's HRD, methods of stratifying a subject having a HRD for assignment in a clinical trial, methods of monitoring treatment of a HRD in a subject, and methods for treatment of a HRD in a subject. Thus, the invention relates to compositions and methods useful for the modulation, detection and quantification of miRNAs for the treatment, diagnosis, assessment, and characterization of a HRD in a subject in need thereof, based upon the expression level of at least one miRNA that is associated with a HRD. The markers of the invention can be used to screen, diagnose, monitor the onset, monitor the progression, and assess the treatment of a HRD. The markers of the invention can be used to establish and evaluate treatment plans.

In one embodiment, the miRNA that is associated with a HRD is a marker or biomarker of atherosclerosis. In various embodiments, the biomarkers of the invention comprise one or more of miR-880, miR-295, miR-302d, miR-291a, miR-744, miR-208, miR-712, miR-205, miR-200, miR-222, miR-210, let-7c, miR-19b, miR-92a, miR-29, miR-144, miR-34a, miR-126, miR-155, miR-342, miR-221, miR-21, miR-133, miR-101a, miR-10a, miR-145, miR-1, miR-181b, let-7g, miR-143, miR-199a, miR-26a, let-7b, miR-19a, miR-146a, and miR-335.

In one embodiment, the miRNA that is associated with a HRD is a marker or biomarker of T2DM/IR. In various embodiments, the biomarkers of the invention comprise one or more of miR-320a, miR-376a, miR-140, miR-107, miR-212, miR-499, miR-375, miR-589, miR-15b, miR-106b, miR-185, let-7f, miR-144, miR-34a, miR-16, miR-26b, miR-18a, miR-29, miR-146b, miR-221, miR-143, miR-199a, miR-374b, miR-20b, miR-381, miR-487b, miR-203, miR-301a, miR-129, miR-331, miR-486, miR-15a, miR-98, miR-152, miR-190, miR-133, miR-135b, miR-100, miR-99a, miR-155, let-7b, miR-30, miR-126 and miR-342.

In one embodiment, the miRNA that is associated with a HRD is a marker or biomarker of NAFLD. In various embodiments, the biomarkers of the invention comprise one or more of miR-181d, miR-132, miR-150, miR-511, miR-671, miR-433, miR-128, miR-451, miR-99b, miR-28, miR-517a, let-7d, miR-155, miR-21, miR-99a, miR-370, miR-224, miR-31, miR-22, miR-10b, miR-429, miR-181a, miR-33, miR-200, miR-222, miR-146b, miR-34a, miR-16, miR-221, let-7b, and miR-26a.

In one embodiment, the miRNA that is associated with a HRD is a marker or biomarker of obesity. In various embodiments, the biomarkers of the invention comprise one or more of miR-155, miR-221, miR-503, miR-27, miR-493, miR-136, miR-654, miR-758, miR-432, miR-1275, miR-193b-365, miR-135b, miR-100, miR-17, miR-20a, miR-378, miR-519d, miR-355, miR-148a, miR-1247, miR-3124, miR-1343, miR-191, miR-30, miR-21, miR-19a, miR-146a, miR-26b, miR-18a, miR-210, miR-19b, miR-92a, miR-29, miR-146b, let-7c and miR-335.

In one embodiment, the miRNA that is associated with a HRD is a marker or biomarker of metabolically healthy obesity type I. In various embodiments, the biomarker of metabolically healthy obesity type I comprises miR-221.

In one embodiment, the miRNA that is associated with a HRD is a marker or biomarker of metabolically healthy obesity type II. In various embodiments, the biomarkers of metabolically healthy obesity type II comprise miR-221 and miR-155.

In various embodiments, the biomarkers of the invention can be used to differentially diagnose a subject as having or at risk of atherosclerosis, NAFLD, obesity, metabolically healthy obesity type I, metabolically healthy obesity type II and T2DM/IR.

In various embodiments, the biomarkers of the invention can be used to diagnose a subject as having or at risk of co-morbid HRDs. In one embodiment, the biomarkers of the invention can be used to diagnose a subject as having or at risk of an atherosclerosis and T2DM/IR co-morbid condition, an atherosclerosis and obesity co-morbid condition, an atherosclerosis and NAFLD co-morbid condition, a T2DM/IR and obesity co-morbid condition, a NAFLD and T2DM/IR co-morbid condition, an atherosclerosis, obesity and T2DM/IR co-morbid condition, an atherosclerosis, NAFLD and T2DM/IR co-morbid condition or an atherosclerosis, NAFLD and T2DM/IR co-morbid condition.

In one embodiment, the invention provides a marker that predicts an individual's risk of developing a HRD. In one embodiment, the markers of the invention can predict risk at a time when a prophylactic therapy can be administered such that the emergence of the disease is prevented. In one embodiment, the invention provides a therapy for a HRD that modulates at least one miRNA associated with a HRD.

In one embodiment, the markers of the invention are noninvasive biomarkers for a HRD that allow for early detection of the disease. For example, altered expression of specific miRNAs in the biological sample of the subject with a HRD may correlate with other clinical parameters, such as the progression of obesity to diabetes. Therefore, the markers of the invention can be used, not only as biomarkers of the disease, but also as markers for prognosis and disease state.

The present invention provides biomarkers for the diagnosis and prognosis of a HRD. Generally, the methods of this invention find use in treating, diagnosing or for providing a prognosis for a HRD by modulating or detecting the expression levels of biomarkers, which are differentially expressed (up- or down-regulated) in blood, plasma, serum, or other biological fluid (e.g., cerebrospinal fluid (CSF), synovial fluid) from a patient. Similarly, these markers can provide a prognosis for a patient suffering from a HRD. The present invention also provides methods of identifying a compound for its ability to treat or prevent a HRD. The present invention also provides kits for the diagnosis or prognosis of a HRD.

Definitions

Unless defined otherwise, all technical and scientific terms used herein have the same meaning as commonly understood by one of ordinary skill in the art to which this invention belongs.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

The term "analog" as used herein generally refers to compounds that are generally structurally similar to the compound of which they are an analog, or "parent" compound. Generally, analogs will retain some characteristics of the parent compound, e.g., a biological or pharmacological activity. An analog may lack other, less desirable characteristics, e.g., antigenicity, proteolytic instability, toxicity, and the like. An analog includes compounds in which a particular biological activity of the parent is reduced, while one or more distinct biological activities of the parent are unaffected in the "analog." As applied to polypeptides, the term "analog" may have varying ranges of amino acid sequence identity to the parent compound, for example at least about 70%, at least about 80%-85%, at least about 86%-89%, at least about 90%, at least about 92%, at least about 94%, at least about 96%, at least about 98% or at least about 99% of the amino acids in a given amino acid sequence of the parent or a selected portion or domain of the parent. As applied to polypeptides, the term "analog" generally refers to polypeptides which are comprised of a segment of about at least 3 amino acids that has substantial identity to at least a portion of a binding domain fusion protein. Analogs typically are at least 5 amino acids long, at least 20 amino acids long or longer, at least 50 amino acids long or longer, at least 100 amino acids long or longer, at least 150 amino acids long or longer, at least 200 amino acids long or longer, and more typically at least 250 amino acids long or longer. Some analogs may lack substantial biological activity but may still be employed for various uses, such as for raising antibodies to predetermined epitopes, as an immunological reagent to detect and/or purify reactive antibodies by affinity chromatography, or as a competitive or noncompetitive agonist, antagonist, or partial agonist of a binding domain fusion protein function. As applied to polynucleotides, the term "analog" may have varying ranges of nucleic acid sequence identity to the parent compound, for example at least about 70%, at least about 80%-85%, at least about 86%-89%, at least about 90%, at least about 92%, at least about 94%, at least about 96%, at least about 98% or at least about 99% of the nucleic acids in a given nucleic acid sequence of the parent or a selected portion or domain of the parent. As applied to polynucleotides, the term "analog" generally refers to polynucleotides which are comprised of a segment of about at least 9 nucleic acids that has substantial identity to at least a portion of the parent. Analogs typically are at least 15 nucleic acids long, at least 60 nucleic acids long or longer, at least 150 nucleic acids long or longer, at least 300 nucleic acids long or longer, at least 450 nucleic acids long or longer, at least 600 nucleic acids long or longer, and more typically at least 750 nucleic acids long or longer. Some analogs may lack substantial biological activity but may still be employed for various uses, such as for encoding epitopes for raising antibodies to predetermined epitopes, as a reagent to detect and/or purify sequences by hybridization assays, or as a competitive or noncompetitive agonist, antagonist, or partial agonist of a target or modulator of a target.

A "MicroRNA recognition element" (MRE) refers to the recognition region in the mRNA transcript and is also referred to in the art as a miRNA response element. MREs are often degenerate sequences, and one miRNA can recognize MREs on more than one gene. This allows the ability to design high-affinity, high-specificity compounds that can distinguish between MREs of similar sequence.

An "antagomir" as used herein is a MRE-concealing oligonucleotide which may be conjugated to a chemical moiety to confer a function. In one example, the antagomir is an oligonucleotide molecule conjugated to a lipophilic moiety on the 3' end of the molecule, such as cholesterol. The term refers to a nucleic acid that is substantially complementary to a nucleotide sequence of one or more miRNAs. Antagomirs are useful for inhibiting or reducing the activity of one or more miRNAs, thereby increasing levels of the miRNA-targeted mRNA transcripts, for example, as part of a therapy for a HRD.

The term "antibody," as used herein, refers to an immunoglobulin molecule which is able to specifically bind to a specific epitope of a binding partner molecule. Antibodies can be intact immunoglobulins derived from natural sources, or from recombinant sources and can be immunoreactive portions of intact immunoglobulins. The antibodies in the present invention may exist in a variety of forms including, for example, polyclonal antibodies, monoclonal antibodies, intracellular antibodies ("intrabodies"), Fv, Fab, Fab', F(ab)2 and F(ab')2, as well as single chain antibodies (scFv), heavy chain antibodies, such as camelid antibodies, and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" or "binding fragment" refers to at least one portion of an antibody and refers to the antigenic determining variable regions of an intact antibody.

Examples of antibody fragments include, but are not limited to, Fab, Fab', F(ab')2, and Fv fragments, linear antibodies, sdAb (either VL or VH), camelid VHH domains, scFv antibodies, and multi-specific antibodies formed from antibody fragments. The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain polypeptide, and wherein the scFv retains the specificity of the intact antibody from which it was derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

An "antibody heavy chain," as used herein, refers to the larger of the two types of polypeptide chains present in antibody molecules in their naturally occurring conformations, and which normally determines the class to which the antibody belongs.

An "antibody light chain," as used herein, refers to the smaller of the two types of polypeptide chains present in antibody molecules in their naturally occurring conformations. Kappa (κ) and lambda (λ) light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

A "chimeric antibody" refers to a type of engineered antibody which contains a naturally-occurring variable region (light chain and heavy chains) derived from a donor antibody in association with light and heavy chain constant regions derived from an acceptor antibody.

A "humanized antibody" refers to a type of engineered antibody having its complementarity determining regions (CDRs) derived from a non-human donor immunoglobulin, the remaining immunoglobulin-derived parts of the molecule being derived from one (or more) human immunoglobulin(s). In addition, framework support residues may be altered to preserve binding affinity (see, e.g., 1989, Queen et al., Proc. Natl. Acad Sci USA, 86:10029-10032; 1991, Hodgson et al., Bio/Technology, 9:421). A suitable human acceptor antibody may be one selected from a conventional database, e.g., the KABAT database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanized antibodies (see for example EP-A-0239400 and EP-A-054951).

The term "donor antibody" refers to an antibody (monoclonal, and/or recombinant) which contributes the amino acid sequences of its variable regions, CDRs, or other functional fragments or analogs thereof to a first immunoglobulin partner, so as to provide the altered immunoglobulin coding region and resulting expressed altered antibody with the binding specificity and neutralizing activity characteristic of the donor antibody.

The term "acceptor antibody" refers to an antibody (monoclonal and/or recombinant) heterologous to the donor antibody, which contributes all (or any portion, but in some embodiments all) of the amino acid sequences encoding its heavy and/or light chain framework regions and/or its heavy and/or light chain constant regions to the first immunoglobulin partner. In some embodiments a human antibody is the acceptor antibody.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate). The structure and protein folding of the antibody may mean that other residues are considered part of the binding region and would be understood to be so by a skilled person. See for example Chothia et al., (1989) Conformations of immunoglobulin hypervariable regions; Nature 342, p 877-883.

The term "framework" or "framework sequence" refers to the remaining sequences of a variable region minus the CDRs. Because the exact definition of a CDR sequence may be determined by different systems, the meaning of a framework sequence is subject to correspondingly different interpretations. The six CDRs (CDR-L1, -L2, and -L3 of light chain and CDR-H1, -H2, and -H3 of heavy chain) also divide the framework regions (FR) on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. An FR represents one of the four sub-regions, and FRs represents two or more of the four sub-regions constituting a framework region.

"Antisense," or "antisense nucleic acid molecule," as used herein, refers to a nucleic acid comprising a sequence which is complementary to a target sequence, such as, by way of example, complementary to a target miRNA sequence, including, but not limited to, a mature target miRNA sequence, or a related sequence thereof. Typically, an antisense sequence is fully complementary to the target sequence across the full length of the antisense nucleic acid sequence.

The term "body fluid" or "bodily fluid" as used herein refers to any fluid from the body of an animal. Examples of body fluids include, but are not limited to, plasma, serum, blood, lymphatic fluid, cerebrospinal fluid, synovial fluid, urine, saliva, mucous, phlegm and sputum. A body fluid sample may be collected by any suitable method. The body fluid sample may be used immediately or may be stored for later use. Any suitable storage method known in the art may be used to store the body fluid sample: for example, the sample may be frozen at about −20° C. to about −70° C. Suitable body fluids are acellular fluids. "Acellular" fluids include body fluid samples in which cells are absent or are present in such low amounts that the miRNA level determined reflects its level in the liquid portion of the sample, rather than in the cellular portion. Such acellular body fluids are generally produced by processing a cell-containing body fluid by, for example, centrifugation or filtration, to remove the cells. Typically, an acellular body fluid contains no intact cells however, some may contain cell fragments or cellular debris. Examples of acellular fluids include plasma or serum, or body fluids from which cells have been removed.

The term "clinical factors" as used herein, refers to any data that a medical practitioner may consider in determining a diagnosis or prognosis of disease. Such factors include, but are not limited to, the patient's medical history, a physical examination of the patient, complete blood count, analysis of the activity of enzymes, examination of cells, cytogenetics, and immunophenotyping of blood cells.

"Complementary" as used herein refers to the broad concept of subunit sequence complementarity between two nucleic acids. When a nucleotide position in both of the molecules is occupied by nucleotides normally capable of base pairing with each other, then the nucleic acids are considered to be complementary to each other at this position. Thus, two nucleic acids are substantially complementary to each other when at least about 50%, at least about 60% or at least about 80% of corresponding positions in each of the molecules are occupied by nucleotides which normally base pair with each other (e.g., A:T and G:C nucleotide pairs).

As used herein, "conjugated" refers to covalent attachment of one molecule to a second molecule.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of a mRNA molecule also consists of the nucleotide residues of the mRNA molecule which are matched with an anti-codon region of a transfer RNA molecule during translation of the mRNA molecule or which encode a stop codon. The coding region may thus include nucleotide residues comprising codons for amino acid residues which are not present in the mature protein encoded by the mRNA molecule (e.g., amino acid residues in a protein export signal sequence).

The term "comparator" describes a material comprising none, or a normal, low, or high level of one of more of the marker (or biomarker) expression products of one or more the markers (or biomarkers) of the invention, such that the comparator may serve as a control or reference standard against which a sample can be compared.

As used herein, the term "derivative" includes a chemical modification of a polypeptide, polynucleotide, or other molecule. In the context of this invention, a "derivative polypeptide," for example, one modified by glycosylation, pegylation, or any similar process, retains binding activity. For example, the term "derivative" of binding domain includes binding domain fusion proteins, variants, or fragments that have been chemically modified, as, for example, by addition of one or more polyethylene glycol molecules, sugars, phosphates, and/or other such molecules, where the molecule or molecules are not naturally attached to wild-type binding domain fusion proteins. A "derivative" of a polypeptide further includes those polypeptides that are "derived" from a reference polypeptide by having, for example, amino acid substitutions, deletions, or insertions relative to a reference polypeptide. Thus, a polypeptide may be "derived" from a wild-type polypeptide or from any other polypeptide. As used herein, a compound, including polypeptides, may also be "derived" from a particular source, for example from a particular organism, tissue type, or from a particular polypeptide, nucleic acid, or other compound that is present in a particular organism or a particular tissue type.

As used herein, the term "diagnosis" means detecting a disease or disorder or determining the stage or degree of a disease or disorder. Usually, a diagnosis of a disease or disorder is based on the evaluation of one or more factors and/or symptoms that are indicative of the disease. That is, a diagnosis can be made based on the presence, absence or amount of a factor which is indicative of presence or absence of the disease or condition. Each factor or symptom that is considered to be indicative for the diagnosis of a particular disease does not need be exclusively related to the particular disease; i.e. there may be differential diagnoses that can be inferred from a diagnostic factor or symptom. Likewise, there may be instances where a factor or symptom that is indicative of a particular disease is present in an individual that does not have the particular disease. The diagnostic methods may be used independently, or in combination with other diagnosing and/or staging methods known in the medical art for a particular disease or disorder.

As used herein, the phrase "difference of the level" refers to differences in the quantity of a particular marker, such as a nucleic acid (e.g., microRNA, etc.) or a protein, in a sample as compared to a control or reference level. For example, the quantity of a particular biomarker may be present at an elevated amount or at a decreased amount in samples of patients with a disease compared to a reference level. In one embodiment, a "difference of a level" may be a difference between the quantity of a particular biomarker present in a sample as compared to a control of at least about 1%, at least about 2%, at least about 3%, at least about 5%, at least about 10%, at least about 15%, at least about 20%, at least about 25%, at least about 30%, at least about 35%, at least about 40%, at least about 50%, at least about 60%, at least about 75%, at least about 80% or more. In one embodiment, a "difference of a level" may be a statistically significant difference between the quantity of a biomarker present in a sample as compared to a control. For example, a difference may be statistically significant if the measured level of the biomarker falls outside of about 1.0 standard deviations, about 1.5 standard deviations, about 2.0 standard deviations, or about 2.5 stand deviations of the mean of any control or reference group.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

The terms "dysregulated" and "dysregulation" as used herein describes a decreased (down-regulated) or increased (up-regulated) level of expression of a miRNA present and detected in a sample obtained from subject as compared to the level of expression of that miRNA in a comparator sample, such as a comparator sample obtained from one or more normal, not-at-risk subjects, or from the same subject at a different time point. In some instances, the level of miRNA expression is compared with an average value obtained from more than one not-at-risk individuals. In other instances, the level of miRNA expression is compared with a miRNA level assessed in a sample obtained from one normal, not-at-risk subject.

By the phrase "determining the level of marker (or biomarker) expression" is meant an assessment of the degree of expression of a marker in a sample at the nucleic acid or protein level, using technology available to the skilled artisan to detect a sufficient portion of any marker expression product.

The terms "determining," "measuring," "assessing," and "assaying" are used interchangeably and include both quantitative and qualitative measurement, and include determining if a characteristic, trait, or feature is present or not. Assessing may be relative or absolute. "Assessing the presence of" includes determining the amount of something present, as well as determining whether it is present or absent.

"Differentially increased expression" or "up regulation" refers to expression levels which are at least 10% or more, for example, 20%, 30%, 40%, or 50%, 60%, 70%, 80%, 90% higher or more, and/or 1.1 fold, 1.2 fold, 1.4 fold, 1.6 fold, 1.8 fold, 2.0 fold higher or more, and any and all whole or partial increments there between compared to a comparator.

"Differentially decreased expression" or "down regulation" refers to expression levels which are at least 10% or more, for example, 20%, 30%, 40%, or 50%, 60%, 70%, 80%, 90% lower or less, and/or 2.0 fold, 1.8 fold, 1.6 fold, 1.4 fold, 1.2 fold, 1.1 fold or less lower, and any and all whole or partial increments there between compared to a comparator.

As used herein "endogenous" refers to any material from or produced inside an organism, cell, tissue or system.

As used herein "exogenous" refers to any material from or produced outside an organism, cell, tissue or system.

The term "expression" as used herein is defined as the transcription and/or translation of a particular nucleotide sequence.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 5'-ATTGCC-3' and 5'-TATGGC-3' share 50% homology.

As used herein, "homology" is used synonymously with "identity."

"Inhibitors," "activators," and "modulators" of the markers are used to refer to activating, inhibiting, or modulating molecules, respectively, identified using in vitro and in vivo assays of HRD biomarkers. Inhibitors are compounds that, e.g., bind to, partially or totally block activity, decrease, prevent, delay activation, inactivate, desensitize, or down regulate the activity or expression of HRD biomarkers. "Activators" are compounds that increase, open, activate, facilitate, enhance activation, sensitize, agonize, or up regulate activity of HRD biomarkers. Agonists, inhibitors, activators, or modulators also include genetically modified versions of HRD biomarkers, e.g., versions with altered activity, as well as naturally occurring and synthetic ligands, antagonists, agonists, antibodies, peptides, cyclic peptides, nucleic acids, antisense molecules, ribozymes, RNA interference (RNAi), microRNA, and small interfering RNA (siRNA) molecules, small organic molecules and the like. Such assays for inhibitors and activators include, e.g., expressing HRD biomarkers in vitro, in cells, or cell extracts, applying putative modulator compounds, and then determining the functional effects on activity, as described elsewhere herein.

The term "inhibit," as used herein, means to suppress or block an activity or function, for example, about ten percent relative to a control value. For example, the activity is suppressed or blocked by 50% compared to a control value, or by 75%, or by 95%. "Inhibit," as used herein, also means to reduce the level of a molecule, a reaction, an interaction, a gene, a miRNA, an mRNA, and/or a protein's expression, stability, amount, function or activity by a measurable amount or to prevent production entirely. Inhibitors are compounds that, e.g., bind to, partially or totally block activity, decrease, prevent, delay activation, inactivate, desensitize, or down regulate a protein, a gene, a miRNA, and an mRNA stability, expression, function and activity, e.g., antagonists.

As used herein, an "instructional material" includes a publication, a recording, a diagram, or any other medium of expression which can be used to communicate the usefulness of a compound, composition, vector, method or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

As used herein, "isolated" means altered or removed from the natural state through the actions, directly or indirectly, of a human being. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

The term "vector," as used in the context of the present invention, refers to a DNA molecule used as a vehicle to carry genetic material into a cell or other host, where it can be replicated and/or expressed.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

"Measuring" or "measurement," or alternatively "detecting" or "detection," means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's clinical parameters.

As used herein, "microRNA" or "miRNA" describes small non-coding RNA molecules, generally about 15 to about 50 nucleotides in length, for example, 17-23 nucleotides in length, which can play a role in regulating gene expression through, for example, a process termed RNA interference (RNAi). RNAi describes a phenomenon whereby the presence of an RNA sequence that is complementary or antisense to a sequence in a target gene messenger RNA (mRNA) results in inhibition of expression of the target gene. miRNAs are processed from hairpin precursors of about 70 or more nucleotides (pre-miRNA) which are derived from primary transcripts (pri-miRNA) through sequential cleavage by RNAse III enzymes. miRBase is a comprehensive microRNA database located at www.mirbase.org, incorporated by reference herein in its entirety for all purposes.

A "mutation," as used herein, refers to a change in nucleic acid or polypeptide sequence relative to a reference sequence (which may be a naturally-occurring normal or "wild-type" sequence), and includes translocations, deletions, insertions, and substitutions/point mutations. A "mutant," as used herein, refers to either a nucleic acid or protein comprising a mutation.

"Naturally occurring" as used herein describes a composition that can be found in nature as distinct from being artificially produced. For example, a nucleotide sequence present in an organism, which can be isolated from a source in nature and which has not been intentionally modified by a person, is naturally occurring.

As used herein, the term "neutralizing" may refer to neutralization of biological activity of a target when a binding molecule specifically binds the target. In the context of miRNAs, a neutralizing binding molecule may be a small molecule, a ribozyme, an antisense nucleic acid molecule, a polypeptide, or another type of molecule, the binding of which to the miRNA results in inhibition of a biological activity of the miRNA. For example, the neutralizing binding molecule binds one or more miRNAs and reduces a biological activity of the miRNAs by at least about 20%, 40%, 60%, 80%, 85% or more.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand." Sequences on the DNA strand which are located 5' to a reference point on the DNA are referred to as "upstream sequences." Sequences on the DNA strand which are 3' to a reference point on the DNA are referred to as "downstream sequences."

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means. "Polynucleotide" includes cDNA, RNA, DNA/RNA hybrid, anti-sense RNA, siRNA, miRNA, genomic DNA, synthetic forms, and mixed polymers, both sense and antisense strands, and may be chemically or biochemically modified to contain non-natural or derivatized, synthetic, or semi-synthetic nucleotide bases. Also, included within the scope of the invention are alterations of a wild type or synthetic gene, including but not limited to deletion, insertion, substitution of one or more nucleotides, or fusion to other polynucleotide sequences.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "conservative substitution," when describing a polypeptide, refers to a change in the amino acid composition of the polypeptide that does not substantially alter the activity of the polypeptide, i.e., substitution of amino acids with other amino acids having similar properties. Conservative substitution tables providing functionally similar amino acids are well known in the art. The following six groups each contain amino acids that are generally understood to represent conservative substitutions for one another: (1) Alanine (A), Serine (S), Threonine (T); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); and (6) Phenylalanine (F), Tyrosine (Y), Tryptophan (W) (see also, Creighton, 1984, Proteins, W.H. Freeman and Company). In addition to the above-defined conservative substitutions, other modifications of amino acid residues can also result in "conservatively modified variants." For example, one may regard all charged amino acids as substitutions for each other whether they are positive or negative. In addition, conservatively modified variants can also result from individual substitutions, deletions or additions which alter, add or delete a single amino acid or a small percentage of amino acids, for example, often less than 5%, in an encoded sequence. Further, a conservatively modified variant can be made from a recombinant polypeptide by substituting a codon for an amino acid employed by the native or wild-type gene with a different codon for the same amino acid.

"Ribozymes" as used herein are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, J. Amer. Med. Assn. 260:3030). There are two basic types of ribozymes, namely, tetrahymena-type (Hasselhoff, 1988, Nature 334:585) and hammerhead-type. Tetrahymena-type ribozymes recognize sequences which are four bases in length, while hammerhead-type ribozymes recognize base sequences 11-18 bases in length. The longer the sequence, the greater the likelihood that the sequence will occur exclusively in the target RNA species. Consequently, in some instances, hammerhead-type ribozymes are generally superior to tetrahymena-type ribozymes for inactivating specific RNA species, and 18-base recognition sequences are superior compared to shorter recognition sequences which may occur randomly within various unrelated RNA molecules. Ribozymes and their use for inhibiting gene expression are also well known in the art (see, e.g., Cech et al., 1992, J. Biol. Chem. 267:17479-17482; Hampel et al., 1989, Biochemistry 28:4929-4933; Eckstein et al., International Publication No. WO 92/07065; Altman et al., U.S. Pat. No. 5,168,053).

The term "RNA" as used herein is defined as ribonucleic acid.

As used herein, a "primer" for amplification is an oligonucleotide that specifically anneals to a target or marker nucleotide sequence. The 3' nucleotide of the primer should be identical to the target or marker sequence at a corresponding nucleotide position for optimal primer extension by a polymerase. As used herein, a "forward primer" is a primer that anneals to the anti-sense strand of double stranded DNA (dsDNA). A "reverse primer" anneals to the sense-strand of dsDNA.

The term "DNA" as used herein is defined as deoxyribonucleic acid.

The term "recombinant DNA" as used herein is defined as DNA produced by joining pieces of DNA from different sources.

The term "recombinant polypeptide" as used herein is defined as a polypeptide produced by using recombinant DNA methods.

By "pharmaceutically acceptable" it is meant, for example, a carrier, diluent or excipient that is compatible with the other ingredients of the formulation and generally safe for administration to a recipient thereof. As used herein, "pharmaceutically acceptable carrier" includes any material, which when combined with the conjugate retains the conjugates' activity and is non-reactive with the subject's immune systems. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules. Typically, such carriers contain excipients such as starch, milk, sugar, some types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well-known conventional methods.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The terms "modulator" and "modulation" of a molecule of interest, as used herein in its various forms, is intended to encompass antagonism, agonism, partial antagonism and/or partial agonism of an activity associated with the molecule of interest. The terms "modulator" and "modulation" are used interchangeably with the terms "regulator" and "regulation," respectively. In various embodiments, "modulators" may inhibit or stimulate molecule expression or activity. Such modulators include small molecules agonists and antagonists of a molecule, i.e., antagomirs, antisense molecules, ribozymes, triplex molecules, and RNAi polynucleotides, and others.

As used herein, the term "providing a prognosis" refers to providing a prediction of the probable course and outcome of HRD, including prediction of severity, duration, chances of recovery, etc. The methods can also be used to devise a suitable therapeutic plan, e.g., by indicating whether or not the condition is still at an early stage or if the condition has advanced to a stage where aggressive therapy would be ineffective.

A "reference level" of a biomarker means a level of the biomarker that is indicative of a particular disease state, phenotype, or lack thereof, as well as combinations of disease states, phenotypes, or lack thereof. A "positive" reference level of a biomarker means a level that is indicative of a particular disease state or phenotype. A "negative" reference level of a biomarker means a level that is indicative of a lack of a particular disease state or phenotype.

"Sample" or "biological sample" as used herein means a biological material isolated from an individual. The biological sample may contain any biological material suitable for detecting the desired biomarkers, and may comprise cellular and/or non-cellular material obtained from the individual.

By the term "specifically binds," as used herein with respect to an antibody, is meant an antibody which recognizes a specific binding partner molecule, but does not substantially recognize or bind other molecules in a sample. For example, an antibody that specifically binds to a binding partner molecule from one species may also bind to that binding partner molecule from one or more species. But, such cross-species reactivity does not itself alter the classification of an antibody as specific. In another example, an antibody that specifically binds to binding partner molecule may also bind to different allelic forms of the binding partner molecule. However, such cross reactivity does not itself alter the classification of an antibody as specific.

In some instances, the terms "specific binding" or "specifically binding", can be used in reference to the interaction of an antibody, a protein, or a peptide with a second binding partner molecule, to mean that the interaction is dependent upon the presence of a particular structure (e.g., an antigenic determinant or epitope) on the binding partner molecule; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody. In some instances, the terms "specific binding" and "specifically binding" refers to selective binding, wherein the antibody recognizes a sequence or conformational epitope important for the enhanced affinity of binding to the binding partner molecule.

"Standard control value" as used herein refers to a predetermined amount of a particular protein or nucleic acid that is detectable in a biological sample. The standard control value is suitable for the use of a method of the present invention, in order for comparing the amount of a protein or nucleic acid of interest that is present in a biological sample. An established sample serving as a standard control provides an average amount of the protein or nucleic acid of interest in the biological sample that is typical for an average, healthy person of reasonably matched background, e.g., gender, age, ethnicity, and medical history. A standard control value may vary depending on the protein or nucleic acid of interest and the nature of the sample (e.g., serum).

The terms "subject," "patient," "individual," and the like are used interchangeably herein, and refer to any animal, or cells thereof whether in vitro or in situ, amenable to the methods described herein. Thus, the individual may include, for example, dogs, cats, pigs, cows, sheep, goats, horses, rats, monkeys, and mice and humans. In some non-limiting embodiments, the patient, subject or individual is a human.

The phrase "percent (%) identity" refers to the percentage of sequence similarity found in a comparison of two or more amino acid sequences. Percent identity can be determined electronically using any suitable software. Likewise, "similarity" between two polypeptides (or one or more portions of either or both of them) is determined by comparing the amino acid sequence of one polypeptide to the amino acid sequence of a second polypeptide. Any suitable algorithm useful for such comparisons can be adapted for application in the context of the invention.

A "therapeutic" treatment is a treatment administered to a subject who exhibits signs of pathology, for the purpose of diminishing or eliminating those signs.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

The terms "treat," "treating," and "treatment," refer to therapeutic or preventative measures described herein. The methods of "treatment" employ administration to a subject, in need of such treatment, a composition of the present invention, for example, a subject afflicted a disease or disorder or a subject who ultimately may acquire such a disease or disorderin order to prevent, cure, delay, reduce the severity of, or ameliorate one or more symptoms of the disorder or recurring disorder, or in order to prolong the survival of a subject beyond that expected in the absence of such treatment.

The terms "underexpress," "underexpression," "underexpressed," or "down-regulated" interchangeably refer to a protein or nucleic acid that is transcribed or translated at a detectably lower level in a biological sample from a subject with HRD, in comparison to a biological sample from a subject without HRD. The term includes underexpression due to transcription, post transcriptional processing, translation, post-translational processing, cellular localization (e.g., organelle, cytoplasm, nucleus, cell surface), and RNA and protein stability, as compared to a control. Underexpression can be detected using conventional techniques for detecting mRNA (i.e., Q-PCR, RT-PCR, PCR, hybridization) or proteins (i.e., ELISA, immunohistochemical techniques). Underexpression can be 10%, 20%, 30%, 40%, 50%, 60%, 70%, 80%, 90% or less in comparison to a control. In some instances, underexpression is 1-, 2-, 3-, 4-, 5-, 6-, 7-, 8-, 9-, 10-fold or more lower levels of transcription or translation in comparison to a control.

The terms "overexpress," "overexpression," "overexpressed," or "up-regulated" interchangeably refer to a protein or nucleic acid (RNA) that is transcribed or translated at a detectably greater level, usually in a biological sample from a subject with HRD, in comparison to a biological sample from a subject without HRD. The term includes overexpression due to transcription, post transcriptional processing, translation, post-translational processing, cellular localization (e.g., organelle, cytoplasm, nucleus, cell surface), and RNA and protein stability, as compared to a cell from a subject without HRD. Overexpression can be detected using conventional techniques for detecting mRNA (i.e., Q-PCR, RT-PCR, PCR, hybridization) or proteins (i.e., ELISA, immunohistochemical techniques). Overexpression can be 10%, 20%, 30%, 40%, 50%, 60%, 70%, 80%, 90% or more in comparison to a cell from a subject without HRD. In some instances, overexpression is 1-, 2-, 3-, 4-, 5-, 6-, 7-, 8-, 9-, 10-fold, or more higher levels of transcription or translation in comparison to a cell from a subject without HRD.

"Variant" as the term is used herein, is a nucleic acid sequence or a peptide sequence that differs in sequence from a reference nucleic acid sequence or peptide sequence respectively, but retains essential properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention is based, in part, on the discovery of specific miRNAs that are dysregulated in hyperlipidemia-related diseases (HRDs), including atherosclerosis, NAFLD, obesity, type II diabetes (T2DM), and metabolically healthy obesity (MHO). In one embodiment, the present invention is based, in part, on the discovery of groups of miRNAs that are unique to one HRD as well as miRNAs modulated in comorbidities, or combinations of HRDs.

In one embodiment, the present invention is based, in part, on the discovery that MHO has heterogeneity in comorbidities, and is classified into two types: type-I characterized by decreased expression of miR-221, and type-II characterized by decreased expression of miR-221 and miR-155. Therefore, the invention is based, in part, on the discovery that miR-221 and miR-155 serve as master regulators for type I-, and type II-MHO, respectively, and that detection, or modulation, of these miR can provide diagnostic markers for, or treatment for, the pathogenesis of MHO, hyperlipidemic comorbidities, and hyperlipidemic pathways related to cancer.

In one aspect, the present invention relates to the discovery of a link between hyperlipidemia-related diseases (HRDs), including metabolically healthy obesity (MHO), atherosclerosis, NAFLD, obesity and type II diabetes (T2DM), and alterations in circulating miRNA levels. In some embodiments, the level of circulating miRNAs can be used for detection or diagnosis of HRDs. In an exemplary embodiment, the HRD disease is MHO, and the miRNA are selected from the group consisting of miR-221 and miR-155.

In one aspect, the present invention relates to compositions for modulating one or more miRNA of the invention for the treatment or prevention of a HRD or associated disease or disorder. In various embodiments, the methods and compositions of the invention are useful for treating or preventing a disease or disorder including, but not limited to, obesity, diabetes mellitus, NAFLD, liver cirrhosis, atherosclerosis, and cancers, including but not limited to colorectal cancer (CRC), hepatocellular carcinoma (HCC), breast cancer, pancreatic cancer, endometrial cancer, renal cell carcinoma (RCC), prostate cancer, ovarian cancer, and lung cancer.

While, in specific instances, the description may refer to miRNA species having a 5p or 3p notation, the present invention encompasses the use of both the 5p and 3p versions of each miRNA species. Sequences of the miRNA family members are publicly available from miRbase.

In one aspect, the methods generally provide for the detection, measuring, and comparison of a pattern of circulating miRNA in a patient sample. In various embodiments, the present methods relate to HRD disorder diagnosis by determining the levels of miRNAs in the blood or plasma of patients having or suspected of having a HRD. An alteration (i.e., an increase or decrease) in the level of a miRNA in the sample obtained from the subject, relative to the level of a corresponding miRNA in a control sample, is indicative of the presence of a HRD disease in the subject. In one embodiment, the level of at least one miRNA in the test sample is greater than the level of the corresponding miRNA in the control sample. In another embodiment, the level of at least one miRNA in the test sample is less than the level of the corresponding miRNA in the control sample.

Additional diagnostic markers may be combined with the circulating miRNA level to construct models for predicting the presence or absence or stage of a disease. For example, clinical factors of relevance to the diagnosis of a HRD include, but are not limited to, the patient's medical history, a physical examination, and other biomarkers.

Generally, the methods of this invention find use in diagnosing or for providing a prognosis for a HRD by detecting the expression levels of biomarkers, which are differentially expressed (up- or down-regulated) in blood or serum from a patient. These markers can be used to distinguish the stage or severity of the HRD. These markers can also be used to provide a prognosis for the course of treatment in a patient with a HRD. The biomarkers of the present invention can be used alone or in combination for the diagnosis or prognosis of a HRD.

In one embodiment, the methods of the present invention find use in assigning treatment to a patient suffering from a HRD. By detecting the expression levels of biomarkers found herein, the appropriate treatment or therapy can be assigned to a patient suffering from a HRD. These treatments can include, but are not limited to, lifestyle management, administration of pharmaceutical agents, surgical treatment, and other therapies.

Diagnostic and prognostic kits comprising one or more markers for use are provided herein. Also provided by the invention are methods for identifying compounds that are able to prevent or treat a HRD by modulating the expression level or activity of markers found in any one of the identified gene subsets. Therapeutic methods are provided, wherein a HRD is treated using an agent that targets or modulates the markers of the invention.

In various embodiments, the methods of the invention relate to methods of assessing a subject's risk of having or developing a HRD, methods of assessing the severity of a subject's HRD, methods of diagnosing a HRD, methods of characterizing a HRD, and methods of stratifying a subject having a HRD in a clinical trial.

In various embodiments of the compositions and methods of the invention described herein, the miRNA associated with atherosclerosis is at least one of the following miRNAs: miR-880, miR-295, miR-302d, miR-291a, miR-744, miR-208, miR-712, miR-205, miR-200, miR-222, miR-210, let-7c, miR-19b, miR-92a, miR-29, miR-144, miR-34a, miR-126, miR-155, miR-342, miR-221, miR-21, miR-133, miR-101a, miR-10a, miR-145, miR-1, miR-181b, let-7g, miR-143, miR-199a, miR-26a, let-7b, miR-19a, miR-146a, and miR-335. In one embodiment, at least one of miR-133, miR-101a, miR-10a, miR-145, miR-1, miR-181b, let-7g, miR-143, miR-199a, miR-26a, let-7b, miR-19a, miR-146a, and miR-335 is decreased in atherosclerosis as compared to a comparator control. In one embodiment, at least one of miR-880, miR-295, miR-302d, miR-291a, miR-744, miR-208, miR-712, miR-205, miR-200, miR-222, miR-210, let-7c, miR-19b, miR092a, miR-29, miR-144, miR-34a, miR-126, miR-155, miR-342, miR-221, and miR-21 is increased in atherosclerosis as compared to a comparator control. In one embodiment, an increased level of at least one of miR-126, miR-155, miR-342, miR-880, miR-295, miR-302d, miR-291a, miR-744, miR-208, miR-712, miR-205 is useful for differentially diagnosing a subject as having or at risk of atherosclerosis, but not obesity, T2DM/IR or NAFLD. In one embodiment, a decreased level of at least one of miR-19a, miR-335, miR-101a, miR-10a, miR-145, miR-1, miR-181b, and let-7g is useful for differentially diagnosing a subject as having or at risk of atherosclerosis, but not obesity, T2DM/IR or NAFLD.

In various embodiments of the compositions and methods of the invention described herein, the miRNA associated with T2DM/IR is at least one of the following miRNAs: miR-320a, miR-376a, miR-140, miR-107, miR-212, miR-499, miR-375, miR-589, miR-15b, miR-106b, miR-185, let-7f, miR-144, miR-34a, miR-16, miR-26b, miR-18a, miR-29, miR-146b, miR-221, miR-143, miR-199a, miR-374b, miR-20b, miR-381, miR-487b, miR-203, miR-301a, miR-129, miR-331, miR-486, miR-15a, miR-98, miR-152, miR-190, miR-133, miR-135b, miR-100, miR-99a, miR-155, let-7b, miR-30, miR-126 and miR-342. In one embodiment, at least one of miR-374b, miR-20b, miR-381, miR-487b, miR-203, miR-301a, miR-129, miR-331, miR-486, miR-15a, miR-98, miR-152, miR-190, miR-133, miR-135b, miR-100, miR-99a, miR-155, let-7b, miR-30, miR-126 and miR-342 is decreased in T2DM/IR as compared to a comparator control. In one embodiment, at least one of miR-320a, miR-376a, miR-140, miR-107, miR-212, miR-499, miR-375, miR-589, miR-15b, miR-106b, miR-185, let-7f, miR-144, miR-34a, miR-16, miR-26b, miR-18a, miR-29, miR-146b, miR-221, miR-143 and miR-199a is increased in T2DM/IR as compared to a comparator control. In one embodiment, an increased level of at least one of miR-320a, miR-376a, miR-140, miR-107, miR-212, miR-499, miR-375, miR-589, miR-15b, miR-106b, miR-185, let-7f, miR-143 and miR-199a is useful for differentially diagnosing a subject as having or at risk of T2DM/IR, but not obesity, atherosclerosis or NAFLD. In one embodiment, a decreased level of at least one of miR-374b, miR-20b, miR-381, miR-487b, miR-203, miR-301a, miR-129, miR-331, miR-486, miR-15a, miR-98, miR-152, miR-190, miR-30, miR-126b, and miR-342 is useful for differentially diagnosing a subject as having or at risk of T2DM/IR, but not obesity, atherosclerosis or NAFLD.

In various embodiments of the compositions and methods of the invention described herein, the miRNA associated with NAFLD is at least one of the following miRNAs: miR-181d, miR-132, miR-150, miR-511, miR-671, miR-433, miR-128, miR-451, miR-99b, miR-28, miR-517a, let-7d, miR-155, miR-21, miR-99a, miR-370, miR-224, miR-31, miR-22, miR-10b, miR-429, miR-181a, miR-33, miR-200, miR-222, miR-146b, miR-34a, miR-16, miR-221, let-7b, and miR-26a. In one embodiment, at least one of miR-181d, miR-132, miR-150, miR-511, miR-671, miR-433, miR-128, miR-451, miR-99b, miR-28, miR-517a, let-7d, miR-155, miR-21 and miR-99a is decreased in NAFLD as compared to a comparator control. In one embodiment, at least one of miR-370, miR-224, miR-31, miR-22, miR-10b, miR-429, miR-181a, miR-33, miR-200, miR-222, miR-146b, miR-34a, miR-16, miR-221, let-7b and miR-26a is increased in NAFLD as compared to a comparator control. In one embodiment, an increased level of at least one of miR-370, miR-224, miR-31, miR-22, miR-10b, miR-429, miR-181a, miR-33, let-7b and miR-26a is useful for differentially diagnosing a subject as having or at risk of NAFLD, but not obesity, atherosclerosis or T2DM/IR. In one embodiment, a decreased level of at least one of miR-21, miR-181d, miR-132, miR-150, miR-511, miR-671, miR-433, miR-128, miR-451, miR-99b, miR-28, miR-517a, and let-7d is useful for differentially diagnosing a subject as having or at risk of NAFLD, but not obesity, atherosclerosis or T2DM/IR.

In various embodiments of the compositions and methods of the invention described herein, the miRNA associated with obesity is at least one of the following miRNAs: miR-155, miR-221, miR-503, miR-27, miR-493, miR-136, miR-654, miR-758, miR-432, miR-1275, miR-193b-365, miR-135b, miR-100, miR-17, miR-20a, miR-378, miR-519d, miR-355, miR-148a, miR-1247, miR-3124, miR-1343, miR-191, miR-30, miR-21, miR-19a, miR-146a, miR-26b, miR-18a, miR-210, miR-19b, miR-92a, miR-29, miR-146b, let-7c and miR-335. In one embodiment, at least one of miR-155, miR-221, miR-503, miR-27, miR-493, miR-136, miR-654, miR-758, miR-432, miR-1275, miR-193b-365, miR-135b, and miR-100 is decreased in obesity as compared to a comparator control. In one embodiment, at least one of miR-17, miR-20a, miR-378, miR-519d, miR-355, miR-148a, miR-1247, miR-3124, miR-1343, miR-191, miR-30, miR-21, miR-19a, miR-146a, miR-26b, miR-18a, miR-210, miR-19b, miR-92a, miR-29, miR-146b, let-7c and miR-335 is increased in obesity as compared to a comparator control. In one embodiment, an increased level of at least one of miR-17, miR-20a, miR-378, miR-519d, miR-355, miR-148a, miR-1247, miR-3124, miR-1343, miR-191, miR-19a, miR-30, miR-146a, miR-335 is useful for differentially diagnosing a subject as having or at risk of obesity, but not NAFLD, atherosclerosis or T2DM/IR. In one embodiment, a decreased level of at least one of miR-221, miR-503, miR-27, miR-493, miR-136, miR-654, miR-758, miR-432, miR-1275, and miR-193b-365 is useful for differentially diagnosing a subject as having or at risk of obesity, but not NAFLD, atherosclerosis or T2DM/IR.

In one embodiment, a level of at least one of miR-221 and miR-155 is useful for differentially diagnosing a subject as having, or at risk of, MHO type I, MHO type II or obesity associated with T2DM/IR. In one embodiment, miR-221, but not miR-155, is decreased in MHO type I as compared to a comparator control. In one embodiment, a combination of miR-221 and miR-155 is decreased in MHO type II as compared to a comparator control. In one embodiment, miR-155, but not miR-221, is decreased in obesity associated with T2DM/IR as compared to a comparator control.

In some embodiments, the biomarkers of the invention are useful for indicating co-morbid conditions. For example, in one embodiment at least one of an increase in miR-144, a decrease in let-7b, and a decrease in miR-133 is associated with the combination of atherosclerosis and T2DM/IR. In one embodiment at least one of an increase in miR-19b, an increase in let-7c, an increase in miR-21, an increase in miR-92a and an increase in miR-201 is associated with the combination of atherosclerosis and obesity. In one embodiment at least one of an increase in miR-200, and an increase in miR-222 is associated with the combination of atherosclerosis and NAFLD. In one embodiment at least one of an increase in miR-26b, an increase in miR-18a, a decrease in miR-135b, and a decrease in miR-100 is associated with the combination of T2DM/IR and obesity. In one embodiment, at least one of an increase in miR-16 and a decrease in miR-99a is associated with the combination of NAFLD and T2DM/IR. In one embodiment, an increase in miR-29 is associated with the combination of atherosclerosis, obesity and T2DM/IR. In one embodiment, at least one of an increase in miR-221 and an increase in miR-34 is associated with the combination of atherosclerosis, NAFLD and T2DM/IR. In one embodiment, an increase in miR-149b is associated with the combination of atherosclerosis, NAFLD and T2DM/IR.

In one embodiment, the invention provides a method for detecting a marker of a HRD. In one embodiment, the invention provides a method for monitoring the levels of miRNAs in response to treatment. In one embodiment, the invention provides a method for monitoring at least one of miR-320a, miR-376a, miR-140, miR-107, miR-212, miR-499, miR-375, miR-589, miR-15b, miR-106b, miR-185, let-7f, miR-144, miR-34a, miR-16, miR-26b, miR-18a, miR-29, miR-146b, miR-221, miR-143, miR-199a, miR-374b, miR-20b, miR-381, miR-487b, miR-203, miR-301a, miR-129, miR-331, miR-486, miR-15a, miR-98, miR-152, miR-190, miR-133, miR-135b, miR-100, miR-99a, miR-155, let-7b, miR-30, miR-126, miR-342, miR-181d, miR-132, miR-150, miR-511, miR-671, miR-433, miR-128, miR-451, miR-99b, miR-28, miR-517a, let-7d, miR-370, miR-224, miR-31, miR-22, miR-10b, miR-429, miR-181a, miR-33, miR-200, miR-222, miR-21, miR-26a, miR-503, miR-27, miR-493, miR-136, miR-654, miR-758, miR-432, miR-1275, miR-193b-365, miR-17, miR-20a, miR-378, miR-519d, miR-355, miR-148a, miR-1247, miR-3124, miR-1343, miR-191, miR-210, miR-19b, miR-92a, let-7c, miR-335, miR-19a, miR-146a, miR-880, miR-295, miR-302d, miR-291a, miR-744, miR-208, miR-712, miR-205, miR-101a, miR-10a, miR-145, miR-1, miR-181b, and let-7g.

In one embodiment, a treatment-induced decrease in any of the miRNAs that are upregulated in a disease state is indicative of treatment efficacy or that a subject is responsive to treatment. Similarly, in one embodiment, a treatment-induced increase in any of the miRNAs that are downregulated in a disease state is indicative of treatment efficacy or that a subject is responsive to treatment. Additionally, in certain embodiments, a treatment-induced increase in any of the miRNAs that are upregulated in a disease state is indicative that the subject is not responsive to treatment. Similarly, in one embodiment, a treatment-induced decrease in any of the miRNAs that are downregulated in a disease state is indicative that the subject is not responsive to treatment. Additionally, in certain embodiments, a lack of a treatment-induced decrease in any of the miRNAs that are upregulated in a disease state is indicative that the subject is not responsive to treatment. Similarly, in certain embodiments, a lack of a treatment-induced increase in any of the miRNAs that are downregulated in a disease state is indicative that the subject is not responsive to treatment.

The miRNAs may be detected and measured using any methods presented herein, including but not limited to hybridization assays, direct sequencing methods, and array-based methods. The miRNAs may be reverse-transcribed and amplified by polymerase chain reaction, using a detectable reporter molecule for measuring amounts of the miRNAs in the biological sample. These assays are known in the art.

Accordingly, the invention provides a new and convenient platform for detecting a marker of a HRD. In one embodiment, the system of the invention provides a platform for detecting a marker of a HRD with at least 80% sensitivity, at least 90%, at least 91%, at least 92%, at least 93%, at least 94%, at least 95%, at least 96%, at least 97%, at least 98%, at least 99%, or at least 100%.

In one embodiment, the invention provides a system for detecting a marker of a HRD, with at least 90%, 91%, 92%, 93%, 94%, 95%, 96%, 97%, 98%, 99%, 100% sensitivity; at least 90%, 91%, 92%, 93%, 94%, 95%, 96%, 97%, 98%, 99%, 100% specificity; or both at least 90%, 91%, 92%, 93%, 94%, 95%, 96%, 97%, 98%, 99%, 100% sensitivity and specificity. In one embodiment, the invention provides a system for detecting a marker of HRD with at least 90%, 91%, 92%, 93%, 94%, 95%, 96%, 97%, 98%, 99%, 100% accuracy.

Sample Preparation

Test samples of acellular body fluid or cell-containing samples may be obtained from an individual or patient. Methods of obtaining test samples are well-known to those of skill in the art and include, but are not limited to aspirations or drawing of blood or other fluids. Samples may include, but are not limited to, whole blood, serum, plasma, saliva, cerebrospinal fluid (CSF), pericardial fluid, pleural fluid, synovial fluid, urine, and eye fluid. In some embodiments in which the test sample contains cells, the cells may be removed from the liquid portion of the sample by methods known in the art (e.g., centrifugation) to yield acellular body fluid. In suitable embodiments, serum or plasma are used as the acellular body fluid sample. Plasma and serum can be prepared from whole blood using suitable methods well-known in the art. In these embodiments, data may be normalized by volume of acellular body fluid.

Variability in sample preparation of cell-containing samples can be corrected by normalizing the data by, for example, protein content or cell number. In some embodiments, the sample may be normalized relative to the total protein content in the sample. Total protein content in the sample can be determined using standard procedures, including, without limitation, Bradford assay and the Lowry method. In other embodiments, the sample may be normalized relative to cell number.

Assays

The present invention relates to the discovery that the expression level of particular miRNAs is associated with the presence, development, progression and severity of HRD. In various embodiments, the invention relates to a genetic screening assay of a subject to determine the level of expression of at least one miRNA associated with HRD in the subject. The present invention provides methods of assessing level of at least one miRNA associated with HRD, as well as methods of diagnosing a subject as having, or as being at risk of developing, HRD based upon the level of expression of at least one miRNA associated with HRD. In some embodiments, the diagnostic assays described herein are in vitro assays.

In one embodiment, the method of the invention is a diagnostic assay for assessing the presence, development, progression and severity of HRD in a subject in need thereof, by determining whether the level of at least one miRNA associated with HRD is increased or decreased in a biological sample obtained from the subject. In various embodiments, to determine whether the level of the at least one miRNA associated with HRD is increased or decreased in a biological sample obtained from the subject, the level of the at least one miRNA is compared with the level of at least one comparator control, such as a positive control, a negative control, a normal control, a wild-type control, a historical control, a historical norm, or the level of another reference molecule in the biological sample. In some embodiments, the diagnostic assay of the invention is an in vitro assay. In other embodiments, the diagnostic assay of the invention is an in vivo assay. The miRNA identified by the assay can be any miRNA that is associated with HRD. In some embodiments, the miRNA is at least one of miR-320a, miR-376a, miR-140, miR-107, miR-212, miR-499, miR-375, miR-589, miR-15b, miR-106b, miR-185, let-7f, miR-144, miR-34a, miR-16, miR-26b, miR-18a, miR-29, miR-146b, miR-221, miR-143, miR-199a, miR-374b, miR-20b, miR-381, miR-487b, miR-203, miR-301a, miR-129, miR-331, miR-486, miR-15a, miR-98, miR-152, miR-190, miR-133, miR-135b, miR-100, miR-99a, miR-155, let-7b, miR-30, miR-126, miR-342, miR-181d, miR-132, miR-150, miR-511, miR-671, miR-433, miR-128, miR-451, miR-99b, miR-28, miR-517a, let-7d, miR-370, miR-224, miR-31, miR-22, miR-10b, miR-429, miR-181a, miR-33, miR-200, miR-222, miR-21, miR-26a, miR-503, miR-27, miR-493, miR-136, miR-654, miR-758, miR-432, miR-1275, miR-193b-365, miR-17, miR-20a, miR-378, miR-519d, miR-355, miR-148a, miR-1247, miR-3124, miR-1343, miR-191, miR-210, miR-19b, miR-92a, let-7c, miR-335, miR-19a, miR-146a, miR-880, miR-295, miR-302d, miR-291a, miR-744, miR-208, miR-712, miR-205, miR-101a, miR-10a, miR-145, miR-1, miR-181b, and let-7g. In various embodiments of the invention, the miRNA identified by the assay can be at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, or more than 100 miRNA associated with HRD. The results of the diagnostic assay can be used alone, or in combination with other information from the subject, or other information from the biological sample obtained from the subject.

In various embodiments of the assays of the invention, the level of the at least one miRNA associated with HRD is determined to be down-regulated when the level of the at least one miRNA is decreased by at least 5%, by at least 10%, by at least 20%, by at least 30%, by at least 40%, by at least 50%, by at least 60%, by at least 70%, by at least 80%, by at least 90%, by at least 100%, by at least 125%, by at least 150%, by at least 175%, by at least 200%, by at least 250%, by at least 300%, by at least 400%, by at least 500%, by at least 600%, by at least 700%, by at least 800%, by at least 900%, by at least 1000%, by at least 1500%, by at least 2000%, or by at least 5000%, when compared with a comparator control.

In various embodiments of the assays of the invention, the level of the at least one miRNA associated with HRD is determined to be up-regulated when the level of the at least one miRNA is increased by at least 5%, by at least 10%, by at least 20%, by at least 30%, by at least 40%, by at least 50%, by at least 60%, by at least 70%, by at least 80%, by at least 90%, by at least 100%, by at least 125%, by at least 150%, by at least 175%, by at least 200%, by at least 250%, by at least 300%, by at least 400%, by at least 500%, by at least 600%, by at least 700%, by at least 800%, by at least 900%, by at least 1000%, by at least 1500%, by at least 2000%, or by at least 5000%, when compared with a comparator control.

In the assay methods of the invention, a test biological sample from a subject is assessed for the expression level of at least one miRNA associated with HRD. The test biological sample can be an in vitro sample or an in vivo sample. In various embodiments, the subject is a human subject, and may be of any race, sex and age. Representative subjects include those who are suspected of having HRD, those who have been diagnosed with HRD, those who have had HRD, those who at risk of a recurrence of HRD, and those who are at risk of developing HRD.

In some embodiments, a HRD associated miRNA-binding molecule is used in vivo for the diagnosis of HRD. In some embodiments, the HRD associated miRNA-binding molecule is nucleic acid that hybridizes with a HRD associated miRNA of the invention.

In one embodiment, the test sample is a sample containing at least a fragment of a nucleic acid comprising a miRNA associated with HRD. The term, "fragment," as used herein, indicates that the portion of a nucleic acid (e.g., DNA, mRNA or cDNA) that is sufficient to identify it as comprising a miRNA associated with HRD.

In some embodiments, the test sample is prepared from a biological sample obtained from the subject. The biological sample can be a sample from any source which contains a nucleic acid comprising HRD associated miRNA, such as a body fluid (e.g., blood, plasma, serum, synovial fluid, saliva, urine, etc.), or a tissue, or an exosome, or a cell, or a combination thereof. A biological sample can be obtained by appropriate methods, such as, by way of examples, biopsy or fluid draw. The biological sample can be used as the test sample; alternatively, the biological sample can be processed to enhance access to polypeptides, nucleic acids, or copies of nucleic acids (e.g., copies of nucleic acids comprising a miRNA associated with HRD), and the processed biological sample can then be used as the test sample. For example, in various embodiments, nucleic acid is prepared from a biological sample, for use in the methods. Alternatively, or in addition, if desired, an amplification method can be used to amplify nucleic acids comprising all or a fragment of a nucleic acid in a biological sample, for use as the test sample in the assessment of the expression level of a miRNA associated with HRD.

The test sample is assessed to determine the level of expression of at least one miRNA associated with HRD present in the nucleic acid of the subject. In general, detecting a miRNA may be carried out by determining the presence or absence of a nucleic acid containing a miRNA of interest in the test sample.

In some embodiments, hybridization methods, such as Northern analysis, or in situ hybridizations, can be used (see Current Protocols in Molecular Biology, 2012, Ausubel, F. et al., eds., John Wiley & Sons, including all supplements). For example, the presence of a miRNA associated with HRD can be indicated by hybridization to a nucleic acid probe. A "nucleic acid probe," as used herein, can be a nucleic acid probe, such as a DNA probe or an RNA probe. For representative examples of use of nucleic acid probes, see, for example, U.S. Pat. Nos. 5,288,611 and 4,851,330.

To detect at least one miRNA of interest, a hybridization sample is formed by contacting the test sample with at least one nucleic acid probe. A probe for detecting miRNA is a labeled nucleic acid probe capable of hybridizing to miRNA. The nucleic acid probe can be, for example, a full-length nucleic acid molecule, or a portion thereof, such as an oligonucleotide of at least 10, 15, or 25 nucleotides in length and sufficient to specifically hybridize under stringent conditions to appropriate miRNA. The hybridization sample is maintained under conditions which are sufficient to allow specific hybridization of the nucleic acid probe to a miRNA target of interest. Specific hybridization can be performed under high stringency conditions or moderate stringency conditions, as appropriate. In an exemplary embodiment, the hybridization conditions for specific hybridization are high stringency. Specific hybridization, if present, is then detected using standard methods. If specific hybridization occurs between the nucleic acid probe and a miRNA in the test sample, the sequence that is present in the nucleic acid probe is also present in the miRNA of the subject. More than one nucleic acid probe can also be used concurrently in this method. Specific hybridization of any one of the nucleic acid probes is indicative of the presence of the miRNA of interest, as described herein.

Alternatively, a peptide nucleic acid (PNA) probe can be used instead of a nucleic acid probe in the hybridization methods described herein. PNA is a DNA mimic having a peptide-like, inorganic backbone, such as N-(2-aminoethyl) glycine units, with an organic base (A, G, C, T or U) attached to the glycine nitrogen via a methylene carbonyl linker (see, for example, 1994, Nielsen et al., Bioconjugate Chemistry 5:1). The PNA probe can be designed to specifically hybridize to a nucleic acid sequence comprising at least one miRNA of interest. Hybridization of the PNA probe to a nucleic acid sequence is indicative of the presence of a miRNA of interest.

Direct sequence analysis can also be used to detect miRNAs of interest. A sample comprising nucleic acid can be used, and PCR or other appropriate methods can be used to amplify all or a fragment of the nucleic acid, and/or its flanking sequences, if desired.

In another embodiment, arrays of oligonucleotide probes that are complementary to target nucleic acid sequences from a subject can be used to detect, identify and quantify miRNAs associated with HRD. For example, in one embodiment, an oligonucleotide array can be used. Oligonucleotide arrays typically comprise a plurality of different oligonucleotide probes that are coupled to a substrate in different known locations. These oligonucleotide arrays, also known as "Genechips," have been generally described in the art, for example, U.S. Pat. No. 5,143,854 and PCT patent publication Nos. WO 90/15070 and 92/10092. These arrays can generally be produced using mechanical synthesis methods or light directed synthesis methods which incorporate a combination of photolithographic methods and solid phase oligonucleotide synthesis methods. See Fodor et al., Science, 251:767-777 (1991), Pirrung et al., U.S. Pat. No. 5,143,854 (see also PCT Application No. WO 90/15070) and Fodor et al., PCT Publication No. WO 92/10092 and U.S. Pat. No. 5,424,186. Techniques for the synthesis of these arrays using mechanical synthesis methods are described in, e.g., U.S. Pat. No. 5,384,261.

After an oligonucleotide array is prepared, a sample containing miRNA is hybridized with the array and scanned for miRNAs. Hybridization and scanning are generally carried out by methods described herein and also in, e.g., Published PCT Application Nos. WO 92/10092 and WO 95/11995, and U.S. Pat. No. 5,424,186, the entire teachings of which are incorporated by reference herein.

In brief, a target miRNA sequence is amplified by well-known amplification techniques, e.g., RT, PCR. Typically, this involves the use of primer sequences that are complementary to the target miRNA. Amplified target, generally incorporating a label, is then hybridized with the array under appropriate conditions. Upon completion of hybridization and washing of the array, the array is scanned to determine the position on the array to which the target sequence hybridizes. The hybridization data obtained from the scan is typically in the form of fluorescence intensities as a function of location on the array.

Other methods of nucleic acid analysis can be used to detect miRNAs of interest. Representative methods include direct manual sequencing (1988, Church and Gilbert, Proc. Natl. Acad. Sci. USA 81:1991-1995; 1977, Sanger et al., Proc. Natl. Acad. Sci. 74:5463-5467; Beavis et al. U.S. Pat. No. 5,288,644); automated fluorescent sequencing; single-stranded conformation polymorphism assays (SSCP); clamped denaturing gel electrophoresis (CDGE); denaturing gradient gel electrophoresis (DGGE) (Sheffield et al., 1981, Proc. Natl. Acad. Sci. USA 86:232-236), mobility shift analysis (Orita et al., 1989, Proc. Natl. Acad. Sci. USA 86:2766-2770; Rosenbaum and Reissner, 1987, Biophys. Chem. 265:1275; 1991, Keen et al., Trends Genet. 7:5); RNase protection assays (Myers, et al., 1985, Science 230: 1242); Luminex xMAP™ technology; high-throughput sequencing (HTS) (Gundry and Vijg, 2011, Mutat Res, doi:10.1016/j.mrfmmm.2011.10.001); next-generation sequencing (NGS) (Voelkerding et al., 2009, Clinical Chemistry 55:641-658; Su et al., 2011, Expert Rev Mol Diagn. 11:333-343; Ji and Myllykangas, 2011, Biotechnol Genet Eng Rev 27:135-158); and/or ion semiconductor sequencing (Rusk, 2011, Nature Methods doi:10.1038/nmeth.f.330; Rothberg et al., 2011, Nature 475:348-352). These and other methods, alone or in combination, can be used to detect and quantify of at least one miRNA of interest, in a biological sample obtained from a subject. In one embodiment of the invention, the methods of assessing a biological sample to detect and quantify a miRNA of interest, as described herein, are used to diagnose, assess and characterize HRD in a subject in need thereof.

The probes and primers according to the invention can be labeled directly or indirectly with a radioactive or nonradioactive compound, by methods well known to those skilled in the art, in order to obtain a detectable and/or quantifiable signal; the labeling of the primers or of the probes according to the invention is carried out with radioactive elements or with nonradioactive molecules. Among the radioactive isotopes used, mention may be made of $^{32}P$, $^{33}P$, $^{35}S$ or $^{3}H$. The nonradioactive entities are selected from ligands such as biotin, avidin, streptavidin or digoxigenin, haptenes, dyes, and luminescent agents such as radioluminescent, chemoluminescent, bioluminescent, fluorescent or phosphorescent agents.

Nucleic acids can be obtained from the biological sample using known techniques. Nucleic acid herein includes RNA, including mRNA, miRNA, etc. The nucleic acid can be double-stranded or single-stranded (i.e., a sense or an antisense single strand) and can be complementary to a nucleic acid encoding a polypeptide. The nucleic acid content may also be obtained from an extraction performed on a fresh or fixed biological sample.

There are many methods known in the art for the detection of specific nucleic acid sequences and new methods are continually reported. A great majority of the known specific nucleic acid detection methods utilize nucleic acid probes in specific hybridization reactions.

In the Northern blot, the nucleic acid probe may be labeled with a tag. That tag can be a radioactive isotope, a fluorescent dye or the other well-known materials. Another type of process for the specific detection of nucleic acids of exogenous organisms in a body sample known in the art are the hybridization methods as exemplified by U.S. Pat. Nos. 6,159,693 and 6,270,974, and related patents. To briefly summarize one of those methods, a nucleic acid probe of at least 10 nucleotides, at least 15 nucleotides, or at least 25 nucleotides, having a sequence complementary to a desired region of the target nucleic acid of interest is hybridized in a sample, subjected to depolymerizing conditions, and the sample is treated with an ATP/luciferase system, which will luminesce if the nucleic sequence is present. In quantitative Northern blotting, levels of the polymorphic nucleic acid can be compared to wild-type levels of the nucleic acid.

A further process for the detection of hybridized nucleic acid takes advantage of the polymerase chain reaction (PCR). The PCR process is well known in the art (U.S. Pat. Nos. 4,683,195, 4,683,202, and 4,800,159). To briefly summarize PCR, nucleic acid primers, complementary to opposite strands of a nucleic acid amplification target nucleic acid sequence, are permitted to anneal to the denatured sample. A DNA polymerase (typically heat stable) extends the DNA duplex from the hybridized primer. The process is repeated to amplify the nucleic acid target. If the nucleic acid primers do not hybridize to the sample, then there is no corresponding amplified PCR product.

In PCR, the nucleic acid probe can be labeled with a tag as discussed before. The detection of the duplex is done using at least one primer directed to the target nucleic acid. In yet another embodiment of PCR, the detection of the hybridized duplex comprises electrophoretic gel separation followed by dye-based visualization.

Nucleic acid amplification procedures by PCR are well known and are described in U.S. Pat. No. 4,683,202. Briefly, the primers anneal to the target nucleic acid at sites distinct from one another and in an opposite orientation. A primer annealed to the target sequence is extended by the enzymatic action of a heat stable polymerase. The extension product is then denatured from the target sequence by heating, and the process is repeated. Successive cycling of this procedure on both strands provides exponential amplification of the region flanked by the primers.

Amplification is then performed using a PCR-type technique, that is to say the PCR technique or any other related technique. Two primers, complementary to the target nucleic acid sequence are then added to the nucleic acid content along with a polymerase, and the polymerase amplifies the DNA region between the primers.

Stem-loop RT-PCR is a PCR method that is useful in the methods of the invention to amplify and quantify miRNAs of interest (See Caifu et al., 2005, Nucleic Acids Research 33:e179; Mestdagh et al., 2008, Nucleic Acids Research 36:e143; Varkonyi-Gasic et al., 2011, Methods Mol Biol. 744:145-57). Briefly, the method includes two steps: RT and real-time PCR. First, a stem-loop RT primer is hybridized to a miRNA molecule and then reverse transcribed with a reverse transcriptase. Then, the RT products are quantified using conventional real-time PCR.

The expression specifically hybridizing in stringent conditions refers to a hybridizing step in the process of the invention where the oligonucleotide sequences selected as probes or primers are of adequate length and sufficiently unambiguous so as to minimize the amount of non-specific binding that may occur during the amplification. The oligonucleotide probes or primers herein described may be prepared by any suitable methods such as chemical synthesis methods.

Hybridization is typically accomplished by annealing the oligonucleotide probe or primer to the template nucleic acid under conditions of stringency that prevent non-specific binding but permit binding of this template nucleic acid which has a significant level of homology with the probe or primer.

Among the conditions of stringency is the melting temperature (Tm) for the amplification step using the set of primers, which is in the range of about 50° C. to about 95° C. Typical hybridization and washing stringency conditions depend in part on the size (i.e., number of nucleotides in length) of the template nucleic acid or the oligonucleotide probe, the base composition and monovalent and divalent cation concentrations (Ausubel et al., 1994, eds Current Protocols in Molecular Biology).

In one embodiment, the process for determining the quantitative and qualitative profile according to the present invention is characterized in that the amplifications are real-time amplifications performed using a labeled probe, for example, a labeled hydrolysis-probe, capable of specifically hybridizing in stringent conditions with a segment of a nucleic acid sequence, or polymorphic nucleic acid sequence. The labeled probe is capable of emitting a detectable signal every time each amplification cycle occurs.

The real-time amplification, such as real-time PCR, is well known in the art, and the various known techniques will be employed in the best way for the implementation of the present process. These techniques are performed using various categories of probes, such as hydrolysis probes, hybridization adjacent probes, or molecular beacons. The techniques employing hydrolysis probes or molecular beacons are based on the use of a fluorescence quencher/reporter system, and the hybridization adjacent probes are based on the use of fluorescence acceptor/donor molecules.

Hydrolysis probes with a fluorescence quencher/reporter system are available in the market, and are for example commercialized by the Applied Biosystems group (USA). Many fluorescent dyes may be employed, such as FAM dyes (6-carboxy-fluorescein), or any other dye phosphoramidite reagents.

Among the stringent conditions applied for any one of the hydrolysis-probes of the present invention is the Tm, which is in the range of about 50° C. to 95° C. As an example, the Tm for any one of the hydrolysis-probes of the present invention is in the range of about 55° C. to about 80° C. As an example, the Tm applied for any one of the hydrolysis-probes of the present invention is about 75° C.

In another embodiment, the process for determining the quantitative and qualitative profile according to the present invention is characterized in that the amplification products can be elongated, wherein the elongation products are separated relative to their length. The signal obtained for the elongation products is measured, and the quantitative and qualitative profile of the labeling intensity relative to the elongation product length is established.

The elongation step, also called a run-off reaction, allows one to determine the length of the amplification product. The length can be determined using conventional techniques, for example, using gels such as polyacrylamide gels for the separation, DNA sequencers, and adapted software. Because some mutations display length heterogeneity, some mutations can be determined by a change in length of elongation products.

In one aspect, the invention includes a primer that is complementary to a nucleic acid sequence of the miRNA of interest, and more particularly the primer includes 12 or more contiguous nucleotides substantially complementary to the sequence of the miRNA of interest. For example, a primer featured in the invention includes a nucleotide sequence sufficiently complementary to hybridize to a nucleic acid sequence of about 12 to 25 nucleotides. For example, the primer differs by no more than 1, 2, or 3 nucleotides from the target nucleotide sequence. In another aspect, the length of the primer can vary in length, for example about 15 to 28 nucleotides in length (e.g., 15, 16, 17, 18, 19, 20, 21, 22, 23, 24, 25, 26, 27 or 28 nucleotides in length).

Determining Effectiveness of Therapy or Prognosis

In one aspect, the level of one or more circulating miRNAs in a biological sample of a patient is used to monitor the effectiveness of treatment or the prognosis of disease. In some embodiments, the level of one or more circulating miRNAs in a test sample obtained from a treated patient can be compared to the level from a reference sample obtained from that patient prior to initiation of a treatment. Clinical monitoring of treatment typically entails that each patient serve as his or her own baseline control. In some embodiments, test samples are obtained at multiple time points following administration of the treatment. In these embodiments, measurement of level of one or more circulating miRNAs in the test samples provides an indication of the extent and duration of in vivo effect of the treatment.

Measurement of biomarker levels allow for the course of treatment of a disease to be monitored. The effectiveness of a treatment regimen for a disease can be monitored by detecting one or more biomarkers in an effective amount from samples obtained from a subject over time and comparing the amount of biomarkers detected. For example, a first sample can be obtained prior to the subject receiving treatment and one or more subsequent samples are taken after or during treatment of the subject. Changes in biomarker levels across the samples may provide an indication as to the effectiveness of the therapy.

In one embodiment, the invention provides a method for monitoring the levels of miRNAs in response to treatment. For example, in some embodiments, the invention provides for a method of determining the efficacy of treatment in a subject, by measuring the levels of one or more miRNAs described herein. In one embodiment, the level of the one or more miRNAs can be measured over time, where the level at one timepoint after the initiation of treatment is compared to the level at another timepoint after the initiation of treatment. In one embodiment, the level of the one or more miRNAs can be measured over time, where the level at one timepoint after the initiation of treatment is compared to the level prior to the initiation of treatment.

In one embodiment, the invention provides a method for monitoring at least one of miR-320a, miR-376a, miR-140, miR-107, miR-212, miR-499, miR-375, miR-589, miR-15b, miR-106b, miR-185, let-7f, miR-144, miR-34a, miR-16, miR-26b, miR-18a, miR-29, miR-146b, miR-221, miR-143, miR-199a, miR-374b, miR-20b, miR-381, miR-487b, miR-203, miR-301a, miR-129, miR-331, miR-486, miR-15a, miR-98, miR-152, miR-190, miR-133, miR-135b, miR-100, miR-99a, miR-155, let-7b, miR-30, miR-126, miR-342, miR-181d, miR-132, miR-150, miR-511, miR-671, miR-433, miR-128, miR-451, miR-99b, miR-28, miR-517a, let-7d, miR-370, miR-224, miR-31, miR-22, miR-10b, miR-429, miR-181a, miR-33, miR-200, miR-222, miR-21, miR-26a, miR-503, miR-27, miR-493, miR-136, miR-654, miR-758, miR-432, miR-1275, miR-193b-365, miR-17, miR-20a, miR-378, miR-519d, miR-355, miR-148a, miR-1247, miR-3124, miR-1343, miR-191, miR-210, miR-19b, miR-92a, let-7c, miR-335, miR-19a, miR-146a, miR-880, miR-295, miR-302d, miR-291a, miR-744, miR-208, miR-712, miR-205, miR-101a, miR-10a, miR-145, miR-1, miR-181b, and let-7g after treatment.

In one embodiment, the invention provides a method for monitoring a HRD treatment or assessing the efficacy of a HRD treatment. For example, in one embodiment, the method indicates that a treatment for atherosclerosis is effective when the level of at least one of miR-880, miR-295, miR-302d, miR-291a, miR-744, miR-208, miR-712, miR-205, miR-200, miR-222, miR-210, let-7c, miR-19b, miR092a, miR-29, miR-144, miR-34a, miR-126, miR-155, miR-342, miR-221, and miR-21 is decreased in a sample of a treated subject as compared to a comparator control. In one embodiment, the method indicates that the treatment is effective when the level of at least one of miR-133, miR-101a, miR-10a, miR-145, miR-1, miR-181b, let-7g, miR-143, miR-199a, miR-26a, let-7b, miR-19a, miR-146a, and miR-335 is increased in a sample of a treated subject as compared to a comparator control. In one embodiment, the comparator control is a sample from a diseased subject not receiving treatment, a sample from the subject obtained at an earlier time point during treatment, or a level in a population of diseased subjects not receiving treatment.

In one embodiment, the method indicates that a treatment for T2DM/IR is effective when the level of at least one of miR-320a, miR-376a, miR-140, miR-107, miR-212, miR-499, miR-375, miR-589, miR-15b, miR-106b, miR-185, let-7f, miR-144, miR-34a, miR-16, miR-26b, miR-18a, miR-29, miR-146b, miR-221, miR-143 and miR-199a is decreased in a sample of a treated subject as compared to a comparator control. In one embodiment, the method indicates that the treatment is effective when the level of at least one of miR-374b, miR-20b, miR-381, miR-487b, miR-203, miR-301a, miR-129, miR-331, miR-486, miR-15a, miR-98, miR-152, miR-190, miR-133, miR-135b, miR-100, miR-99a, miR-155, let-7b, miR-30, miR-126 and miR-342 is increased in a sample of a treated subject as compared to a comparator control. In one embodiment, the comparator control is a sample from a diseased subject not receiving treatment, a sample from the subject obtained at an earlier time point during treatment, or a level in a population of diseased subjects not receiving treatment.

In one embodiment, the method indicates that a treatment for NAFLD is effective when the level of at least one of miR-370, miR-224, miR-31, miR-22, miR-10b, miR-429, miR-181a, miR-33, miR-200, miR-222, miR-146b, miR-34a, miR-16, miR-221, let-7b and miR-26a is decreased in a sample of a treated subject as compared to a comparator control. In one embodiment, the method indicates that the treatment is effective when the level of at least one of miR-181d, miR-132, miR-150, miR-511, miR-671, miR-433, miR-128, miR-451, miR-99b, miR-28, miR-517a, let-7d, miR-155, miR-21 and miR-99a is increased in a sample of a treated subject as compared to a comparator control. In one embodiment, the comparator control is a sample from a diseased subject not receiving treatment, a sample from the subject obtained at an earlier time point during treatment, or a level in a population of diseased subjects not receiving treatment.

In one embodiment, the method indicates that a treatment for obesity is effective when the level of at least one of miR-17, miR-20a, miR-378, miR-519d, miR-355, miR-148a, miR-1247, miR-3124, miR-1343, miR-191, miR-30, miR-21, miR-19a, miR-146a, miR-26b, miR-18a, miR-210, miR-19b, miR-92a, miR-29, miR-146b, let-7c and miR-335 is decreased in a sample of a treated subject as compared to a comparator control. In one embodiment, the method indicates that the treatment is effective when the level of at least one of miR-155, miR-221, miR-503, miR-27, miR-493, miR-136, miR-654, miR-758, miR-432, miR-1275, miR-193b-365, miR-135b, and miR-100 is increased in a sample of a treated subject as compared to a comparator control. In one embodiment, the comparator control is a sample from a diseased subject not receiving treatment, a sample from the subject obtained at an earlier time point during treatment, or a level in a population of diseased subjects not receiving treatment.

To identify therapeutics or drugs that are appropriate for a specific subject, a test sample from the subject can also be exposed to a therapeutic agent or a drug, and the level of one or more biomarkers can be determined. Biomarker levels can be compared to a sample derived from the subject before and after treatment or exposure to a therapeutic agent or a drug, or can be compared to samples derived from one or more subjects who have shown improvements relative to a disease as a result of such treatment or exposure. Thus, in one aspect, the invention provides a method of assessing the efficacy of a therapy with respect to a subject comprising taking a first measurement of a biomarker panel in a first sample from the subject; effecting the therapy with respect to the subject; taking a second measurement of the biomarker panel in a second sample from the subject and comparing the first and second measurements to assess the efficacy of the therapy.

Additionally, therapeutic agents suitable for administration to a particular subject can be identified by detecting one or more biomarkers in an effective amount from a sample obtained from a subject and exposing the subject-derived sample to a test compound that determines the amount of the biomarker(s) in the subject-derived sample. Accordingly, treatments or therapeutic regimens for use in subjects having a HRD can be selected based on the amounts of biomarkers in samples obtained from the subjects and compared to a reference value. Two or more treatments or therapeutic regimens can be evaluated in parallel to determine which treatment or therapeutic regimen would be the most efficacious for use in a subject to delay onset, or slow progression of a disease. In various embodiments, a recommendation is made on whether to initiate or continue treatment of a disease.

A prognosis may be expressed as the amount of time a patient can be expected to survive. Alternatively, a prognosis may refer to the likelihood that the disease goes into remission or to the amount of time the disease can be expected to remain in remission. Prognosis can be expressed in various ways; for example, prognosis can be expressed as a percent chance that a patient will survive after one year, five years, ten years or the like. Alternatively, prognosis may be expressed as the number of years, on average that a patient can expect to survive as a result of a condition or disease. The prognosis of a patient may be considered as an expression of relativism, with many factors affecting the ultimate outcome. For example, for patients with some conditions, prognosis can be appropriately expressed as the likelihood that a condition may be treatable or curable, or the likelihood that a disease will go into remission, whereas for patients with more severe conditions prognosis may be more appropriately expressed as likelihood of survival for a specified period of time. Additionally, a change in a clinical factor from a baseline level may impact a patient's prognosis, and the degree of change in level of the clinical factor may be related to the severity of adverse events. Statistical significance is often determined by comparing two or more populations, and determining a confidence interval and/or a p value.

Multiple determinations of circulating miRNA levels can be made, and a temporal change in activity can be used to determine a prognosis. For example, comparative measurements are made of the circulating miRNA of an acellular body fluid in a patient at multiple time points, and a comparison of a circulating miRNA value at two or more time points may be indicative of a particular prognosis.

In some embodiments, the levels of activity of one or more circulating miRNAs are used as indicators of an unfavorable prognosis. According to the method, the determination of prognosis can be performed by comparing the measured circulating miRNA level to levels determined in comparable samples from healthy individuals or to levels known to corresponding with favorable or unfavorable outcomes. The circulating miRNA levels obtained may depend on a number of factors, including, but not limited to, the laboratory performing the assays, the assay methods used, the type of body fluid sample used and the type of disease a patient is afflicted with. According to the method, values can be collected from a series of patients with a particular disorder to determine appropriate reference ranges of circulating miRNA for that disorder. One of ordinary skill in the art is capable of performing a retrospective study that compares the determined levels to the observed outcome of the patients and establishing ranges of levels that can be used to designate the prognosis of the patients with a particular disorder. For example, levels in the lowest range would be indicative of a more favorable prognosis, while circulating miRNA levels in the highest ranges would be indicative of an unfavorable prognosis. Thus, in this aspect the term "elevated levels" refers to levels of that are above the range of the reference value. In some embodiments patients with "high" or "elevated" levels have levels that are higher than the median activity in a population of patients with that disease. In some embodiments, "high" or "elevated" levels for a patient with a particular disease refers to levels that are above the median values for patients with that disorder and are in the upper 40% of patients with the disorder, or to levels that are in the upper 20% of patients with the disorder, or to levels that are in the upper 10% of patients with the disorder, or to levels that are in the upper 5% of patients with the disorder.

Because the level of circulating miRNA in a test sample from a patient relates to the prognosis of a patient in a continuous fashion, the determination of prognosis can be performed using statistical analyses to relate the determined circulating miRNA levels to the prognosis of the patient. A skilled artisan is capable of designing appropriate statistical methods. For example, the methods may employ the chi-squared test, the Kaplan-Meier method, the log-rank test, multivariate logistic regression analysis, Cox's proportional-hazard model and the like in determining the prognosis. Computers and computer software programs may be used in organizing data and performing statistical analyses.

The approach by Giles et. al., British Journal of Hemotology, 121:578-585, is exemplary. As in Giles et al., associations between categorical variables (e.g., miRNA levels and clinical characteristics) can be assessed via cross-tabulation and Fisher's exact test. Unadjusted survival probabilities can be estimated using the method of Kaplan and Meier. The Cox proportional hazards regression model also can be used to assess the ability of patient characteristics (such as miRNA levels) to predict survival, with 'goodness of fit' assessed by the Grambsch-Therneau test, Schoenfeld residual plots, martingale residual plots and likelihood ratio statistics (see Grambsch et al, 1995). In some embodiments, this approach can be adapted as a simple computer program that can be used with personal computers or personal digital assistants (PDA). The prediction of patients' survival time based on their circulating miRNA levels can be performed via the use of a visual basic for applications (VBA) computer program developed within Microsoft Excel. The core construction and analysis may be based on the Cox proportional hazard models. The VBA application can be developed by obtaining a base hazard rate and parameter estimates. These statistical analyses can be performed using a statistical program such as the SAS proportional hazards regression, PHREG, procedure. Estimates can then be used to obtain probabilities of surviving from one to 24 months given the patient's covariates. The program can make use of estimated probabilities to create a graphical representation of a given patient's predicted survival curve. In some embodiments, the program also provides 6-month, 1-year and 18-month survival probabilities. A graphical interface can be used to input patient characteristics in a user-friendly manner. In some embodiments of the invention, multiple prognostic factors, including circulating miRNA level, are considered when determining the prognosis of a patient. For example, the prognosis of a patient may be determined based on circulating miRNA and one or more prognostic factors selected from the group consisting of cytogenetics, performance status, age, gender and previous diagnosis. In some embodiments, other prognostic factors may be combined with the circulating miRNA level or other biomarkers in the algorithm to determine prognosis with greater accuracy.

Treatment Methods

The present invention provides therapeutic molecules for the treatment or prevention of HRD or an associated disease or disorder. Diseases or disorders that can be treated according to the methods of the invention include, but are not limited to, obesity, diabetes mellitus, NAFLD, liver cirrhosis, atherosclerosis, and cancer, including but not limited to colorectal cancer (CRC), hepatocellular carcinoma (HCC), breast cancer, pancreatic cancer, endometrial cancer, renal cell carcinoma (RCC), prostate cancer, ovarian cancer, and lung cancer. In one embodiment, the therapeutic molecules include but are not limited to inhibitors, activators, and modulators of the markers of the invention. For example, if a gene or miRNA is downregulated in HRD, then it would be desirable to increase the expression of the downregulated gene or miRNA to normal levels using an activator as a form of therapy. Activators are compounds that increase, open, activate, facilitate, enhance activation, sensitize, agonize, or up regulate activity of HRD biomarkers. Alternatively, if a gene or miRNA is upregulated in HRD, then it would be desirable to decrease the expression of the upregulated gene or miRNA to normal levels using an inhibitor as a form of therapy. Inhibitors are compounds that, e.g., bind to, partially or totally block activity, decrease, prevent, delay activation, inactivate, desensitize, or down regulate the activity or expression of HRD biomarkers.

Methods and materials for increasing or decreasing the expression levels of the markers of the present invention are well known and within the skill of a person in the art. A non-limiting list of known methods and materials includes: physical therapy, diet, vitamins, dietary supplements, gene therapy methods, antisense oligonucleotides, antagomirs, drugs and hormonal medications.

The invention provides a method of treating a HRD by targeting the miRNAs described herein. For example, in one embodiment, the invention provides a method of treating atherosclerosis in a subject comprising administering an agent that increases the expression, activity, or level of one more miRNAs described herein. For example, in one embodiment, the method comprises administering an agent that increases the expression or level of at least one of miR-133, miR-101a, miR-10a, miR-145, miR-1, miR-181b, let-7g, miR-143, miR-199a, miR-26a, let-7b, miR-19a, miR-146a, and miR-335. In one embodiment, the invention provides a method of treating atherosclerosis in a subject comprising administering an agent that decreases the expression or level of one more miRNAs described herein. For example, in one embodiment, the method comprises administering an agent that decreases the expression or level of at least one of miR-880, miR-295, miR-302d, miR-291a, miR-744, miR-208, miR-712, miR-205, miR-200, miR-222, miR-210, let-7c, miR-19b, miR092a, miR-29, miR-144, miR-34a, miR-126, miR-155, miR-342, miR-221, and miR-21. In various embodiments, the agent that modulates one or more miRNAs to treat atherosclerosis is at least one of an antisense nucleic acid, a ribozyme, a nucleic acid molecule, a polypeptide, an antibody, and a small molecule.

In one embodiment, the invention provides a method of treating T2DM/IR in a subject comprising administering an agent that increases the expression, activity, or level of one more miRNAs described herein. For example, in one embodiment, the method comprises administering an agent that increases the expression or level of at least one of miR-374b, miR-20b, miR-381, miR-487b, miR-203, miR-301a, miR-129, miR-331, miR-486, miR-15a, miR-98, miR-152, miR-190, miR-133, miR-135b, miR-100, miR-99a, miR-155, let-7b, miR-30, miR-126 and miR-342. In one embodiment, the invention provides a method of treating T2DM/IR in a subject comprising administering an agent that decreases the expression or level of one more miRNAs described herein. For example, in one embodiment, the method comprises administering an agent that decreases the expression or level of at least one of miR-320a, miR-376a, miR-140, miR-107, miR-212, miR-499, miR-375, miR-589, miR-15b, miR-106b, miR-185, let-7f, miR-144, miR-34a, miR-16, miR-26b, miR-18a, miR-29, miR-146b, miR-221, miR-143 and miR-199a. In various embodiments, the agent that modulates one or more miRNAs to treat T2DM/IR is at least one of an antisense nucleic acid, a ribozyme, a nucleic acid molecule, a polypeptide, an antibody, and a small molecule.

In one embodiment, the invention provides a method of treating NAFLD in a subject comprising administering an agent that increases the expression, activity, or level of one more miRNAs described herein. For example, in one embodiment, the method comprises administering an agent that increases the expression or level of at least one of miR-181d, miR-132, miR-150, miR-511, miR-671, miR-433, miR-128, miR-451, miR-99b, miR-28, miR-517a, let-7d, miR-155, miR-21 and miR-99a. In one embodiment, the invention provides a method of treating NAFLD in a subject comprising administering an agent that decreases the expression or level of one more miRNAs described herein. For example, in one embodiment, the method comprises administering an agent that decreases the expression or level of at least one of miR-370, miR-224, miR-31, miR-22, miR-10b, miR-429, miR-181a, miR-33, miR-200, miR-222, miR-146b, miR-34a, miR-16, miR-221, let-7b and miR-26a. In various embodiments, the agent that modulates one or more miRNAs to treat NAFLD is at least one of an antisense nucleic acid, a ribozyme, a nucleic acid molecule, a polypeptide, an antibody, and a small molecule.

In one embodiment, the invention provides a method of treating obesity in a subject comprising administering an agent that increases the expression, activity, or level of one more miRNAs described herein. For example, in one embodiment, the method comprises administering an agent that increases the expression or level of at least one of miR-155, miR-221, miR-503, miR-27, miR-493, miR-136, miR-654, miR-758, miR-432, miR-1275, miR-193b-365, miR-135b, and miR-100. In one embodiment, the invention provides a method of treating obesity in a subject comprising administering an agent that decreases the expression or level of one more miRNAs described herein. For example, in one embodiment, the method comprises administering an agent that decreases the expression or level of at least one of miR-17, miR-20a, miR-378, miR-519d, miR-355, miR-148a, miR-1247, miR-3124, miR-1343, miR-191, miR-30, miR-21, miR-19a, miR-146a, miR-26b, miR-18a, miR-210, miR-19b, miR-92a, miR-29, miR-146b, let-7c and miR-335. In various embodiments, the agent that modulates one or more miRNAs to treat obesity is at least one of an antisense nucleic acid, a ribozyme, a nucleic acid molecule, a polypeptide, an antibody, and a small molecule.

In one embodiment, the invention provides a method of treating MHO type I in a subject comprising administering an agent that increases the expression, activity, or level of miR-221. In various embodiments, the agent that modulates one or more miRNAs to treat MHO type I is at least one of an antisense nucleic acid, a ribozyme, a nucleic acid molecule, a polypeptide, an antibody, and a small molecule.

In one embodiment, the invention provides a method of treating MHO type II in a subject comprising administering an agent that increases the expression, activity, or level of at least one of miR-221 and miR-155. In various embodiments, the agent that modulates one or more miRNAs to treat MHO type II is at least one of an antisense nucleic acid, a ribozyme, a nucleic acid molecule, a polypeptide, an antibody, and a small molecule.

In one embodiment, the invention provides a method of treating a combination of atherosclerosis and T2DM/IR in a subject comprising administering an agent that increases the expression, activity, or level of one more miRNAs described herein. For example, in one embodiment, the method comprises administering an agent that increases the expression or level of at least one of let-7b and miR-133. In one embodiment, the invention provides a method of treating a combination of atherosclerosis and T2DM/IR in a subject comprising administering an agent that decreases the expression or level of one more miRNAs described herein. For example, in one embodiment, the method comprises administering an agent that decreases the expression or level of miR-144. In various embodiments, the agent that modulates one or more miRNAs to treat a combination of atherosclerosis and T2DM/IR is at least one of an antisense nucleic acid, a ribozyme, a nucleic acid molecule, a polypeptide, an antibody, and a small molecule.

In one embodiment, the invention provides a method of treating a combination of atherosclerosis and obesity in a subject comprising administering an agent that decreases the expression or level of one more miRNAs described herein. For example, in one embodiment, the method comprises administering an agent that decreases the expression or level of at least one of miR-19b, let-7c, miR-21, miR-92a, and miR-201. In various embodiments, the agent that modulates one or more miRNAs to treat a combination of atherosclerosis and obesity is at least one of an antisense nucleic acid, a ribozyme, a nucleic acid molecule, a polypeptide, an antibody, and a small molecule.

In one embodiment, the invention provides a method of treating a combination of atherosclerosis and NAFLD in a subject comprising administering an agent that decreases the expression or level of one more miRNAs described herein. For example, in one embodiment, the method comprises administering an agent that decreases the expression or level of at least one of miR-200 and miR-222. In various embodiments, the agent that modulates one or more miRNAs to treat a combination of atherosclerosis and NAFLD is at least one of an antisense nucleic acid, a ribozyme, a nucleic acid molecule, a polypeptide, an antibody, and a small molecule.

In one embodiment, the invention provides a method of treating a combination of T2DM/IR and obesity in a subject comprising administering an agent that increases the expression, activity, or level of one more miRNAs described herein. For example, in one embodiment, the method comprises administering an agent that increases the expression or level of at least one of miR-135b and miR-100. In one embodiment, the invention provides a method of treating a combination of T2DM/IR and obesity in a subject comprising administering an agent that decreases the expression or level of one more miRNAs described herein. For example, in one embodiment, the method comprises administering an agent that decreases the expression or level of at least one of miR-26b and miR-18a. In various embodiments, the agent that modulates one or more miRNAs to treat a combination of T2DM/IR and obesity is at least one of an antisense nucleic acid, a ribozyme, a nucleic acid molecule, a polypeptide, an antibody, and a small molecule.

In one embodiment, the invention provides a method of treating a combination of NAFLD and T2DM/IR in a subject comprising administering an agent that increases the expression, activity, or level of one more miRNAs described herein. For example, in one embodiment, the method comprises administering an agent that increases the expression or level of miR-99a. In one embodiment, the invention provides a method of treating a combination of NAFLD and T2DM/IR in a subject comprising administering an agent that decreases the expression or level of one more miRNAs described herein. For example, in one embodiment, the method comprises administering an agent that decreases the expression or level of miR-16. In various embodiments, the agent that modulates one or more miRNAs to treat a combination of NAFLD and T2DM/IR is at least one of an antisense nucleic acid, a ribozyme, a nucleic acid molecule, a polypeptide, an antibody, and a small molecule.

In one embodiment, the invention provides a method of treating a combination of atherosclerosis, obesity and T2DM/IR in a subject comprising administering an agent that decreases the expression or level of one more miRNAs described herein. For example, in one embodiment, the method comprises administering an agent that decreases the expression or level of miR-29. In various embodiments, the agent that modulates one or more miRNAs to treat a combination of atherosclerosis, obesity and T2DM/IR is at least one of an antisense nucleic acid, a ribozyme, a nucleic acid molecule, a polypeptide, an antibody, and a small molecule.

In one embodiment, the invention provides a method of treating a combination of atherosclerosis, NAFLD and T2DM/IR in a subject comprising administering an agent that decreases the expression or level of one more miRNAs described herein. For example, in one embodiment, the method comprises administering an agent that decreases the expression or level of at least one of miR-221 and miR-34. In various embodiments, the agent that modulates one or more miRNAs to treat a combination of atherosclerosis, NAFLD and T2DM/IR is at least one of an antisense nucleic acid, a ribozyme, a nucleic acid molecule, a polypeptide, an antibody, and a small molecule.

In one embodiment, the invention provides a method of treating a combination of atherosclerosis, NAFLD and T2DM/IR in a subject comprising administering an agent that decreases the expression or level of one more miRNAs described herein. For example, in one embodiment, the method comprises administering an agent that decreases the expression or level of miR-149b. In various embodiments, the agent that modulates one or more miRNAs to treat a combination of atherosclerosis, NAFLD and T2DM/IR is at least one of an antisense nucleic acid, a ribozyme, a nucleic acid molecule, a polypeptide, an antibody, and a small molecule.

In one embodiment, the agent is coupled to a moiety that increases cell penetration or solubility of the agent. In one embodiment, the agent is coupled to cholesterol. In another embodiment, the agent is coupled to one or more moieties or combined with one or more compositions that are capable of directing the agent to a specific organ, tissue, or cell type. In some embodiments, the composition comprises a delivery vehicle, including but not limited to, a nanoparticle, microparticle, micelle, polymerosome, and the like, which comprises the agent. In some embodiments, the delivery vehicle is targeted to a specific treatment site, to reduce any possible systemic effects.

Nucleic Acids

Treatment with a miRNA-modulating agent may be carried out using one or more nucleic acid molecules. In some instances the modulator is an siRNA, antagomir, antisense molecule, or CRISPR guide RNA, which modulates the activity of one or more siRNAs associated with HRD. In one embodiment, the nucleic acid comprises a promoter/regulatory sequence such that the nucleic acid is capable of directing expression of the nucleic acid. Thus, the invention encompasses expression vectors and methods for the introduction of exogenous DNA into cells with concomitant expression of the exogenous DNA in the cells such as those described, for example, in Sambrook et al. (2012, Molecular Cloning: A Laboratory Manual, Cold Spring Harbor Laboratory, New York), and in Ausubel et al. (2008, Current Protocols in Molecular Biology, John Wiley & Sons, New York) and as described elsewhere herein. In one embodiment, siRNA is used to decrease the level of one or more siRNAs associated with HRD. RNA interference (RNAi) is a phenomenon in which the introduction of double-stranded RNA (dsRNA) into a diverse range of organisms and cell types causes degradation of the complementary mRNA. In the cell, long dsRNAs are cleaved into short 21-25 nucleotide small interfering RNAs, or siRNAs, by a ribonuclease known as Dicer. The siRNAs subsequently assemble with protein components into an RNA-induced silencing complex (RISC), unwinding in the process. Activated RISC then binds to complementary transcript by base pairing interactions between the siRNA antisense strand and the mRNA. The bound mRNA is cleaved and sequence specific degradation of mRNA results in gene silencing. Soutschek et al. (2004, Nature 432:173-178) describe a chemical modification to siRNAs that aids in intravenous systemic delivery. Optimizing siRNAs involves consideration of overall G/C content, C/T content at the termini, Tm and the nucleotide content of the 3' overhang. See, for instance, Schwartz et al., 2003, Cell, 115:199-208 and Khvorova et al., 2003, Cell 115:209-216. Therefore, the present invention also includes methods of decreasing levels of one or more siRNAs associated with HRD using RNAi technology.

In another aspect, the invention includes a vector comprising an siRNA or antisense polynucleotide. For example, the siRNA or antisense polynucleotide is capable of inhibiting the expression of a target miRNA. The incorporation of a desired polynucleotide into a vector and the choice of vectors is well-known in the art as described in, for example, Sambrook et al., supra, and Ausubel et al., supra, and elsewhere herein.

In some embodiments, the expression vectors described herein encode a short hairpin RNA (shRNA) modulator. shRNA modulators are well known in the art and are directed against the RNA of a target, thereby decreasing the expression of the target. In some embodiments, the encoded shRNA is expressed by a cell, and is then processed into siRNA. For example, in some instances, the cell possesses native enzymes (e.g., dicer) that cleaves the shRNA to form siRNA.

The siRNA, shRNA, or antisense polynucleotide can be cloned into a number of types of vectors as described elsewhere herein. For expression of the siRNA or antisense polynucleotide, at least one module in each promoter functions to position the start site for RNA synthesis.

In order to assess the expression of the siRNA, shRNA, or antisense polynucleotide, the expression vector to be introduced into a cell can also contain either a selectable marker gene or a reporter gene or both to facilitate identification and selection of expressing cells from the population of cells sought to be transfected or infected using a viral vector. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neomycin resistance and the like.

Therefore, in another aspect, the invention relates to a vector, comprising the nucleotide sequence of the invention or the construct of the invention. The choice of the vector will depend on the host cell in which it is to be subsequently introduced. In a particular embodiment, the vector of the invention is an expression vector. Suitable host cells include a wide variety of prokaryotic and eukaryotic host cells. In specific embodiments, the expression vector is selected from the group consisting of a viral vector, a bacterial vector and a mammalian cell vector. Prokaryote- and/or eukaryote-vector based systems can be employed for use with the present invention to produce polynucleotides, or their cognate polypeptides. Many such systems are commercially and widely available.

Further, the expression vector may be provided to a cell in the form of a viral vector. Viral vector technology is well known in the art and is described, for example, in Sambrook et al., and in Ausubel et al., and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193.

Vectors suitable for the insertion of the polynucleotides are vectors derived from expression vectors in prokaryotes such as pUC18, pUC19, Bluescript and the derivatives thereof, mp18, mp19, pBR322, pMB9, ColE1, pCR1, RP4, phages and "shuttle" vectors such as pSA3 and pAT28, expression vectors in yeasts such as vectors of the type of 2 micron plasmids, integration plasmids, YEP vectors, centromere plasmids and the like, expression vectors in insect cells such as vectors of the pAC series and of the pVL, expression vectors in plants such as pIBI, pEarleyGate, pAVA, pCAMBIA, pGSA, pGWB, pMDC, pMY, pORE series and the like, and expression vectors in eukaryotic cells based on viral vectors (adenoviruses, viruses associated to adenoviruses such as retroviruses and, particularly, lentiviruses) as well as non-viral vectors such as pSilencer 4.1-CMV (Ambion), pcDNA3, pcDNA3.1/hyg, pHMCV/Zeo, pCR3.1, pEFI/His, pIND/GS, pRc/HCMV2, pSV40/Zeo2, pTRACER-HCMV, pUB6/V5-His, pVAX1, pZeoSV2, pCI, pSVL and PKSV-10, pBPV-1, pML2d and pTDT1.

By way of illustration, the vector in which the nucleic acid sequence is introduced can be a plasmid which is or is not integrated in the genome of a host cell when it is introduced in the cell. Illustrative, non-limiting examples of vectors in which the nucleotide sequence of the invention or the gene construct of the invention can be inserted include a tet-on inducible vector for expression in eukaryote cells.

The vector may be obtained by conventional methods known by persons skilled in the art (Sambrook et al.). In a particular embodiment, the vector is a vector useful for transforming animal cells.

In one embodiment, the recombinant expression vectors may also contain nucleic acid molecules which encode a peptide or peptidomimetic modulator of the invention, described elsewhere herein.

Additional promoter elements, i.e., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either co-operatively or independently to activate transcription.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, some advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (U.S. Pat. Nos. 4,683,202, 5,928, 906). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al. The promoters employed may be constitutive, tissue-specific, inducible, and/or useful under the appropriate conditions to direct high level expression of the introduced DNA segment. The promoter may be heterologous or endogenous.

A promoter sequence exemplified in the experimental examples presented herein is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, Moloney virus promoter, the avian leukemia virus promoter, Epstein-Barr virus immediate early promoter, Rous sarcoma virus promoter, as well as human gene promoters such as, but not limited to, the actin promoter, the myosin promoter, the hemoglobin promoter, and the muscle creatine promoter. Further, the invention should not be limited to the use of constitutive promoters. Inducible promoters are also contemplated as part of the invention. The use of an inducible promoter in the invention provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. Further, the invention includes the use of a tissue specific promoter, which promoter is active only in a desired tissue (e.g., skin). Tissue specific promoters are well known in the art and include, but are not limited to, the keratin 14 promoter and the fascin promoter sequences.

In a particular embodiment, the expression of the nucleic acid is externally controlled. In a more particular embodiment, the expression is externally controlled using the doxycycline Tet-On system.

The recombinant expression vectors may also contain a selectable marker gene which facilitates the selection of transformed or transfected host cells. Suitable selectable marker genes are genes encoding proteins such as G418 and hygromycin which confer resistance to some drugs, β-galactosidase, chloramphenicol acetyltransferase, firefly luciferase, or an immunoglobulin or portion thereof such as the Fc portion of an immunoglobulin, for example, an IgG. The selectable markers may be introduced on a separate vector from the nucleic acid of interest.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. Expression of the reporter gene is assayed at a suitable time after the DNA has been introduced into the recipient cells.

Suitable reporter genes may include genes encoding luciferase, beta-galactosidase, chloramphenicol acetyl transferase, secreted alkaline phosphatase, or the green fluorescent protein gene (see, e.g., Ui-Tei et al., 2000 FEBS Lett. 479:79-82). Suitable expression systems are well known and may be prepared using well known techniques or obtained commercially. Internal deletion constructs may be generated using unique internal restriction sites or by partial digestion of non-unique restriction sites. Constructs may then be transfected into cells that display high levels of siRNA polynucleotide and/or polypeptide expression. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Recombinant expression vectors may be introduced into host cells to produce a recombinant cell. The cells can be prokaryotic or eukaryotic. The vector of the invention can be used to transform eukaryotic cells such as yeast cells, Saccharomyces cerevisiae, or mammal cells for example epithelial kidney 293 cells or U2OS cells, or prokaryotic cells such as bacteria, Escherichia coli or Bacillus subtilis, for example. Nucleic acid can be introduced into a cell using conventional techniques such as calcium phosphate or calcium chloride co-precipitation, DEAE-dextran-mediated transfection, lipofectin, electroporation or microinjection. Suitable methods for transforming and transfecting host cells may be found in Sambrook et al. (Molecular Cloning: A Laboratory Manual, 2nd Edition, Cold Spring Harbor Laboratory press (1989)), and other laboratory textbooks.

Following the generation of the siRNA polynucleotide, a skilled artisan will understand that the siRNA polynucleotide will have some characteristics that can be modified to improve the siRNA as a therapeutic compound. Therefore, the siRNA polynucleotide may be further designed to resist degradation by modifying it to include phosphorothioate, or other linkages, methylphosphonate, sulfone, sulfate, ketyl, phosphorodithioate, phosphoramidate, phosphate esters, and the like (see, e.g., Agrwal et al., 1987 Tetrahedron Lett. 28:3539-3542; Stec et al., 1985 Tetrahedron Lett. 26:2191-2194; Moody et al., 1989 Nucleic Acids Res. 12:4769-4782; Eckstein, 1989 Trends Biol. Sci. 14:97-100; Stein, In: Oligodeoxynucleotides. Antisense Inhibitors of Gene Expression, Cohen, ed., Macmillan Press, London, pp. 97-117 (1989)).

Any polynucleotide may be further modified to increase its stability in vivo. Possible modifications include, but are not limited to, the addition of flanking sequences at the 5' and/or 3' ends; the use of phosphorothioate or 2' O-methyl rather than phosphodiester linkages in the backbone; and/or the inclusion of nontraditional bases such as inosine, queosine, and wybutosine and the like, as well as acetyl-methyl-, thio- and other modified forms of adenine, cytidine, guanine, thymine, and uridine.

In one embodiment of the invention, an antisense nucleic acid sequence which is expressed by a plasmid vector is used to inhibit the expression of one or more siRNAs associated with HRD. The antisense expressing vector is used to transfect a mammalian cell or the mammal itself, thereby causing reduced endogenous expression of one or more siRNAs associated with HRD.

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262:40). In the cell, antisense nucleic acids hybridize to the corresponding mRNA, forming a double-stranded molecule thereby inhibiting the translation of genes.

The use of antisense methods to inhibit the translation of genes is known in the art, and is described, for example, in Marcus-Sakura (1988, Anal. Biochem. 172:289). Such antisense molecules may be provided to the cell via genetic expression using DNA encoding the antisense molecule as taught by Inoue, 1993, U.S. Pat. No. 5,190,931.

Alternatively, antisense molecules of the invention may be made synthetically and then provided to the cell. Antisense oligomers of between about 10 to about 30, for example about 15 nucleotides may be used, since they are easily synthesized and introduced into a target cell. Synthetic antisense molecules contemplated by the invention include oligonucleotide derivatives known in the art which have improved biological activity compared to unmodified oligonucleotides (see U.S. Pat. No. 5,023,243).

Compositions and methods for the synthesis and expression of antisense nucleic acids are as described elsewhere herein.

Ribozymes and their use for inhibiting gene expression are also well known in the art (see, e.g., Cech et al., 1992, J. Biol. Chem. 267:17479-17482; Hampel et al., 1989, Biochemistry 28:4929-4933; Eckstein et al., International Publication No. WO 92/07065; Altman et al., U.S. Pat. No. 5,168,053). Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, J. Amer. Med. Assn. 260:3030). A major advantage of this approach is the fact that ribozymes are sequence-specific.

There are two basic types of ribozymes, namely, tetrahymena-type (Hasselhoff, 1988, Nature 334:585) and hammerhead-type. Tetrahymena-type ribozymes recognize sequences which are four bases in length, while hammerhead-type ribozymes recognize base sequences 11-18 bases in length. The longer the sequence, the greater the likelihood that the sequence will occur exclusively in the target mRNA species.

In one embodiment of the invention, a ribozyme is used to inhibit one or more siRNAs associated with HRD. Ribozymes useful for inhibiting the expression of a target molecule may be designed by incorporating target sequences into the basic ribozyme structure which are complementary, for example, to the miRNA sequence being targeted. Ribozymes targeting one or more siRNAs associated with HRD may be synthesized using commercially available reagents (Applied Biosystems, Inc., Foster City, Calif.) or they may be genetically expressed from DNA encoding them.

In a particular embodiment, the oligonucleotides of the instant invention comprise modified bases such that the oligonucleotides retain their ability to bind other nucleic acid sequences, but are unable to associate significantly with proteins such as the miRNA degradation machinery. In one embodiment, the invention contemplates the use of previously described oligonucleotides known as "Locked Nucleic Acids" (LNAs), as described in WO 99/14226 and U.S. Pat. No. 6,268,490. LNAs are not required, and are an exemplary embodiment within the scope of the invention. In accordance with the present invention the means to identify effective LNAs for use in the methods to increase gene expression are disclosed. For increased nuclease resistance and/or binding affinity to the target, the oligonucleotide agents featured in the invention can also include 2'-O-methyl, 2'-fluorine, 2'-O-methoxyethyl, 2'-O-aminopropyl, 2'-amino, and/or phosphorothioate linkages and the like, as disclosed in Uhlmann et al., Chemical Review, 90: 544-584 (1990). Inclusion of LNAs, ethylene nucleic acids (ENAS), e.g., 2'-4'-ethylene-bridged nucleic acids, and certain nucleobase modifications such as 2-amino-A, 2-thio (e.g., 2-thio-U), G-clamp modifications, can also increase binding affinity to the target.

The exemplary LNA modification of DNA consists of the addition of a methylene bridge which connects the 2'-O (oxygen) to the 4'-C (carbon) in the ribose ring of a nucleic acid. This modification provides valuable improvements to oligonucleotides in regard to affinity and specificity to complementary DNA and RNA oligomers, and greatly increases the stability of DNA oligonucleotides in vitro and in vitro because the oligonucleotide is resistant to enzyme degradation. In addition, the LNA modification increases the affinity for target gene sequences. LNA oligonucleotides are highly selective for antisense sequences, and also lack toxicity. The compositions contemplated throughout this application are synthetic, stable, single-stranded oligonucleotides. In particular, LNA-modified oligonucleotides are also referred to herein as "MRE-concealing LNAs" which are also technically "DNA-LNA mixmers."

In another embodiment of the invention, the MRE-concealing LNAs can be made cell permeable through conjugation to a cholesterol moiety, also known to the skilled artisan as an antagomir. Antagomirs are small oligonucleotides that interfere with miRNA activity, and which can be used to target miRNAs that are upregulated in a HRD or disorder. This addition to the LNA oligonucleotide eliminates the need for transfection or other vector delivery methods while improving stability and distribution. The oligonucleotide antagomir can further be in isolated form or can be part of a pharmaceutical composition used for the methods described herein, particularly as a pharmaceutical composition formulated for parental administration. The pharmaceutical compositions can contain one or more oligonucleotide agents, and in some embodiments, will contain two or more oligonucleotide agents, each one directed to a different miRNA.

An antagomir that is substantially complementary to a nucleotide sequence of an MRE can be delivered to a cell or a human to reduce the activity of an endogenous miRNA (e.g., miRNA of an endogenous gene) by creating a competition for binding to a MRE on an mRNA. This is particularly useful in cases when sufficient translation of a target mRNA is blocked by the miRNA. In one embodiment, an antagomir featured in the invention has a nucleotide sequence that is substantially homologous to one or more miRNAs described herein.

The MRE-concealing LNAs is designed as antisense to a specific MRE which allows for selective up-regulation of a target mRNA. In this way, other mRNA-miRNA interactions can still occur in the cell which would target the transcript for degradation by RNase. The oligonucleotides occupy the MRE which prevents miRNA mediated-degradation of the mRNA transcript prior to translation.

An mRNA transcribed from the target gene hybridizes to a miRNA, which consequently results in down-regulation of mRNA expression. An antagomir featured in the invention hybridizes to the MRE which results in an increase in mRNA expression. In the case of a whole organism, the method can be used to increase expression of a gene and treat a condition associated with a low level of expression of a gene. Accordingly this method allows for the blocking of miRNA activity on a single target gene, and given that miRNAs regulate the expression of the majority of genes, this invention has broad applications for therapy. In one embodiment, the composition comprising an antagomir is administered locally. In another embodiment, the composition comprising an antagomir is administered systemically. In various embodiments, the antagomir reduces the level, expression, or activity of one or more miRNAs that are associated with a HRD or disorder.

Polypeptides

Treatment with a miRNA-modulating agent may be carried out using one or more polypeptides. The invention includes an isolated peptide modulator that activates or inhibits one or more miRNAs associated with a HRD. For example, in one embodiment, the peptide modulator of the invention modulates miRNAs directly by binding to miRNAs thereby altering the normal functional activity of miRNAs. For example in one embodiment, the peptide modulator of the invention modulates miRNAs indirectly by binding and altering a regulator of one or more miRNAs associated with a HRD.

The variants of the polypeptides according to the present invention may be (i) one in which one or more of the amino acid residues are substituted with a conserved or non-conserved amino acid residue (e.g., a conserved amino acid residue) and such substituted amino acid residue may or may not be one encoded by the genetic code, (ii) one in which there are one or more modified amino acid residues, e.g., residues that are modified by the attachment of substituent groups, (iii) one in which the polypeptide is an alternative splice variant of the polypeptide of the present invention, (iv) fragments of the polypeptides and/or (v) one in which the polypeptide is fused with another polypeptide, such as a leader or secretory sequence or a sequence which is employed for purification (for example, His-tag) or for detection (for example, Sv5 epitope tag). The fragments include polypeptides generated via proteolytic cleavage (including multi-site proteolysis) of an original sequence. Variants may be post-translationally, or chemically modified. Such variants are deemed to be within the scope of those skilled in the art from the teaching herein.

The polypeptides of the invention can be post-translationally modified. For example, post-translational modifications that fall within the scope of the present invention include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine microsomal membranes or *Xenopus* egg extracts (U.S. Pat. No. 6,103,489) to a standard translation reaction.

The polypeptides of the invention may include unnatural amino acids formed by post-translational modification or by introducing unnatural amino acids during translation. A variety of approaches are available for introducing unnatural amino acids during protein translation. By way of example, special tRNAs, such as tRNAs which have suppressor properties, suppressor tRNAs, have been used in the process of site-directed non-native amino acid replacement (SNAAR). In SNAAR, a unique codon is required on the mRNA and the suppressor tRNA, acting to target a non-native amino acid to a unique site during the protein synthesis (described in WO90/05785). However, the suppressor tRNA must not be recognizable by the aminoacyl tRNA synthetases present in the protein translation system. In some cases, a non-native amino acid can be formed after the tRNA molecule is aminoacylated using chemical reactions which specifically modify the native amino acid and do not significantly alter the functional activity of the aminoacylated tRNA. These reactions are referred to as post-aminoacylation modifications. For example, the epsilon-amino group of the lysine linked to its cognate tRNA (tRNALYS), could be modified with an amine specific photoaffinity label.

A peptide modulator of the invention may be conjugated with other molecules, such as proteins, to prepare fusion proteins. This may be accomplished, for example, by the synthesis of N-terminal or C-terminal fusion proteins provided that the resulting fusion protein retains the functionality of the peptide modulator.

Cyclic derivatives of the peptides or chimeric proteins of the invention are also part of the present invention. Cyclization may allow the peptide or chimeric protein to assume a more favorable conformation for association with other molecules. Cyclization may be achieved using techniques known in the art. For example, disulfide bonds may be formed between two appropriately spaced components having free sulfhydryl groups, or an amide bond may be formed between an amino group of one component and a carboxyl group of another component. Cyclization may also be achieved using an azobenzene-containing amino acid as described by Ulysse, L., et al., J. Am. Chem. Soc. 1995, 117, 8466-8467. The components that form the bonds may be side chains of amino acids, non-amino acid components or a combination of the two. In an embodiment of the invention, cyclic peptides may comprise a beta-turn in the right position. Beta-turns may be introduced into the peptides of the invention by adding the amino acids Pro-Gly at the right position.

In other embodiments, the subject peptide modulator therapeutics are peptidomimetics of the peptide modulators. Peptidomimetics are compounds based on, or derived from, peptides and proteins. The peptidomimetics of the present invention typically can be obtained by structural modification of a known peptide modulator sequence using unnatural amino acids, conformational restraints, isosteric replacement, and the like. The subject peptidomimetics constitute the continuum of structural space between peptides and non-peptide synthetic structures; peptidomimetics may be useful, therefore, in delineating pharmacophores and in helping to translate peptides into nonpeptide compounds with the activity of the parent peptide inhibitors.

Moreover, as is apparent from the present disclosure, mimetopes of the subject peptide inhibitor can be provided. Such peptidomimetics can have such attributes as being non-hydrolyzable (e.g., increased stability against proteases or other physiological conditions which degrade the corresponding peptide), increased specificity and/or potency, and increased cell permeability for intracellular localization of the peptidomimetic.

Peptides of the invention may be developed using a biological expression system. The use of these systems allows the production of large libraries of random peptide sequences and the screening of these libraries for peptide sequences that bind to particular proteins. Libraries may be produced by cloning synthetic DNA that encodes random peptide sequences into appropriate expression vectors. (see Christian et al 1992, J. Mol. Biol. 227:711; Devlin et al, 1990 Science 249:404; Cwirla et al 1990, Proc. Natl. Acad, Sci. USA, 87:6378). Libraries may also be constructed by concurrent synthesis of overlapping peptides (see U.S. Pat. No. 4,708,871).

The peptides and chimeric proteins of the invention may be converted into pharmaceutical salts by reacting with inorganic acids such as hydrochloric acid, sulfuric acid, hydrobromic acid, phosphoric acid, etc., or organic acids such as formic acid, acetic acid, propionic acid, glycolic acid, lactic acid, pyruvic acid, oxalic acid, succinic acid, malic acid, tartaric acid, citric acid, benzoic acid, salicylic acid, benezenesulfonic acid, and toluenesulfonic acids.

Antibodies and peptides may be modified using ordinary molecular biological techniques to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The polypeptides useful in the invention may further be conjugated to non-amino acid moieties that are useful in their application. In particular, moieties that improve the stability, biological half-life, water solubility, and immunologic characteristics of the peptide are useful. A non-limiting example of such a moiety is polyethylene glycol (PEG).

Antibodies

The invention also contemplates a modulator of a miRNA comprising an antibody, or antibody fragment, specific for at least one miRNA associated with a HRD. That is, the antibody can activate or inhibit one or more miRNAs to treat or prevent HRD.

Methods of making and using antibodies are well known in the art. For example, polyclonal antibodies useful in the present invention are generated by immunizing rabbits according to standard immunological techniques well-known in the art (see, e.g., Greenfield et al., 2014, Antibodies, A Laboratory Manual, Cold Spring Harbor, N.Y.). Such techniques include immunizing an animal with a chimeric molecule comprising a portion of another molecule such as a maltose binding protein or glutathione (GSH) tag polypeptide portion, and/or a moiety such that the RNA antigen of interest is rendered immunogenic (e.g., an antigen of interest conjugated with keyhole limpet hemocyanin, KLH) and a portion comprising the respective antigenic protein amino acid residues. The chimeric proteins are produced by cloning the appropriate nucleic acids encoding the marker protein into a plasmid vector suitable for this purpose, such as but not limited to, pMAL-2 or pCMX.

One skilled in the art would appreciate, based upon the disclosure provided herein, that the antibody can specifically bind with any portion of the antigen and the full-length miRNA can be used to generate antibodies specific therefor. However, the present invention is not limited to using the full-length protein as an immunogen. Rather, the present invention includes using an immunogenic portion of the protein to produce an antibody that specifically binds with a specific antigen. That is, the invention includes immunizing an animal using an immunogenic portion, or antigenic determinant, of the antigen.

Once armed with the sequence of a specific antigen of interest and the detailed analysis localizing the various conserved and non-conserved domains of the miRNA, the skilled artisan would understand, based upon the disclosure provided herein, how to obtain antibodies specific for the various portions of the antigen using methods well-known in the art or to be developed.

The skilled artisan would appreciate, based upon the disclosure provided herein, that the present invention includes use of a single antibody recognizing a single antigenic epitope but that the invention is not limited to use of a single antibody. Instead, the invention encompasses use of at least one antibody where the antibodies can be directed to the same or different antigenic protein epitopes.

The generation of polyclonal antibodies is accomplished by inoculating the desired animal with the antigen and isolating antibodies which specifically bind the antigen therefrom using standard antibody production methods.

Monoclonal antibodies directed against full length or peptide fragments of a protein or peptide may be prepared using any well-known monoclonal antibody preparation procedures. Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the miRNA are generated from mice immunized with the miRNA using standard procedures as referenced herein.

Nucleic acid encoding the monoclonal antibody obtained using the procedures described herein may be cloned and sequenced using technology which is available in the art. Further, the antibody of the invention may be "humanized" using methods of humanizing antibodies well-known in the art or to be developed.

The present invention also includes the use of humanized antibodies specifically reactive with epitopes of an antigen of interest. The humanized antibodies of the invention have a human framework and have one or more complementarity determining regions (CDRs) from an antibody, typically a mouse antibody, specifically reactive with an antigen of interest.

The invention also includes functional equivalents of the antibodies described herein. Functional equivalents have binding characteristics comparable to those of the antibodies, and include, for example, hybridized and single chain antibodies, as well as fragments thereof.

Functional equivalents include polypeptides with amino acid sequences substantially the same as the amino acid sequence of the variable or hypervariable regions of the antibodies. "Substantially the same" amino acid sequence is defined herein as a sequence with at least 70%, at least about 80%, at least about 90%, at least about 95%, or at least 99% homology to another amino acid sequence (or any integer in between 70 and 99), as determined by the FASTA search method. Chimeric or other hybrid antibodies have constant regions derived substantially or exclusively from human antibody constant regions and variable regions derived substantially or exclusively from the sequence of the variable region of a monoclonal antibody from each stable hybridoma.

Single chain antibodies (scFv) or Fv fragments are polypeptides that consist of the variable region of the heavy chain of the antibody linked to the variable region of the light chain, with or without an interconnecting linker. Thus, the Fv comprises an antibody combining site.

Functional equivalents of the antibodies of the invention further include fragments of antibodies that have the same, or substantially the same, binding characteristics to those of the whole antibody. Such fragments may contain one or both Fab fragments or the F(ab')2 fragment. The antibody fragments contain all six complement determining regions of the whole antibody, although fragments containing fewer than all of such regions, such as three, four or five complement determining regions, are also functional. The functional equivalents are members of the IgG immunoglobulin class and subclasses thereof, but may be or may combine with any one of the following immunoglobulin classes: IgM, IgA, IgD, or IgE, and subclasses thereof. Heavy chains of various subclasses, such as the IgG subclasses, are responsible for different effector functions and thus, by choosing the desired heavy chain constant region, hybrid antibodies with desired effector function are produced. Exemplary constant regions are gamma 1 (IgG1), gamma 2 (IgG2), gamma 3 (IgG3), and gamma 4 (IgG4). The light chain constant region can be of the kappa or lambda type.

The immunoglobulins of the present invention can be monovalent, divalent or polyvalent. Monovalent immunoglobulins are dimers (HL) formed of a hybrid heavy chain associated through disulfide bridges with a hybrid light chain. Divalent immunoglobulins are tetramers (H2L2) formed of two dimers associated through at least one disulfide bridge.

Small Molecules

Treatment with a miRNA-modulating agent may be carried out using one or more small molecules. When the modulator is a small molecule, a small molecule may be obtained using standard methods known to the skilled artisan. Such methods include chemical organic synthesis or biological means. Biological means include purification from a biological source, recombinant synthesis and in vitro translation systems, using methods well known in the art. In one embodiment, a small molecule modulator of the invention comprises an organic molecule, inorganic molecule, biomolecule, synthetic molecule, and the like.

Combinatorial libraries of molecularly diverse chemical compounds potentially useful in treating a variety of diseases and conditions are well known in the art as are method of making the libraries. The method may use a variety of techniques well-known to the skilled artisan including solid phase synthesis, solution methods, parallel synthesis of single compounds, synthesis of chemical mixtures, rigid core structures, flexible linear sequences, deconvolution strategies, tagging techniques, and generating unbiased molecular landscapes for lead discovery vs. biased structures for lead development.

In a general method for small molecule library synthesis, an activated core molecule is condensed with a number of building blocks, resulting in a combinatorial library of covalently linked, core-building block ensembles. The shape and rigidity of the core determines the orientation of the building blocks in shape space. The libraries can be biased by changing the core, linkage, or building blocks to target a characterized biological structure ("focused libraries") or synthesized with less structural bias using flexible cores.

An exemplary, non-limiting small molecule modulator of HRD-associated miRNAs is celastrol. Exemplary miRNA-modulating small molecules include, but are not limited to resveratrol (Ma, C. et al., 2017, Int J Mol Med., 39(1):231-237), curcumin (Ma, F. et al., 2017, Pharm Biol., 55(1):

1263-1273; Toden, S. et al., 2015, Cancer Prev Res (Phila), 8(5):431-43), methyl dehydrojasmonate ("J2") (Lee, H. J. et al., 2011, M Mol Med (Berl), 89(1):83-90), and nutlin-3a (Kumamoto, K., et al., 2008, Cancer Res., 68(9):3193-203). These molecules modulate one or more miRNAs described herein. For example, resveratrol inhibits miR-155, curcumin inhibits miR-155 and miR-27a, J2 inhibits miR-155 and miR-146, and nutlin-3a upregulates miR-34c. Any of these molecules may be utilized alone or in combination to modulate one or more miRNAs disclosed herein.

The small molecule and small molecule compounds described herein may be present as salts even if salts are not depicted and it is understood that the invention embraces all salts and solvates of the modulators depicted here, as well as the non-salt and non-solvate form of the modulators, as is well understood by the skilled artisan. In some embodiments, the salts of the modulators of the invention are pharmaceutically acceptable salts.

Where tautomeric forms may be present for any of the modulators described herein, each and every tautomeric form is intended to be included in the present invention, even though only one or some of the tautomeric forms may be explicitly depicted. For example, when a 2-hydroxypyridyl moiety is depicted, the corresponding 2-pyridone tautomer is also intended.

The invention also includes any or all of the stereochemical forms, including any enantiomeric or diasteriomeric forms of the modulators described. The recitation of the structure or name herein is intended to embrace all possible stereoisomers of modulators depicted. All forms of the modulators are also embraced by the invention, such as crystalline or non-crystalline forms of the modulators. Compositions comprising a modulator of the invention are also intended, such as a composition of substantially pure modulator, including a specific stereochemical form thereof, or a composition comprising mixtures of modulator of the invention in any ratio, including two or more stereochemical forms, such as in a racemic or non-racemic mixture.

In one embodiment, the small molecule modulator of the invention comprises an analog or derivative of a modulator described herein.

In one embodiment, the small molecules described herein are candidates for derivatization. As such, in some instances, the analogs of the small molecules described herein that have modulated potency, selectivity, and solubility are included herein and provide useful leads for drug discovery and drug development. Thus, in some instances, during optimization new analogs are designed considering issues of drug delivery, metabolism, novelty, and safety.

In some instances, small molecule modulators described herein are derivatized/analoged as is well known in the art of combinatorial and medicinal chemistry. The analogs or derivatives can be prepared by adding and/or substituting functional groups at various locations. As such, the small molecules described herein can be converted into derivatives/analogs using well known chemical synthesis procedures. For example, all of the hydrogen atoms or substituents can be selectively modified to generate new analogs. Also, the linking atoms or groups can be modified into longer or shorter linkers with carbon backbones or hetero atoms. Also, the ring groups can be changed so as to have a different number of atoms in the ring and/or to include hetero atoms. Moreover, aromatics can be converted to cyclic rings, and vice versa. For example, the rings may be from 5-7 atoms, and may be homocycles or heterocycles.

As used herein, the term "analog", "analogue," or "derivative" is meant to refer to a chemical compound or molecule made from a parent compound or molecule by one or more chemical reactions. As such, an analog can be a structure having a structure similar to that of the small molecule modulators described herein or can be based on a scaffold of a small molecule modulator described herein, but differing from it in respect to some components or structural makeup, which may have a similar or opposite action metabolically. An analog or derivative of any of a small molecule modulator in accordance with the present invention can be used to treat a HRD.

In one embodiment, the small molecule modulators described herein can independently be derivatized/analoged by modifying hydrogen groups independently from each other into other substituents. That is, each atom on each molecule can be independently modified with respect to the other atoms on the same molecule. Any traditional modification for producing a derivative/analog can be used. For example, the atoms and substituents can be independently comprised of hydrogen, an alkyl, aliphatic, straight chain aliphatic, aliphatic having a chain hetero atom, branched aliphatic, substituted aliphatic, cyclic aliphatic, heterocyclic aliphatic having one or more hetero atoms, aromatic, heteroaromatic, polyaromatic, polyamino acids, peptides, polypeptides, combinations thereof, halogens, halo-substituted aliphatics, and the like. Additionally, any ring group on a compound can be derivatized to increase and/or decrease ring size as well as change the backbone atoms to carbon atoms or hetero atoms.

Once a patient is diagnosed with having or is at risk of having a HRD, the patient can be treated using methods known in the art. Well known treatments for HRDs include, but are not limited to, drug treatments, and surgical treatments. Drug treatments used for the treatment of HRDs, such as atherosclerosis, NAFLD, T2DM/IR, obesity, type I MHO, and type II MHO include angiotensin-converting enzyme (ACE) inhibitors, statins, fibrates, beta-blockers, calcium channel blockers, angiotensin II receptor blockers, anti-platelet medications, anti-coagulant medications, aspirin, rosuvastatin calcium, rosuvastatin, weight reducing drugs, insulin sensitizers, lipid-lowering agents, antioxidants, bile salts, co-factors increasing the mitochondrial transport of fatty acids, thiazolidinediones, orlistat, and others well known in the art. Surgical treatments include, but are not limited to, gastric bypass surgery, bariatric surgery, coronary artery bypass surgery, carotid artery surgery, atherosclerosis plaque removal surgery, and atherectomy. Other treatments particularly well suited for use in the present invention are well known in the art. In one embodiment, the patient can be treated using dietary modification, lifestyle modification, physical therapy, or other means known in the art to treat or prevent progression of HRD.

Modulators of miRNA

In certain embodiments, the composition comprises a modulator of one or more disease-associated miRNAs described herein. For example, in certain embodiments, the composition comprises an agent that increases the expression or activity of a disease-associated miRNA that is downregulated in the disease state. In one embodiment, the composition comprises an agent that mimics the activity of a disease-associated miRNA. In one embodiment, the agent comprises a disease-associated miRNA or a mimic of a disease-associated miRNA. In one embodiment, the agent comprises a nucleic acid molecule that encodes a disease-associated miRNA or mimic of a disease-associated miRNA.

In one embodiment, one or more of the disease associated miRNA or mimic thereof, may be administered to a subject at risk of developing or having been diagnosed with a HRD or disorder. In an exemplary embodiment, the miRNAs administered to the subject are downregulated in the disease state. In another exemplary embodiment, the miRNAs are coupled to a moiety that increases cell penetration or solubility of the miRNA. In one embodiment, the miRNA is coupled to cholesterol. In another embodiment, the miRNA is coupled to one or more moieties or combined with one or more compositions that are capable of directing the miRNA to a specific organ, tissue, or cell type. In one embodiment, the composition comprising an miRNA is administered locally. In another embodiment, the composition comprising an miRNA is administered systemically. In various embodiments, the miRNA reduces the level, expression, or activity of one or more mRNAs that are associated with a HRD or disorder.

MiRNAs are small non-coding RNA molecules that are capable of causing post-transcriptional silencing of specific genes in cells by the inhibition of translation or through degradation of the targeted mRNA. A miRNA can be completely complementary or can have a region of noncomplementarity with a target nucleic acid, consequently resulting in a "bulge" at the region of non-complementarity. A miRNA can inhibit gene expression by repressing translation, such as when the miRNA is not completely complementary to the target nucleic acid, or by causing target RNA degradation, which is believed to occur only when the miRNA binds its target with perfect complementarity. The disclosure also can include double-stranded precursors of miRNA. A miRNA or pri-miRNA can be 18-100 nucleotides in length, or from 18-80 nucleotides in length. Mature miRNAs can have a length of 19-30 nucleotides, or 21-25 nucleotides, particularly 21, 22, 23, 24, or 25 nucleotides. MiRNA precursors typically have a length of about 70-100 nucleotides and have a hairpin conformation. miRNAs are generated in vivo from pre-miRNAs by the enzymes Dicer and Drosha, which specifically process long pre-miRNA into functional miRNA. The hairpin or mature microRNAs, or pri-microRNA agents featured in the disclosure can be synthesized in vivo by a cell-based system or in vitro by chemical synthesis.

In various embodiments, the agent comprises an oligonucleotide that comprises the nucleotide sequence of a disease-associated miRNA. In certain embodiments, the oligonucleotide comprises the nucleotide sequence of a disease-associated miRNA in a pre-microRNA, mature or hairpin form. In other embodiments, a combination of oligonucleotides comprising a sequence of one or more disease-associated miRNAs, any pre-miRNA, any fragment, or any combination thereof is envisioned.

MiRNAs can be synthesized to include a modification that imparts a desired characteristic. For example, the modification can improve stability, hybridization thermodynamics with a target nucleic acid, targeting to a particular tissue or cell-type, or cell permeability, e.g., by an endocytosis-dependent or -independent mechanism.

Modifications can also increase sequence specificity, and consequently decrease off-site targeting. Methods of synthesis and chemical modifications are described in greater detail below. If desired, miRNA molecules may be modified to stabilize the miRNAs against degradation, to enhance half-life, or to otherwise improve efficacy. Desirable modifications are described, for example, in U.S. Patent Publication Nos. 20070213292, 20060287260, 20060035254. 20060008822. and 2005028824, each of which is hereby incorporated by reference in its entirety. For increased nuclease resistance and/or binding affinity to the target, the single-stranded oligonucleotide agents featured in the disclosure can include 2'-O-methyl, 2'-fluorine, 2'-O-methoxyethyl, 2'-O-aminopropyl, 2'-amino, and/or phosphorothioate linkages. Inclusion of locked nucleic acids (LNA), ethylene nucleic acids (ENA), e.g., 2'-4'-ethylene-bridged nucleic acids, and certain nucleotide modifications can also increase binding affinity to the target. The inclusion of pyranose sugars in the oligonucleotide backbone can also decrease endonucleolytic cleavage. An oligonucleotide can be further modified by including a 3' cationic group, or by inverting the nucleoside at the 3'-terminus with a 3-3' linkage. In another alternative, the 3 '-terminus can be blocked with an aminoalkyl group. Other 3' conjugates can inhibit 3'-5' exonucleolytic cleavage. While not being bound by theory, a 3' may inhibit exonucleolytic cleavage by sterically blocking the exonuclease from binding to the 3' end of the oligonucleotide. Even small alkyl chains, aryl groups, or heterocyclic conjugates or modified sugars (D-ribose, deoxyribose, glucose etc.) can block 3'-5'-exonucleases.

In one embodiment, the miRNA includes a 2'-modified oligonucleotide containing oligodeoxynucleotide gaps with some or all internucleotide linkages modified to phosphorothioates for nuclease resistance. The presence of methylphosphonate modifications increases the affinity of the oligonucleotide for its target RNA and thus reduces the $IC_5Q$. This modification also increases the nuclease resistance of the modified oligonucleotide. It is understood that the methods and reagents of the present disclosure may be used in conjunction with any technologies that may be developed to enhance the stability or efficacy of an inhibitory nucleic acid molecule.

miRNA molecules include nucleotide oligomers containing modified backbones or non-natural internucleoside linkages. Oligomers having modified backbones include those that retain a phosphorus atom in the backbone and those that do not have a phosphorus atom in the backbone. For the purposes of this disclosure, modified oligonucleotides that do not have a phosphorus atom in their internucleoside backbone are also considered to be nucleotide oligomers. Nucleotide oligomers that have modified oligonucleotide backbones include, for example, phosphorothioates, chiral phosphorothioates, phosphorodithioates, phosphotriesters, aminoalkyl-phosphotriesters, methyl and other alkyl phosphonates including 3'-alkylene phosphonates and chiral phosphonates, phosphinates, phosphoramidates, thionophosphoramidates, thionoalkylphosphonates, thionoalkylphosphotriest-ers, and boranophosphates. Various salts, mixed salts and free acid forms are also included. Representative United States patents that teach the preparation of the above phosphorus-containing linkages include, but are not limited to, U.S. Pat. Nos. 3,687,808; 4,469,863; 4,476, 301; 5,023,243; 5,177,196; 5,188,897; 5,264,423; 5,276, 019; 5,278,302; 5,286,717; 5,321,131; 5,399,676; 5,405, 939; 5,453,496; 5,455,233; 5,466,677; 5,476,925; 5,519, 126; 5,536,821; 5,541,306; 5,550,111; 5,563,253; 5,571, 799; 5,587,361; and 5,625,050, each of which is herein incorporated by reference.

Nucleotide oligomers having modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyl eneimino and methylenehydrazino backbones; sulfonate and sulfonamide backbones; amide backbones; and others having mixed N, O, S and CH2 component parts. Representative United States patents that teach the preparation of the above oligonucleotides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference. Nucleotide oligomers may also contain one or more substituted sugar moieties. Such modifications include 2'-O-methyl and 2'-methoxyethoxy modifications. Another desirable modification is 2'-dimethylaminooxyethoxy, 2'-aminopropoxy and 2'-fluoro. Similar modifications may also be made at other positions on an oligonucleotide or other nucleotide oligomer, particularly the 3' position of the sugar on the 3' terminal nucleotide. Nucleotide oligomers may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

In other nucleotide oligomers, both the sugar and the internucleoside linkage, i.e., the backbone, are replaced with groups. Methods for making and using these nucleotide oligomers are described, for example, in "Peptide Nucleic Acids (PNA): Protocols and Applications" Ed. P. E. Nielsen, Horizon Press, Norfolk, United Kingdom, 1999. Representative United States patents that teach the preparation of PNAs include, but are not limited to, U.S. Pat. Nos. 5,539,082; 5,714,331; and 5,719,262, each of which is herein incorporated by reference. Further teaching of PNA compounds can be found in Nielsen et al, Science, 1991, 254, 1497-1500.

In other embodiments, a single stranded modified nucleic acid molecule (e.g., a nucleic acid molecule comprising a phosphorothioate backbone and 2'-OMe sugar modifications is conjugated to cholesterol.

A miRNA described herein, which may be in the mature or hairpin form, may be provided as a naked oligonucleotide that is capable of entering a tumor cell. In some cases, it may be desirable to utilize a formulation that aids in the delivery of a miRNA or other nucleotide oligomer to cells (see, e.g., U.S. Pat. Nos. 5,656,611, 5,753,613, 5,785,992, 6,120,798, 6,221,959, 6,346,613, and 6,353,055, each of which is hereby incorporated by reference).

In some examples, the miRNA composition is at least partially crystalline, uniformly crystalline, and/or anhydrous (e.g., less than 80, 50, 30, 20, or 10% water). In another example, the miRNA composition is in an aqueous phase, e.g., in a solution that includes water. The aqueous phase or the crystalline compositions can be incorporated into a delivery vehicle, e.g., a liposome (particularly for the aqueous phase), or a particle (e.g., a microparticle as can be appropriate for a crystalline composition). Generally, the miRNA composition is formulated in a manner that is compatible with the intended method of administration. A miRNA composition can be formulated in combination with another agent, e.g., another therapeutic agent or an agent that stabilizes an oligonucleotide agent, e.g., a protein that complexes with the oligonucleotide agent. Still other agents include chelators, e.g., EDTA (e.g., to remove divalent cations such as Mg), salts, and RNAse inhibitors (e.g., a broad specificity RNAse inhibitor). In one embodiment, the miRNA composition includes another miRNA, e.g., a second miRNA composition (e.g., a microRNA that is distinct from the first). Still other preparations can include at least three, five, ten, twenty, fifty, or a hundred or more different oligonucleotide species.

In certain embodiments, the composition comprises an oligonucleotide composition that mimics the activity of a disease-associated miRNA, described herein. In certain embodiments, the composition comprises oligonucleotides having nucleobase identity to the nucleobase sequence of a disease-associated miRNA, and are thus designed to mimic the activity of the disease-associated miRNA. In certain embodiments, the oligonucleotide composition that mimics miRNA activity comprises a double-stranded RNA molecule which mimics the mature miRNA hairpins or processed miRNA duplexes.

In one embodiment, the oligonucleotide shares identity with endogenous miRNA or miRNA precursor nucleobase sequences. An oligonucleotide selected for inclusion in a composition of the present invention may be one of a number of lengths. Such an oligonucleotide can be from 7 to 100 linked nucleosides in length. For example, an oligonucleotide sharing nucleobase identity with a miRNA may be from 7 to 30 linked nucleosides in length. An oligonucleotide sharing identity with a miRNA precursor may be up to 100 linked nucleosides in length. In certain embodiments, an oligonucleotide comprises 7 to 30 linked nucleosides. In certain embodiments, an oligonucleotide comprises 7, 8, 9, 10, 11, 12, 13, 14, 15, 16, 17, 18, 19, 20, 21, 22, 23, 24, 25, 26, 28, 29, or 30 linked nucleotides. In certain embodiments, an oligonucleotide comprises 19 to 23 linked nucleosides. In certain embodiments, an oligonucleotide is from 40 up to 50, 60, 70, 80, 90, or 100 linked nucleosides in length.

In certain embodiments, an oligonucleotide has a sequence that has a certain identity to a miRNA or a precursor thereof. Nucleobase sequences of mature miRNAs and their corresponding stem-loop sequences described herein are the sequences found in miRBase, an online searchable database of miRNA sequences and annotation. Entries in the miRBase Sequence database represent a predicted hairpin portion of a miRNA transcript (the stem-loop), with information on the location and sequence of the mature miRNA sequence. The miRNA stem-loop sequences in the database are not strictly precursor miRNAs (pre-miRNAs), and may in some instances include the pre-miRNA and some flanking sequence from the presumed primary transcript. The miRNA nucleobase sequences described herein encompass any version of the miRNA, including the sequences described in Release 10.0 of the miRBase sequence database and sequences described in any earlier Release of the miRBase sequence database. A sequence database release may result in the re-naming of certain miRNAs. A sequence database release may result in a variation of a mature miRNA sequence. The compositions of the present invention encompass oligomeric compound comprising oligonucleotides having a certain identity to any nucleobase sequence version of a miRNAs described herein.

In certain embodiments, an oligonucleotide has a nucleobase sequence at least 60%, 65%, 70%, 75%, 80%, 85%, 90%, 95%, 97%, 98% or 99% identical to the miRNA over a region of 7, 8, 9, 10, 11, 12, 13, 14, 15, 16, 17, 18, 19, 20, 21, 22, 23, 24, 25, 26, 27, 28, 29, or 30 nucleobases. Accordingly, in certain embodiments the nucleobase sequence of an oligonucleotide may have one or more non-identical nucleobases with respect to the miRNA.

In certain embodiments, the composition comprises a nucleic acid molecule encoding a miRNA, precursor, mimic, or fragment thereof. For example, the composition may comprise a viral vector, plasmid, cosmid, or other expression vector suitable for expressing the miRNA, precursor, mimic, or fragment thereof in a desired mammalian cell or tissue.

Combinations

In one embodiment, the composition of the present invention comprises a combination of modulators described herein. For example, in one embodiment the composition comprises an inhibitor of one or more miRNAs disclosed herein, in combination with an agent that increases or mimics the activity of one or more miRNAs disclosed herein. In some embodiments, a composition comprising a combination of modulators described herein has an additive effect, wherein the overall effect of the combination is approximately equal to the sum of the effects of each individual inhibitor. In other embodiments, a composition comprising a combination of modulators described herein has a synergistic effect, wherein the overall effect of the combination is greater than the sum of the effects of each individual modulator.

A composition comprising a combination of modulators comprise individual modulators in any suitable ratio. For example, in one embodiment, the composition comprises a 1:1 ratio of two individual modulators. In another embodiment, the composition comprises a 1:1:1 ratio of three individual modulators. However, the combination is not limited to any particular ratio. Rather any ratio that is shown to be effective is encompassed.

Pharmaceutical Compositions

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions that are useful in the methods of the invention may be prepared, packaged, or sold in formulations suitable for ophthalmic, oral, rectal, vaginal, parenteral, topical, pulmonary, intranasal, buccal, intratumoral, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents, including, for example, chemotherapeutics, immunosuppressants, corticosteroids, analgesics, and the like.

Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intraocular, intravitreal, subcutaneous, intraperitoneal, intramuscular, intrasternal injection, intratumoral, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally acceptable diluent or solvent, such as water or 1,3 butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, for example, from about 1 to about 6 nanometers. Such compositions are conveniently in the form of dry powders for administration using a device comprising a dry powder reservoir to which a stream of propellant may be directed to disperse the powder or using a self-propelling solvent/powder dispensing container such as a device comprising the active ingredient dissolved or suspended in a low-boiling propellant in a sealed container. For example, such powders comprise particles wherein at least 98% of the particles by weight have a diameter greater than 0.5 nanometers and at least 95% of the particles by number have a diameter less than 7 nanometers. For example, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (e.g., having a particle size of the same order as particles comprising the active ingredient).

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally acceptable diluent or solvent, such as water or 1,3 butane diol, for example. Other acceptable diluents and solvents include, but are not limited to, Ringer's solution, isotonic sodium chloride solution, and fixed oils such as synthetic mono- or di-glycerides. Other parentally-administrable formulations that are useful include those that comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Additionally, the molecules may be delivered using a sustained-release system, such as semipermeable matrices of solid polymers containing the therapeutic agent. Various forms of sustained-release materials have been established and are well known by those skilled in the art. Sustained-release capsules may, depending on their chemical nature, release the molecules for a few weeks up to over 100 days. Depending on the chemical nature and the biological stability of the chimeric molecules, additional strategies for molecule stabilization may be employed.

Nucleic acids may be included in any of the above-described formulations as the free acids or bases or as pharmaceutically acceptable salts. Pharmaceutically acceptable salts are those salts that substantially retain the biologic activity of the free bases and which are prepared by reaction with inorganic acids. Pharmaceutical salts tend to be more soluble in aqueous and other protic solvents than are the corresponding free base forms.

In addition to the formulations described previously, the molecules may also be formulated as a depot preparation. Such long acting formulations may be administered by implantation (for example subcutaneously or intramuscularly) or by intramuscular injection. Thus, for example, the molecules may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well-known examples of delivery vehicles that may be used to deliver nucleic acids of the disclosure.

Administration

One aspect of the invention relates to a treatment regimen for treating or preventing a HRD or disorder using a composition of the invention. Compositions of the invention may be delivered alone or in combination with other compositions of the invention, and may be administered locally or systemically using appropriate methods known in the art. Administration of the compositions of the present invention to a subject may be carried out using known procedures, at dosages and for periods of time effective to prevent or treat a HRD or disorder in the subject. An effective amount of the therapeutic compound necessary to achieve a therapeutic effect may vary according to factors such as the state of the disease or disorder in the subject; the age, sex, and weight of the subject.

The regimen of administration may affect what constitutes an effective amount. Further, the dosages of the compositions may be proportionally increased or decreased as indicated by the exigencies of the therapeutic or prophylactic situation. A non-limiting example of an effective dose range for a therapeutic compound of the invention is from about 1 to about 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular subject, composition, and mode of administration, without being toxic to the subject.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the subject being treated, and like factors well known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 50 mg to about 1,000 mg, about 75 mg to about 900 mg, about 100 mg to about 800 mg, about 250 mg to about 750 mg, about 300 mg to about 600 mg, about 400 mg to about 500 mg, and any and all whole or partial increments thereabetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments there between.

In one embodiment, the treatment regimen comprises daily administration of a composition of the invention. In one embodiment, a treatment regimen comprises administering a composition at least once daily for at least 1 day, at least 2 days, at least 3 days, at least 4 days, at least 5 days, at least 7 days, at least 10 days, at least 2 weeks, at least 3 weeks, at least 1 month, at least 2 months, at least 3 months, at least 6 months, at least 1 year or more than 1 year. In one embodiment, a treatment regimen comprises administering a composition two times daily for at least 1 day, at least 2 days, at least 3 days, at least 4 days, at least 5 days, at least 7 days, at least 10 days, at least 2 weeks, at least 3 weeks, at least 1 month, at least 2 months, at least 3 months, at least 6 months, at least 1 year or more than 1 year. In one embodiment, a treatment regimen comprises administering a composition three times daily for at least 1 day, at least 2 days, at least 3 days, at least 4 days, at least 5 days, at least 7 days, at least 10 days, at least 2 weeks, at least 3 weeks, at least 1 month, at least 2 months, at least 3 months, at least 6 months, at least 1 year or more than 1 year.

Kits

The present invention also pertains to kits useful in the methods of the invention. Such kits comprise components useful in any of the methods described herein, including for example, hybridization probes or primers (e.g., labeled probes or primers), reagents for detection of labeled molecules, oligonucleotide arrays, restriction enzymes, antibodies, allele-specific oligonucleotides, means for amplification of a subject's nucleic acids, means for reverse transcribing a subject's RNA, means for analyzing a subject's nucleic acid sequence, and instructional materials. For example, in one embodiment, the kit comprises components useful for the detection and quantification of at least one miRNA associated with a HRD. In an exemplary embodiment of the invention, the kit comprises components for detecting one or more of the miRNAs associated with atherosclerosis, NAFLD, T2DM/IR, obesity, type I MHO, type II MHO, or a combination thereof as elsewhere described herein.

The present invention also provides kits for diagnosing a HRD, comprising a probe for one or more nucleic acid biomarkers known to be differentially expressed in a HRD. In one particular embodiment, the kit comprises reagents for quantitative amplification of the selected biomarkers. Alternatively, the kit may comprise a microarray. In some embodiments the kit comprises 2 or more probes. In other embodiments, the kits may contain 3, 4, 5, 6, 7, 8, 9, 10, 15, 20, 25, 30, 35, 40, 45, 50, 55, 60, 65, 70, 75, 80, 85, 90, 95, 100 or more probes.

The present invention also pertains to kits useful in the methods of the invention. Such kits comprise various combinations of components useful in any of the methods described elsewhere herein, including for example, materials for quantitatively analyzing a biomarker of the invention (e.g., polypeptide and/or nucleic acid), materials for assessing the activity of a biomarker of the invention (e.g., polypeptide and/or nucleic acid), and instructional material. For example, in one embodiment, the kit comprises components useful for the quantification of a desired nucleic acid in a biological sample.

In a further embodiment, the kit comprises the components of an assay for monitoring the effectiveness of a treatment administered to a subject in need thereof, containing instructional material and the components for determining whether the level of a biomarker of the invention in a biological sample obtained from the subject is modulated during or after administration of the treatment. In various embodiments, to determine whether the level of a biomarker of the invention is modulated in a biological sample obtained from the subject, the level of the biomarker is compared with the level of at least one comparator control contained in the kit, such as a positive control, a negative control, a historical control, a historical norm, or the level of another reference molecule in the biological sample. In some embodiments, the ratio of the biomarker and a reference molecule is determined to aid in the monitoring of the treatment.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: MicroRNA-221 and MicroRNA-155 Potentially Serve as Master Regulators in Newly Classified Type I and Type II Metabolically Healthy Obese Since their discovery in 1993, miRNAs have proven to be important regulators of gene expression under both physiological and pathological conditions (Virtue, A. et al., 2012, Journal of Hematology & Oncology, 5:66; Virtue, A. et al., 2011, Front Biosci, 16:3133-3145), including atherosclerosis, obesity, T2DM/IR and NAFLD. Furthermore, over the years, it has become clear that hyperlipidemia undergirds the formation of and/or results from these four diseases. In addition, these diseases can mutually promote their development. For instance, obesity serves as a risk factor for the development of atherosclerosis, insulin resistance and increases deposition of fat in the liver, giving rise to NAFLD (Pi-Sunyer, X. et al., 2009, Postgraduate Medicine, 121(6): 21-33; Gaggini, M. et al., 2013, Nutrients, 5(5):1544-1560). Insulin resistance is a well-noted risk factor for type II diabetes; and the latter is a risk factor for atherosclerosis (Chait, A. et al., 2009, Journal of Lipid Research, 50: S335-S339). With the increasing prevalence of these disease conditions, understanding their molecular underpinnings remains imperative.

In this datamining study, firstly, it is identified that significantly modulated miRNAs are largely specific to single diseases while only a few miRNAs are shared among disease clusters. While numerous miRNAs are expressed within and among various diseases, only miR-155 and miR-221 are significantly modulated in all four diseases; secondly, it is found that only a few significantly modulated experimentally verified transcription factors (TFs) regulate the miRNAs in shared diseases. Furthermore, the TFs regulating miRNAs in all four diseases include EGR1, NFκB, and STAT3; thirdly, potential biomarkers for single and co-morbid diseases have been identified, that may be used in predicting the patients at risk for developing one or more of these four diseases; fourthly, the downstream miRNA targets that have been experimentally verified to promote or inhibit one or more of these diseases have been compiled. These findings demonstrate that miRNAs, such as miR-155, are able to carry out their potent and differential functions due to presence and abundance of various mRNA targets expressed in various tissues. Of interest, is the finding that SOCS1 is commonly targeted in all four diseases; fifthly, using IPA, it is found that these diseases had active pathways in six categories: arthritis, cancer, development, immunology, metabolism, and proliferation/survival. It is also found that various hyperlipidemia-related diseases share pathways with cancer and MHO, suggesting the possibility that these conditions are interrelated. Such a finding may imply that depending on the disease or comorbid diseases a patient has, he or she can be placed at risk for developing separate conditions related to the affected relevant pathway(s).

Figure 8A:
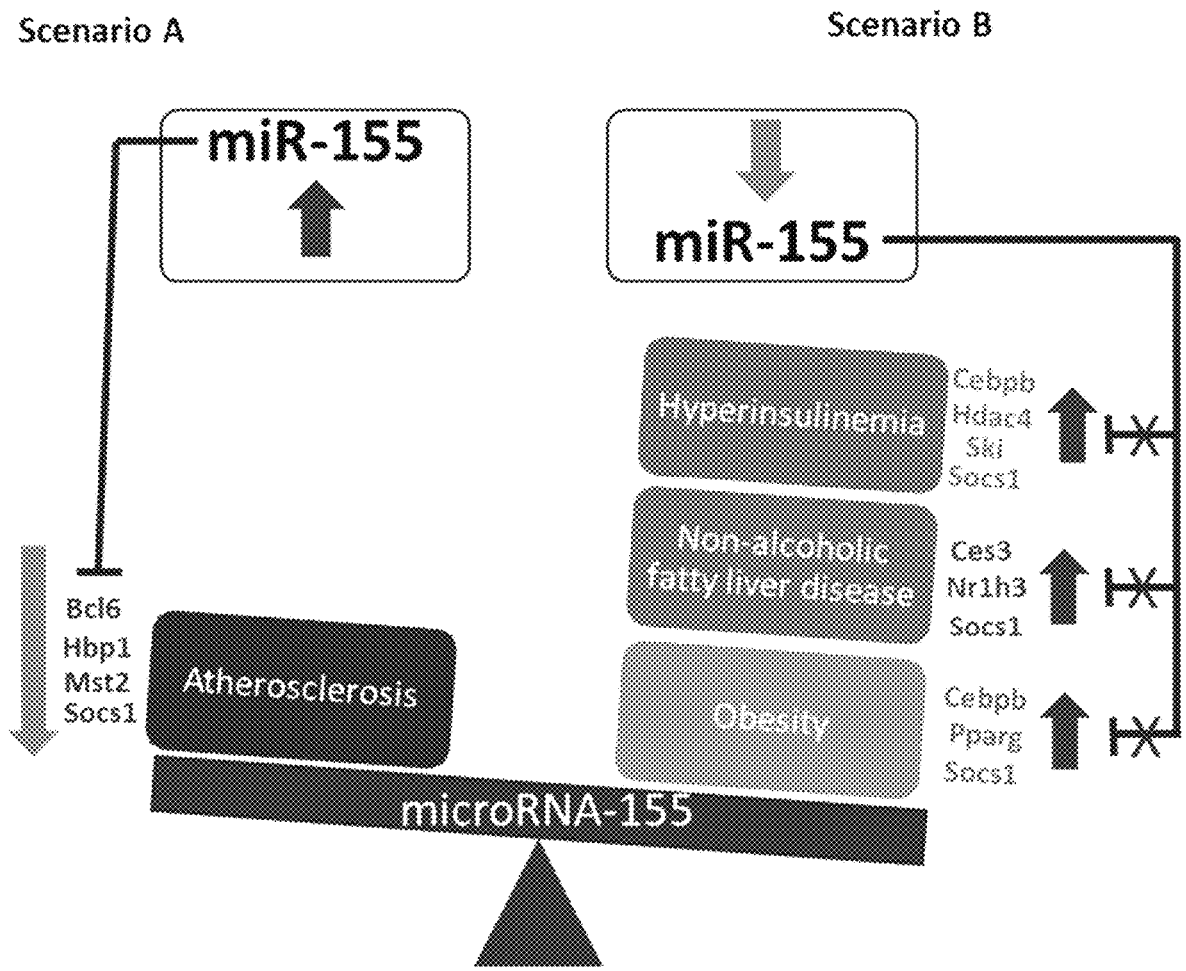

EGR1 (early growth response 1) is a transcription factor that in normal conditions has low or no expression but is associated with inflammation due to injury where it can promote wound healing or pathological fibrosis. Furthermore, this TF plays a role in cancer and schizophrenia development and is a member of the immediate and fast transcription group of genes known as immediate early genes (IEGs). Prior studies show increased expression of EGR1 is associated with atherosclerosis (Bhattacharyya, S. et al., 2012, The Journal of Pathology, 3(2):286-297) while EGR1 knockout mice exhibited resistance to obesity, insulin resistance and fatty liver (Zhang, J. et al., 2013, Scientific Reports, 3:1476). STAT3 (Signal transducers and activators of transcription 3) plays a role in apoptosis, cellular proliferation, angiogenesis, cancer development, and inflammation (Mali, S. B. et al., 2015, Oral Oncology, 51(6):565-569). Phosphorylation of STATs is needed for their dimerization and subsequent transcription factor activity (Villarino, A. V. et al., 2015, The Journal of Immunology, 194(1):21-27). In atherosclerosis, STAT3 is activated in response to oxidized LDL, an initiator molecule of atherosclerosis (Mazjere C. et al., 1999, FEBS letters, 448(1):49-52). Interestingly, SOCS1 (suppressor of cytokine signaling 1) is a negative regulator of STAT3 (Wang R. et al., 2016, Scientific Report, 6:36790). Moreover, T cell-mediated STAT3 promoted insulin resistance and obesity (Priceman, S. J. et al., 2013, Proc Natl Acad Sci USA, 110(32):13079-13084) while leptin (satiety hormone) signaling relied on downstream STAT3 signaling (Buettner, C. et al., 2006, Cell metabolism, 4(1):49-60). Furthermore, STAT3 is active in NAFLD (Min H. et al., 2015, American Journal of Physiology-Gastrointestinal and Liver Physiology, 308(9): G794-G803). NFκB is a pleiotropic TF regulating cell death, proliferation, the immune response, and playing a role in a host of diseases (Hayden, M. S. et al., 2012, Genes and Development, 26(3):203-34), including promoting atherosclerosis (Pamukcu, B. et al., 2011, Thrombosis Research, 128(2):117-123), being associated with obesity, T2DM (Baker, R. G. et al., 2011, Cell Metabolism, 13(1): 11-22) and, as some evidence suggests, being associated with NAFLD (Zeng, L. et al., 2014, International Journal of Clinical and Experimental Medicine, 7(7):1624-1631). Previous studies show that SOCS1 is suppressed in atherosclerosis (Yang, Y. et al., 2015, Cellular Physiology and Biochemistry, 36(4):1371-1381) but promotes insulin resistance (Ueki, K. et al., 2004, Molecular and Cellular Biology, 24(12):5434-5446). Furthermore, SOCS1 is an NFκB negative regulator (Fujimoto, M. et al., 2010, Gastroenterology Research and Practice, 2010). Taken together, these findings demonstrate that STAT3 and NFκB may be critical mediators of the hyperlipidemia-related pathologies of atherosclerosis, NAFLD, obesity and type II diabetes/insulin resistance via miR-155, which being upregulated/present in mice having an atherosclerosis background, worsens atherosclerosis but does not significantly affect the heath of the liver, adipose tissue, or blood insulin/glucose levels. However, regarding patients having metabolically healthy obesity (i.e., obese with healthy cardiovascular condition), it is proposed that in such a situation, STAT3 and/or NFκB is reduced, leading to reduction of miR-155. This produces a phenotype of obesity, NAFLD, hyperglycemia without insulin resistance but reduced atherosclerosis. The compiled data herein demonstrates that this paradoxical phenotype is achieved due to presence of different targets being expressed in the different cell types as well as differing levels of these targets (FIG. 8). More specifically, mRNA targets such as Bcl6, Hbp1, Mst2, and Socs1, which are reduced in atherosclerosis have been shown to play a protective role against the disease's development. Cebpb, Hdac4, Ski, Socs1 mRNAs, which are reduced in diabetes and/or insulin resistance, have also demonstrated protective roles in these conditions. On the other hand, reducing Ces3, Nr1h3, Socs1 levels in NAFLD has been shown to be protective. Similarly, decreased levels of Cebpb, Pparg, and Socs1 mitigated diet-induced obesity (FIG. 4A).

Figure 8C:
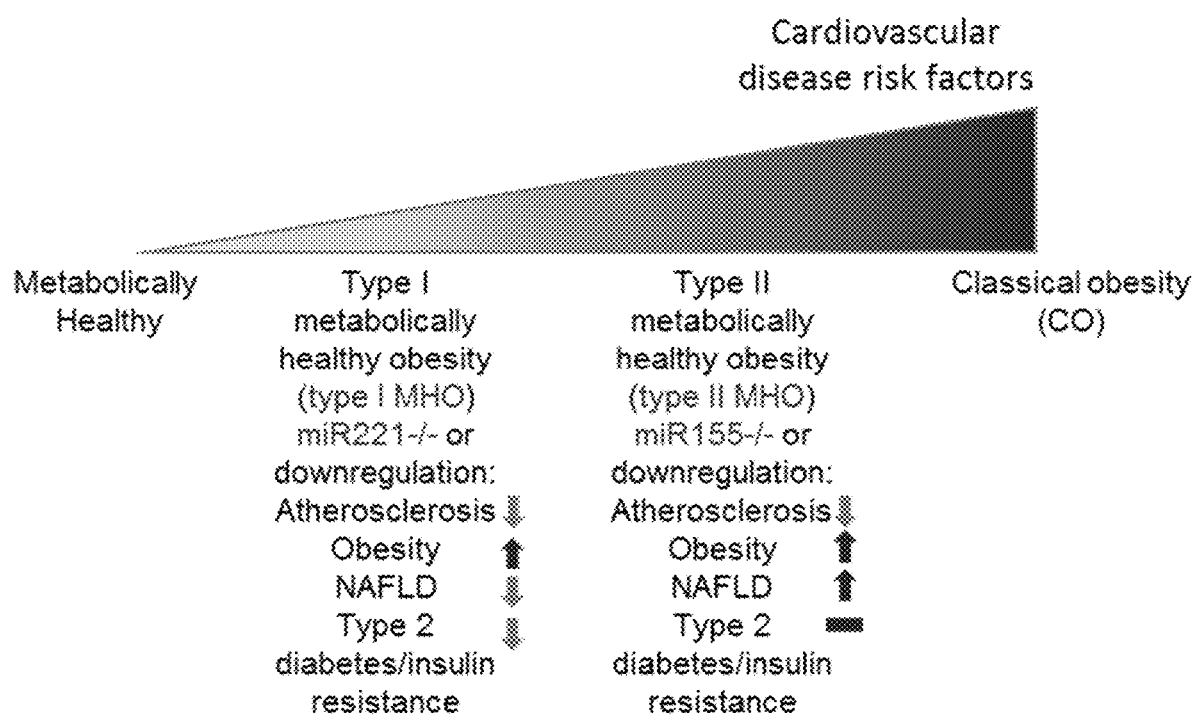

MHO is not a static condition but a temporary transient state that eventually results in classically unhealthy obesity (FIG. 8C) (Hinnouho, G. et al., 2013, Diabetes Care, 6(8): 2294-2300; Jung, C. H. et al., 2017, Jorean J Intern Med, 32(4):611-621). Previously, it was found that miR-155 deficiency led to reduced atherosclerosis (and therefore cardiovascular risk factors) but increased obesity, NAFLD, and hyperglycemia without insulin resistance. Based on these current findings, miR-221 deficiency was identified as another MHO model as FIG. 2B shows (reduced atherosclerosis, NAFLD, and T2DM but increased obesity), suggesting that global deficiency of miR-221 may lead to obesity without any of the other inflammatory and hyperlipidemic diseases. Indeed, numerous studies lend support to the pro-atherogenic role of elevated miR-221 (Coskunpinar, G. et al., 2016, Gene, 591(1):90-96, Mandraffino, G. et al., 2017, PLOS One, 12(3):e0173030, Talepoor, A. G. et al., 2017, International Journal of Toxicity, 36(2):133-141, Zhang, X. et al., 2014, The Journal of Clinical Endocrinology & Metabolism, 99(5):E766-E774, Kothapalli, D. et al., 2013, Atherosclerosis, 227(1):65-71). Moreover, deficiency of miR-155 or miR-221 leads to two varied manifestations of MHO, based on which a new concept of MHO heterogeneity and classification of MHO is proposed; and have a label as Type 1 MHO (miR221$^{-/-}$) or Type 2 MHO (miR155$^{-/+}$) (FIG. 8C). In alignment with studies showing MHO as a temporary state of obesity, data presented in this work suggests that miR-221 is first to be downregulated to create type I MHO. This is then followed by miR-155 downregulation, leading to type II MHO. Finally, MHO makes the transition to classical obesity.

Figure 9:
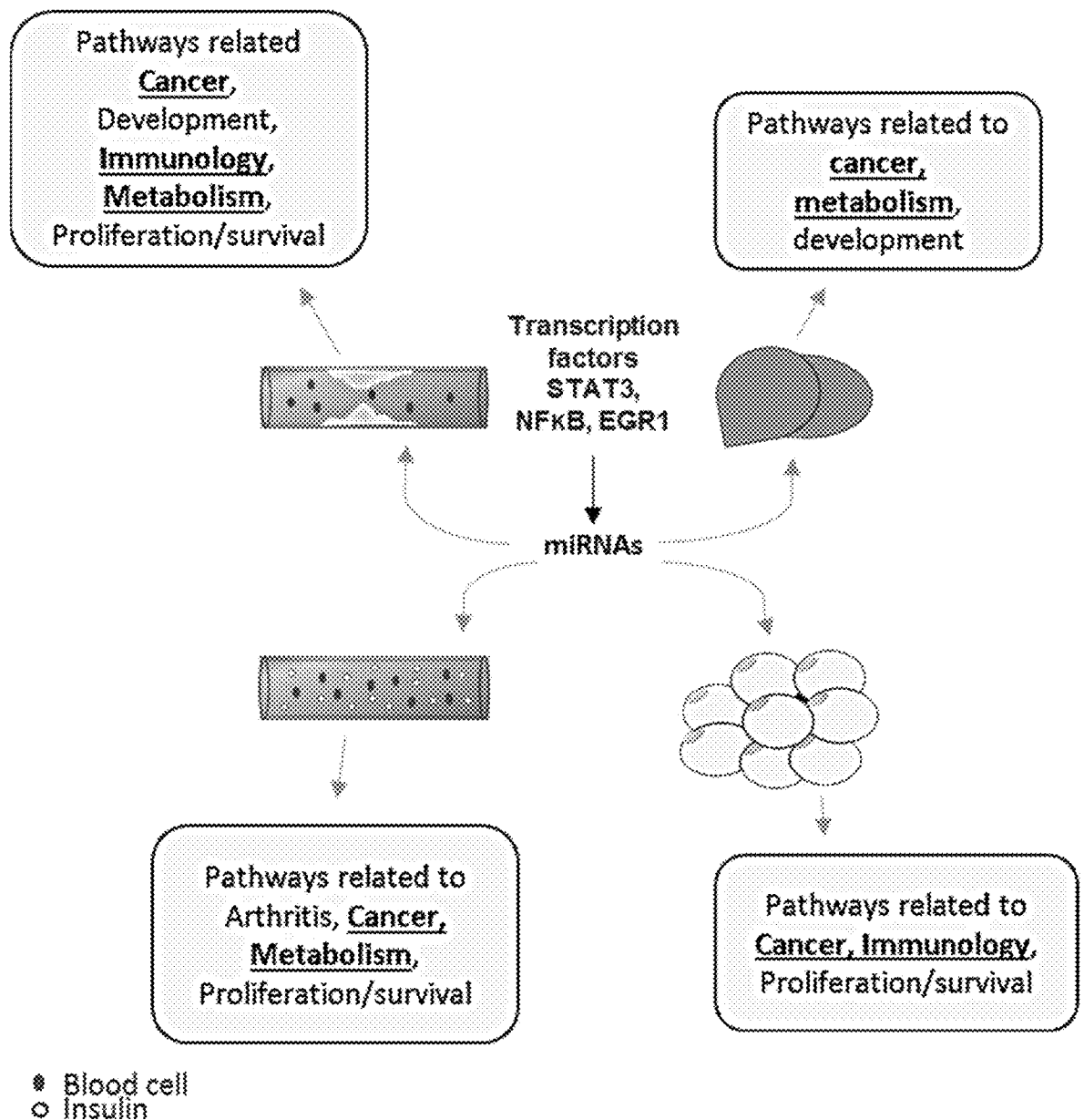
FIG. 9 depicts a schematic diagram demonstrating that transcription factors, such as STAT3, NFKB and EGR1, can promote the transcription levels of various miRNAs that are both shared between and unique to hyperlipidemia diseases. Over time, these miRNAs may play a role to promote pathways related to cancer, arthritis, proliferation/survival and more, which leads to additional diseases.

In summary, a new working model is proposed, showing that transcription factors, such as STAT3, NFκB and EGR1, increases transcript levels of various miRNAs that are unique to the four HRDs (atherosclerosis, NAFLD, obesity and T2DM/IR) as well as shared among the HRDs. These miRNAs, expressed in various tissues inhibit translation of or degrade mRNA targets that not only help give rise to HRD phenotype but may also be an underlying mechanism of cancer, arthritis and other conditions involving proliferation/survival, development, immunology, and metabolism pathways (FIG. 9).

The materials and methods employed in these experiments are now described.

MiRNAs, miRNA-Regulating Transcription Factors, miRNA-Targeted mRNAs Studied

Figure 1D:
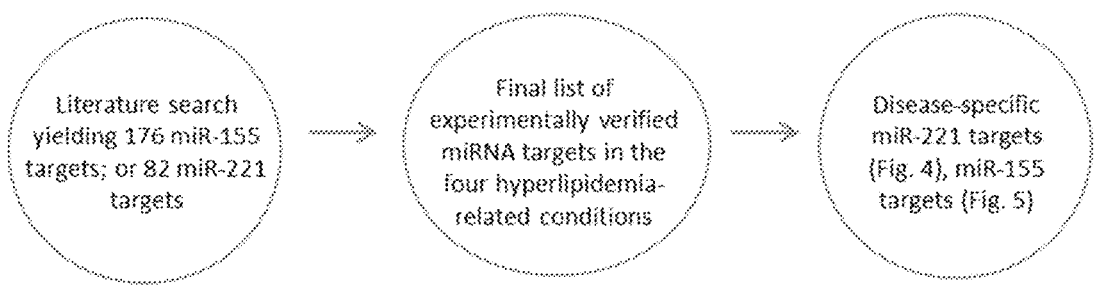

Compilation of miRNAs was done by manual literature search of the PubMed-NCBI database and by PCR array conducted in the laboratory. The search yielded a final list of 147 miRNAs that are significantly modulated in the four diseases. miRNAs were identified based on their expression levels in each disease condition. Compilation of microRNA-regulating transcription factors (TFs) was based on manual literature search through PubMed-NCBI database as well as the experiment-based RegNetwork: Regulatory Network Repository database (Liu et al., 2015, Database (Oxford), 2015:bav095). TFs were selected based on peer-reviewed published experimental data. This yielded a final list of 118 non-redundant experimentally verified miRNA-regulating TFs. Compilation of miR-221/miR-155 mRNA targets was done by manual literature search of experimentally verified targets, yielding 176 (miR-155) and 82 (miR-221) targets (FIG. 1B, FIG. 1D).

Pathway Analyses

Figure 1E:
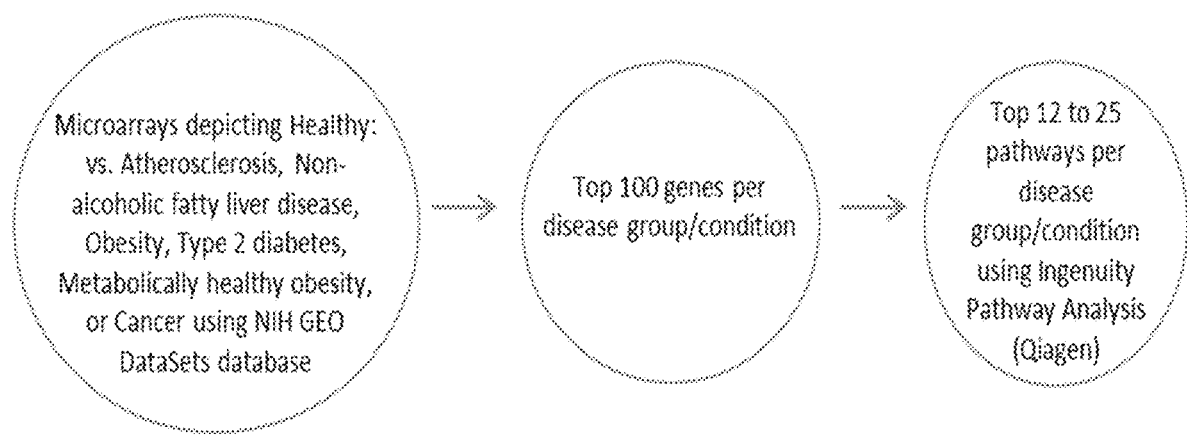

Pathway analyses were produced using Ingenuity Pathway Analysis (IPA, Qiagen): miRNAs having the same expression direction were analyzed in each category (e.g. all miRNAs that are significantly increased in atherosclerosis had their own category; all miRNAs that are significantly decreased in atherosclerosis had their own category). The designation up or down was then given, which reflected the expression direction of the miRNAs (FIG. 6A through FIG. 6F). Compilation of pathways in the four hyperlipidemia-related diseases, cancer and metabolically healthy disease (MHO) was done using NIH Gene Expression Omnibus (GEO) DataSets-NCBI database to compare microarrays for healthy versus (vs) disease human subjects; metabolic unhealthy vs metabolically healthy obese patients. The top 100 significantly upregulated genes per condition were obtained; and then the top 12 to 25 pathways per condition were obtained. Finally, these pathways were overlapped between diseases/conditions to identify shared pathways using IPA and Venn Diagram analysis (FIG. 1E, FIG. 7).

The results of the experiments are now described.

miRNA Expression Profile Shows that Only a Few Shared miRNAs are Potentially Crucial Regulators of Hyperlipidemia-Related Diseases.

Metabolic syndrome is a condition that refers to collective risk factors that increase an individual's likelihood of developing cardiovascular disease; and is an increasingly common diagnosis in the U. S. (Moore, J. X. et al., 2017, Preventing Chronic Disease 14:160287). Conditions that constitute metabolic syndrome include obesity and insulin resistance, while those resulting from metabolic syndrome include NAFLD, T2DM (Srikanthan, K. et al., 2016, International Journal of Medical Sciences, 13(1):25-38) and atherosclerosis (Gonzalez-Navarro, H. et al., 2008, Arteriosclerosis, Thrombosis, and Vascular Biology, 28:2187-2194). Largely having unique distinct features that define each disease, inflammation and hyperlipidemia stand out as shared characteristics of the four diseases (FIG. 1A). Moreover, these four diseases continue to be prevalent within American society. Therefore, synthesizing a more comprehensive understanding of the molecules and mechanisms involved in these disease processes is requisite.

Figure 2A:
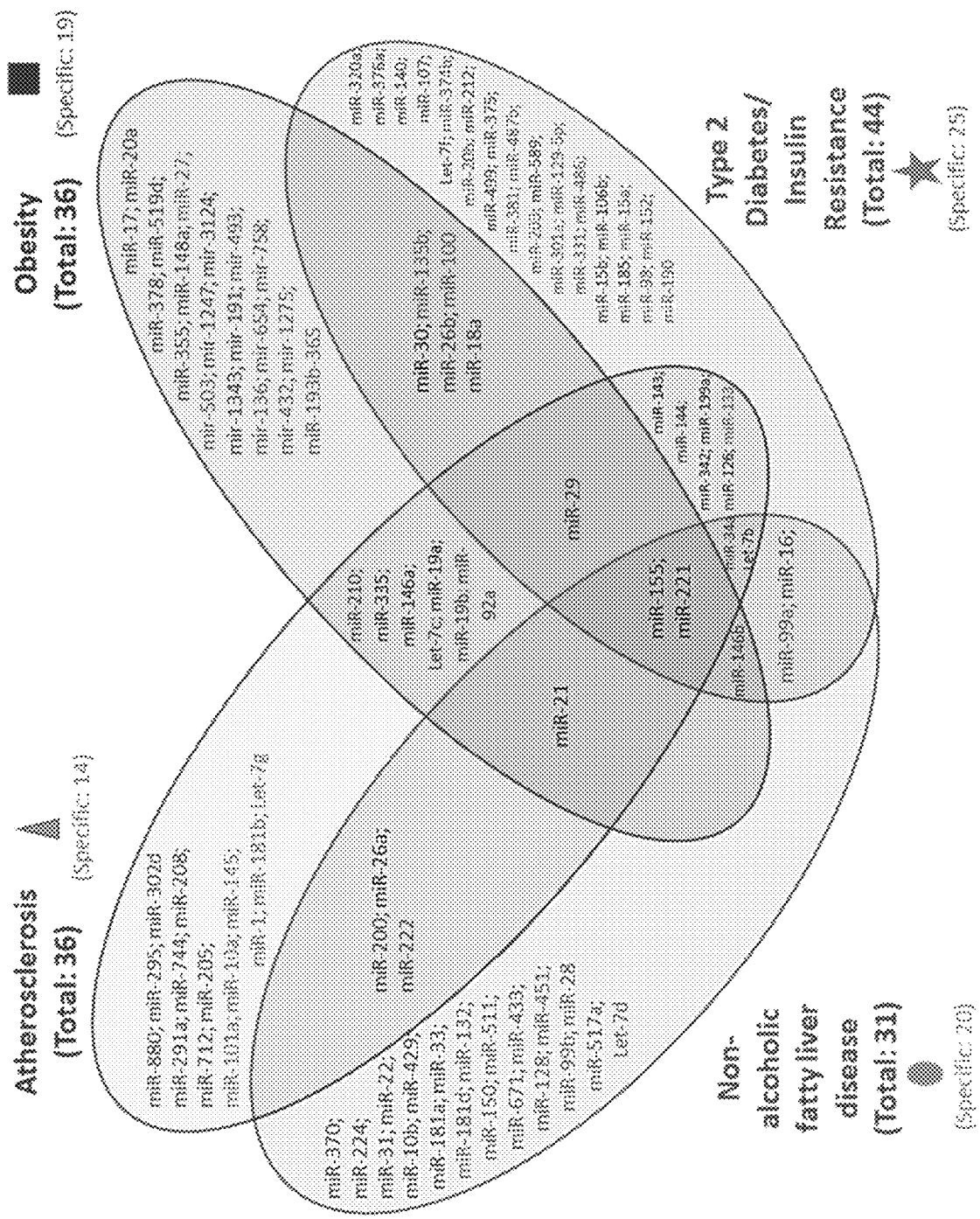

MiRNAs play an indispensable role in the development of the hyperlipidemia-related pathologies atherosclerosis, NAFLD, obesity and T2DM. Thus, the miRNAs that were shared among diseases were determined and were compared with the miRNAs unique to a disease. In previous publication, it was highlighted that deficiency of a single miRNA can produce drastic and opposing phenotypes, it was hypothesized that only a few miRNAs would be shared, leaving the vast majority of miRNAs unique to a single disease. A literature search approach was employed to determine experimentally verified miRNAs as well as used data generated from the microarray (FIG. 1B). Using Venn diagram analysis to easily determine disease-unique miRNAs versus miRNAs shared among diseases, it was found that of nearly 150 miRNAs that were shown to be significantly upregulated or downregulated in any of the four diseases, the vast majority of miRNAs were uniquely modulated within each disease type while only a few miRNAs were shared (FIG. 2A). In terms of percentage, out of a total of 36 atherosclerosis-relevant miRNAs, it was found that 39% were atherosclerosis-specific miRNAs, while 61% of all atherosclerosis-relevant miRNAs were shared (i.e., these miRNAs are relevant in atherosclerosis and one or more other diseases). Out of 31 NAFLD-relevant miRNAs, NAFLD-specific miRNAs accounted for 64.5% while shared miRNAs were 35.5%. Out of 36 obesity-relevant miRNAs, unique miRNAs were 52.7% while shared were 47.3%. Out of 44 T2DM/insulin resistances (T2DM/IR)-relevant miRNAs, 56.8% were unique miRNAs while 43.2% were shared miRNAs.

Some shared miRNAs were consistently expressed in the same direction while others were differentially expressed between diseases (shown in black color, FIG. 2A). For example, the differentially expressed let-7b was significantly reduced in atherosclerosis and T2DM/IR but increased in NAFLD. MiR-19a, miR-146a, and miR-335 were reduced in atherosclerosis but increased in obesity. MiR-21 was increased in both atherosclerosis and obesity but decreased in NAFLD. MiR-26a was reduced in atherosclerosis and increased in NAFLD. MiR-30 was upregulated in obesity but downregulated in T2DM/IR, whereas both miR-126 and miR-342 were increased in atherosclerosis and reduced in T2DM/IR. On the contrary, miR-143 and miR-199a were decreased in atherosclerosis but increased in T2DM/IR. Finally, both miR-155 and miR-221 were increased in atherosclerosis but decreased in obesity, while differentially expressed in NAFLD and T2DM/IR (FIG. 2B).

Moreover, miRNAs that are shared by at least three diseases were identified. MiR-21 was upregulated in atherosclerosis and obesity but downregulated in NAFLD; miR-29 was increased in atherosclerosis, obesity and T2DM/IR; miR-146b was significantly expressed in NAFLD, obesity and T2DM/IR; miR-34a was increased in atherosclerosis, NAFLD, and T2DM/IR, while let-7b was reduced in atherosclerosis and T2DM/IR but increased in NAFLD (FIG. 2B). Most interestingly, miR-155 and miR-221 were the only miRNAs that were found to be significantly modulated in all four pathologies, with miR-155 being significantly increased in atherosclerosis and reduced in the remaining three diseases while miR-221 was upregulated in atherosclerosis, NAFLD and T2DM/IR but lower in the obese phenotype.

Differentially Expressed miRNAs May Serve as Biomarkers for Hyperlipidemia-Related Single and Shared Diseases.

Based on miRNA analyses (FIG. 2A, FIG. 2B), miRNAs were classified as three types of biomarkers for (i) single disease condition; (ii) that for two or more co-existing, and/or (iii) shared, diseases. These miRNA markers were also categorized as upregulated and downregulated. For patients diagnosed with only atherosclerosis, associated upregulated miRNAs include miR-126, miR-155 and miR-342, and miRNAs represented by the red triangle symbol. Similarly, associated downregulated miRNAs include miR-19a, miR-335 and other miRNAs designated by the green triangle symbol. For patients diagnosed with only NAFLD, upregulated miRNAs associated included let-7b and miR-26a, along with other miRNAs represented by the red oval symbol, while miR-21 and miRNAs represented by green oval symbol were reduced. For obese patients, associated miRNAs included increased expression of miR-19a, miR-30, miR-146a, miR-335 and the miRNAs represented by the red square symbol; while miR-221 along with miRNAs depicted by green square symbol were decreased. Lastly, for T2DM/IR patients, associated miRNAs included increased miR-143, miR-199a, and the miRNAs represented by the red star symbol as well as reduced miR-30, miR-126b, miR-342 and miRNAs depicted by the green star symbol. Please note that symbols represent miRNAs that were uniquely expressed in the classical solitary diseases as shown in FIG. 2A. For patients having co-morbid conditions, the miRNA markers were understandably fewer and therefore more specific. In patients having both atherosclerotic and NAFLD conditions, possible miRNA markers were miR-200 and miR-222. An atherosclerotic and T2DM/IR condition was marked by increased miR-144 but reduced let-7b and miR-133. An atherosclerotic and obese condition was associated with increased let-7c, miR-19b, miR-21, miR-92a and miR-210. It was proposed that patients diagnosed with a NAFLD-T2DM/IR co-morbid condition would exhibit increased miR-16 and decreased miR-99a. An obesity and T2DM/IR condition was marked by increased miR-18a, miR-26b but reduced miR-100 and miR-135b. MiR-221 and miR-34 were upregulated markers in the atherosclerosis, NAFLD, T2DM/IR condition, whereas miR-29 was increased in atherosclerosis, obesity and T2DM/IR condition. Lastly, NAFLD, obesity, and T2DM/IR exhibit increased miR-146b but reduced miR-155 (FIG. 2C). Interestingly, there were no shared miRNAs between only NAFLD and obesity; atherosclerosis, NAFLD and obesity; or atherosclerosis, NAFLD, obesity, and T2DM/IR that were significantly expressed in the same direction (i.e. no miRNAs were all increased or all decreased in these co-morbidities).

As mentioned earlier, miR-155 and miR-221 were the only miRNAs modulated in all four HRDs; and miR-155 deletion in the ApoE$^{-/-}$ mice led to a new MHO model, whereby obesity and NAFLD were present along with reduced atherosclerosis and hyperglycemia without insulin resistance. It was observed in FIG. 2B that deficiency of miR-221 may result in MHO as well, since it is significantly upregulated in atherosclerosis, NAFLD, and T2DM/IR but reduced in obesity.

The Majority of Transcription Factors are Specific to Single Disease Conditions while Only a Few Transcription Factors are Shared within Co-Existing Disease Conditions Transcription factors (TFs) play a critical role in regulating the expression of protein-coding genes, among them of course other TFs. These all-important proteins also regulate miRNAs in the same way as they do protein-coding genes, i.e., by binding to their promoters to either inhibit or promote transcription. It was next researched that the TFs that have been experimentally verified to bind the promoter or enhancer regions of each miRNA gene in order to elicit an increase in miRNA expression. In other words, only TFs shown to promote the miRNAs' expression were included. In terms of methodology, two approaches to identify TFs were conducted. In the first approach, for each disease, TFs that regulated at least two miRNAs within each disease type as well as within co-existing disease combination groups were included. The second approach employed was to identify TFs that commonly regulated the only miRNAs that are modulated in all four disease types: miR-155 and miR-221. Using these approaches, it was found that three transcription factors, EGR1, NFκB (11) and STAT3, were regulators of miRNAs in all four diseases (FIG. 3A, FIG. 3B).

EGR1 and STAT3 were positive regulators of single-disease miRNAs in all four diseases (FIG. 3A), while NFκB and STAT3 were found to positively regulate both miR-155 and miR-221 (FIG. 3B). Interestingly, STAT3 was a TF of miRNAs in all four disease conditions regardless of which approach was used (FIG. 3A, FIG. 3B).

Downstream mRNA Targets of miR-155 and miR-221 in Atherosclerosis, NAFLD, Obesity and T2DM/IR are Largely Unique to Each miRNA and are Differentially Expressed in Each of the Four Diseases, Leading to Different Phenotypic Outcomes.

Figure 4B:
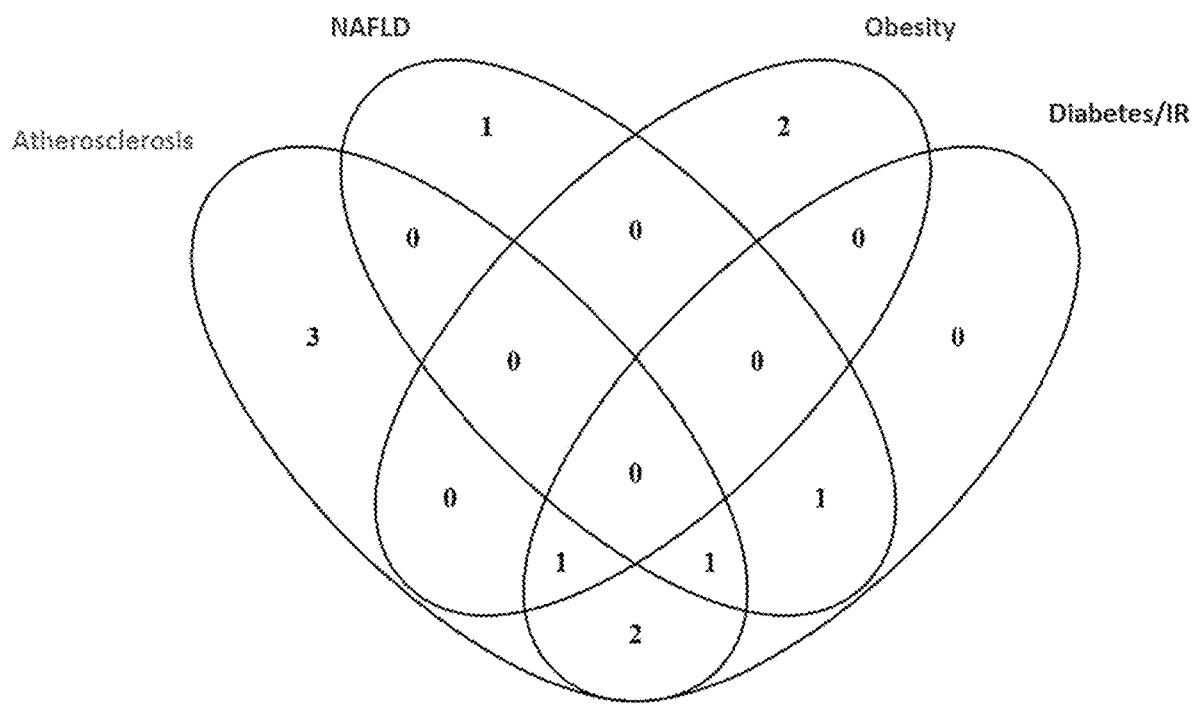
Figure 5B:
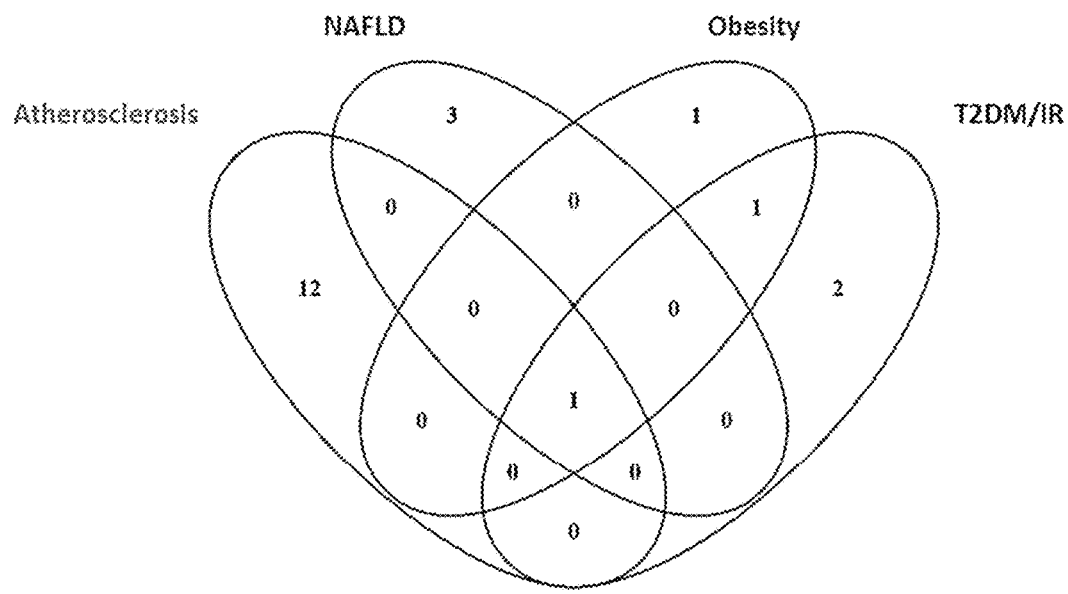

Next, it was sought to identify miR-155 and miR-221 mRNA targets that play a role in the development of atherosclerosis, NAFLD, obesity and T2DM/IR. Of note, due to lack of the microarray data associated with MHO, the mRNA targets for those two miRNAs in this condition could not be determined. It is hypothesized that varying phenotypes resulting from miR-155 deletion in the atherosclerotic mice resulted from varying expression of downstream targets. From 82 known targets of miR-221, it was found that eleven were experimentally verified in one or more of the four hyperlipidemia-related diseases. These were cyclin-dependent kinase inhibitor 1B (CDKN1B); CDKN1C; KIT proto-oncogene receptor tyrosine kinase (KIT); BCL2 binding component 3 (BBC3); TIMP metallopeptidase inhibitor 3 (TIMP3); intercellular adhesion molecule 1 (ICAM1); phosphatase and tensin homolog (PTEN); ETS proto-oncogene 1, transcription factor (ETS1); thrombospondin 1 (THBS1); P21 (RAC1) activated kinase 1 (PAK1); and phosphoinositide-3-kinase regulatory subunit 1 (PIK3R1) (FIG. 4A). While none of the targets were experimentally verified in all four diseases, it was found that PTEN was targeted in atherosclerosis, NAFLD and T2DM/IR, while ETS1 was targeted in atherosclerosis, obesity and T2DM/IR (FIG. 4B). From 176 targets of miR-155, twenty were experimentally verified in one or more of the four hyperlipidemia-related diseases: Fas associated via death domain (Fadd); nuclear receptor subfamily 1 group H member 3 (Nr1h3); suppressor of cytokine signaling 1 (Socs1); CCAAT/enhancer binding protein beta (Cebpb); histone deacetylase 4 (Hdac4); Ets1; HMG-Box transcription factor 1 (Hbp1); mitogen-activated protein kinase 1 (Mapk1); peroxisome proliferator activated receptor gamma (Pparg); Spi-1 proto-oncogene (Sfpi1); SKI proto-oncogene (Ski); angiotensin II receptor type 1 (AT1R); calcium regulated heat stable protein 1 (CARHSP1); colony stimulating factor 1 receptor (CSF1R); mitogen-activated protein kinase kinase kinase 10 (MAP3K10); myeloid differentiation primary response 88 (MYD88); Forkhead box P3 (Foxp3); carboxylesterase 3 (Ces3/TGH); B-cell CLL/lymphoma 6 (Bcl6); and serine/threonine kinase 3 (Mst2) (FIG. 5A). Interestingly, Socs1 was a common target in all four disease types (FIG. 5B). Moreover, ETS1 is a shared target of both miR-155 and miR-221 (FIG. 4, FIG. 5).

Disease-Unique and Disease-Shared Groups have Modulated Pathways in Cancer, Metabolism, Immunology, Arthritis, Proliferation/Survival, and Development.

Next, it was decided to assess the pathways that each of these disease groupings are involved in. Employing Qiagen's Ingenuity Pathway Analysis software, it was found that each disease grouping, with the exception of ANO (atherosclerosis, NAFLD and obesity) and ANOD (atherosclerosis, NAFLD, obesity and T2DM), involved three or more of six pathway categories: Cancer, Proliferation/Survival, Arthritis, Development, Metabolism, and Immunology. As an example, in the NOD (NAFLD, obesity and T2DM/IR) condition, the pathways related to arthritis, immunology and metabolism were active. More specifically, molecules related to Role of Macrophages, Fibroblasts and Endothelial Cells in Rheumatoid Arthritis (Arthritis); Hepatic Cholestasis, Hepatic Fibrosis/Hepatic Stellate Cell Activation, PPAR Signaling (Metabolism); and INOS Signaling (Immunology) were increased, suggesting that chronic presence of NOD may possibly lead to the development of pathway-indicated pathologies (FIG. 6A through FIG. 6F and FIG. 6I). Next, the percentage of pathway subsets that were significantly modulated among all pathway subsets within a category were determined. For instance, referring to FIG. 6A through FIG. 6F, in AD (atherosclerosis and T2DM), six out of 12 total pathway subsets were modulated so that 50 percent of cancer-related pathways were modulated (FIG. 6G). Therefore, it was found that 15 out of 16 disease grouping (ANO and ANOD were excluded, since no miRNAs were expressed in the same direction in these co-morbidities) had modulated pathways in Cancer category. Next, percentage of upregulated and downregulated pathways per disease group per pathway category was examined. For example, under Cancer pathways, there were four modulated pathway subsets under ND. Three of the four pathway subsets were upregulated and the remaining one was downregulated. Therefore, 75 percent of pathway subsets was upregulated and 25 percent was downregulated under ND. It was found that AN has the most upregulated pathways across pathway categories (five out of six categories). On the other hand, AD and OD had the most downregulated pathways across pathway categories (four out of six categories) (FIG. 6H). Interestingly, it was identified that atherosclerosis, the AN (atherosclerosis and NAFLD), and the OD (obesity and T2DM/IR) groupings were involved in pathways found in five out of six categories. All three had modulated pathways in Cancer, Immunology, and Proliferation/Survival pathway categories (FIG. 6I). As stated earlier, miRNAs having the same expression direction were analyzed in each disease/combination category. However, no miRNAs were found that had the same expression direction in all four disease conditions.

Top Pathways in Hyperlipidemia-Related Diseases, MHO, and Cancer Show Multiple Shared Pathways.

Figure 7A:
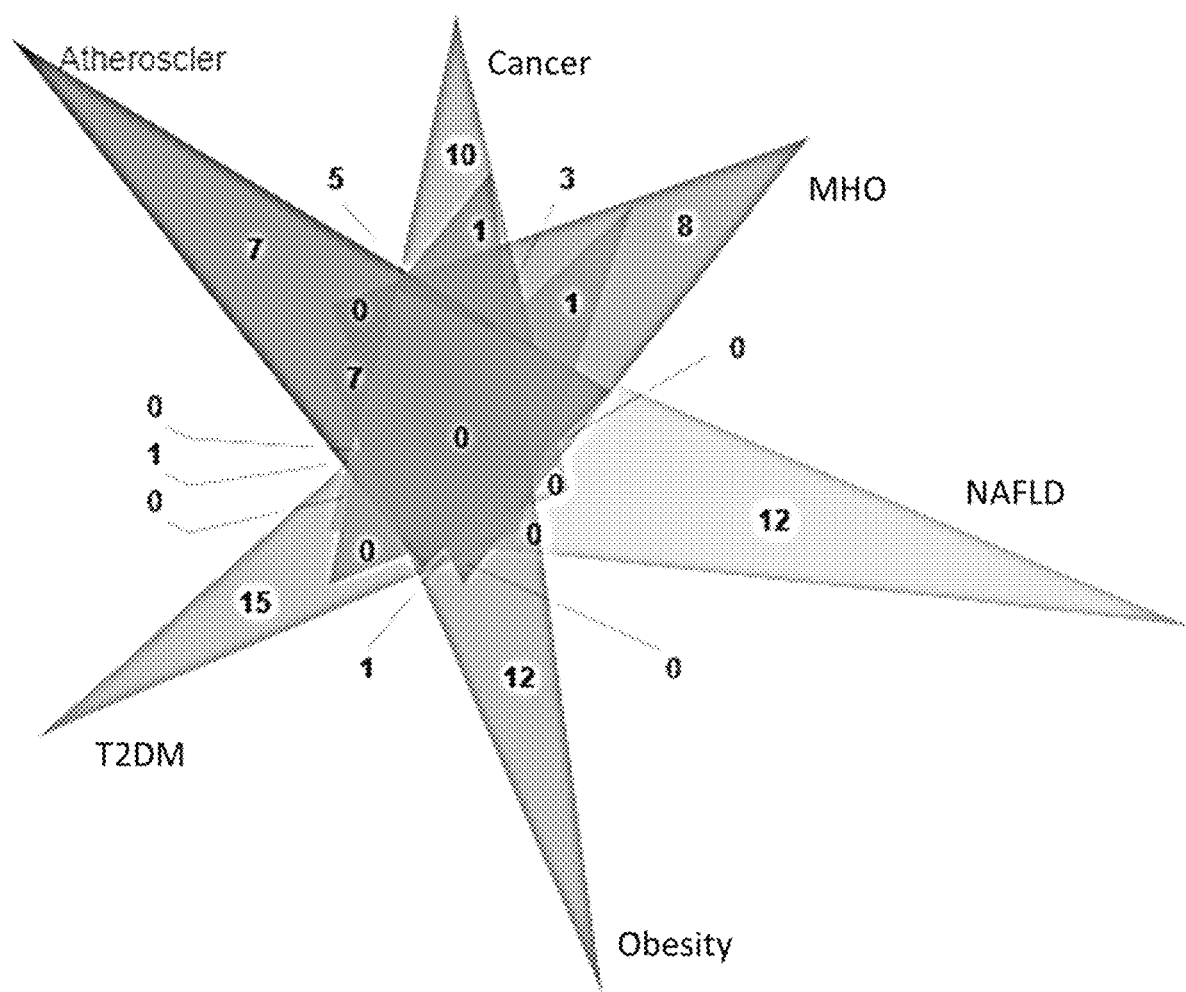

As mentioned earlier, a new metabolically healthy obesity (MHO) model was recently established (Soh et al., 2013, Nat Med, 19(7): 892-900). So far, hyperlipidemia-related diseases of atherosclerosis, NAFLD, and T2DM, were studied, which are typically associated with classical obesity, as well as studied MHO. It was also found that the most modulated pathways are the cancer-related pathways (FIG. 6G). Using GEO DataSets database, microarrays (healthy versus (vs) atherosclerotic human artery/plasma; healthy vs NAF human liver; healthy vs obese adipose tissue; healthy vs diabetic human pancreas/blood/vessels/liver; healthy vs malignant human tissue; and classically unhealthy obesity vs MHO) were compared. The top 100 significantly upregulated genes per condition were obtained and then the top 12 to 25 pathways per condition were obtained. More specifically, the top 25 pathways (atherosclerosis); 12 pathways (NAFLD); 25 pathways (obesity); 19 pathways (T2DM); 15 pathways (MHO) and 23 pathways (cancer) were based on significance (p<0.05). These pathways were then overlapped to identify shared pathways (FIG. 7A and FIG. 7B). While no pathways were shared among all six conditions, it was found that the following comorbidities had shared pathways: Atherosclerosis+Cancer; Atherosclerosis+Obesity; Atherosclerosis+T2DM; Cancer+MHO; Cancer+Obesity; MHO+T2DM; Obesity+T2DM; Atherosclerosis+Cancer+Obesity; Atherosclerosis+MHO+Obesity; Atherosclerosis+Cancer+

MHO+Obesity; and Atherosclerosis+Cancer+MHO+T2DM. Furthermore, Atherosclerosis Signaling and Pathogenesis of Multiple Sclerosis pathways were shared among four out of six conditions (FIG. 7B).

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of monitoring efficacy of a treatment for a hyperlipidemia-related disease (HRD) in a subject, wherein said HRD is obesity, the method comprising:
   a. administering to said subject a therapeutic to treat obesity,
   wherein said therapeutic increases levels of at least one miRNA selected from the group consisting of: miR-221, miR-503, miR-27, miR-493, miR-136, miR-654, miR-758, miR-432, miR-1275, miR-193b-365, miR-135b, and miR-100, and wherein said therapeutic comprises a nucleic acid; or
   wherein said therapeutic decreases levels of at least one miRNA selected from the group consisting of: miR-17, miR-20a, miR-378, miR-519d, miR-355, miR-148a, miR-1247, miR-3124, miR-1343, miR-191, miR-30, miR-21, miR-19a, miR-146a, miR-26b, miR-18a, miR-210, miR-19b, miR-92a, miR-29, miR-146b, let-7c and miR-335, and wherein said therapeutic comprises an antisense nucleic acid;
   b) measuring the level of at least one miRNA in a biological sample from the subject; and
   c) comparing the level of the at least one miRNA in the biological sample from the subject to the level of the at least one miRNA in a comparator,
   wherein the level of the at least one miRNA in the biological sample from the subject is increased compared to the level of the at least one miRNA in the comparator, wherein the at least one miRNA is selected from the group consisting of miR-155, miR-221, miR-503, miR-27, miR-493, miR-136, miR-654, miR-758, miR-432, miR-1275, miR-193b-365, miR-135b, and miR-100; or
   wherein the level of the at least one miRNA in the biological sample from the subject is decreased compared to the level of the at least one miRNA in the comparator, wherein the at least one miRNA is selected from the group consisting of miR-17, miR-20a, miR-378, miR-519d, miR-355, miR-148a, miR-1247, miR-3124, miR-1343, miR-191, miR-30, miR-21, miR-19a, miR-146a, miR-26b, miR-18a, miR-210, miR-19b, miR-92a, miR-29, miR-146b, let-7c and miR-335; and
   wherein a difference between the level of the at least one miRNA in the biological sample from the subject and the level of the at least one miRNA in the comparator indicates that the treatment has efficacy in treating the HRD.

2. The method of claim 1, wherein the biological sample is at least one selected from the group consisting of blood, serum, plasma, and any combination thereof.

3. The method of claim 1, wherein the method of measuring the level of the at least one miRNA in the biological sample from the subject comprises at least one technique selected from the group consisting of reverse transcription, polymerase chain reaction (PCR), and microarray analysis.

4. The method of claim 1, wherein the comparator is at least one comparator selected from the group consisting of a sample from a diseased subject not receiving treatment, a sample from the subject obtained at an earlier time point during treatment, a sample from the subject obtained prior to treatment and a level in a population of diseased subjects not receiving treatment.

* * * * *